United States Patent
Gulliver et al.

(10) Patent No.: US 10,449,122 B2
(45) Date of Patent: Oct. 22, 2019

(54) TUBE SECUREMENT SYSTEM

(71) Applicant: Fisher & Paykel Healthcare Limited, Auckland (NZ)

(72) Inventors: Laurence Gulliver, Auckland (NZ); Caroline Geraldine Hopkins, Caven (IE); Neil Gray Duthie, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 799 days.

(21) Appl. No.: 14/395,047

(22) PCT Filed: Apr. 17, 2013

(86) PCT No.: PCT/NZ2013/000069
§ 371 (c)(1),
(2) Date: Oct. 16, 2014

(87) PCT Pub. No.: WO2013/157960
PCT Pub. Date: Oct. 24, 2013

(65) Prior Publication Data
US 2015/0090255 A1    Apr. 2, 2015

Related U.S. Application Data

(60) Provisional application No. 61/625,583, filed on Apr. 17, 2012, provisional application No. 61/678,028, filed on Jul. 31, 2012.

(51) Int. Cl.
*A61J 15/00*   (2006.01)
*A61M 16/06*   (2006.01)
*A61M 25/02*   (2006.01)

(52) U.S. Cl.
CPC ....... *A61J 15/0061* (2013.01); *A61J 15/0053* (2013.01); *A61M 16/0688* (2014.02);
(Continued)

(58) Field of Classification Search
CPC .......... A61M 16/0688; A61M 16/0461; A61M 16/047; A61M 16/0666; A61M 16/0672;
(Continued)

(56) References Cited

U.S. PATENT DOCUMENTS 3,046,989 A * 7/1962 Hill ....................... A61M 25/02
                                                    128/207.18
3,288,136 A   11/1966 Lund
(Continued)

FOREIGN PATENT DOCUMENTS

WO   WO 1998/53872    12/1998
WO   WO 2012/053910   4/2012

OTHER PUBLICATIONS

Jun. 26, 2013 Written Opinion of International Application No. PCT/NZ2013/00069 filed Apr. 17, 2013.

*Primary Examiner* — Joseph D. Boecker
(74) *Attorney, Agent, or Firm* — Knobbe Martens Olson & Bear LLP

(57) ABSTRACT

The invention relates to systems for securing a tube (e.g. feeding tube) and/or a patient interface or a dermal patch to a user. One embodiment comprises a holder, an interface side of the holder attachable to the patient interface or the dermal patch for securing a feeding tube to the patient interface or the patch, the holder comprising at least a first channel or recess for receiving the feeding tube to couple the feeding tube to the patient interface. Another embodiment comprises a patient interface itself comprising a backing for positioning on a patient's face, a dermal patch having a patient side and an interface side, the patient side of the patch attachable to the user, the patch comprising at least a first flap portion attachable to the tube for affixing the tube to the patch, a two-part releasable connection arrangement for releasably securing the patient interface to the patch.

22 Claims, 36 Drawing Sheets

(52) U.S. Cl.
CPC ......... *A61M 25/02* (2013.01); *A61M 16/0672* (2014.02); *A61M 2025/026* (2013.01); *A61M 2025/0226* (2013.01); *A61M 2025/0253* (2013.01); *A61M 2240/00* (2013.01)

(58) Field of Classification Search
CPC .............. A61M 16/0683; A61M 25/02; A61M 2025/0213; A61M 2025/0226; A61M 2025/024; A61M 2025/0246; A61M 2025/0253; A61M 2025/026; A61M 2025/0266; A61M 39/0247; A61M 39/0255; A61M 2039/085; A61M 2202/0482; A61M 2205/0216; A61M 2240/00; A61J 15/0003; A61J 15/0053; A61J 15/0061; Y10S 128/26
USPC .............. 128/207.18, 912, DIG. 26; 604/180
See application file for complete search history.

(56) References Cited

U.S. PATENT DOCUMENTS

| | | | | |
|---|---|---|---|---|
| 3,357,426 | A * | 12/1967 | Cohen | A61M 16/06 128/202.27 |
| 4,660,555 | A | 4/1987 | Payton | |
| 4,738,662 | A * | 4/1988 | Kalt | A61M 25/02 128/DIG. 15 |
| 4,838,867 | A | 6/1989 | Kalt et al. | |
| 4,986,815 | A * | 1/1991 | Schneider | A61M 25/02 128/DIG. 26 |
| 5,156,641 | A | 10/1992 | White | |
| D375,355 | S | 11/1996 | Bierman | |
| D375,356 | S | 11/1996 | Bierman | |
| 5,682,881 | A * | 11/1997 | Winthrop | A61M 16/0666 128/200.26 |
| 5,743,885 | A * | 4/1998 | Hoerby | A61M 16/0488 128/DIG. 26 |
| 5,752,511 | A * | 5/1998 | Simmons | A61F 5/08 128/206.11 |
| 6,132,398 | A | 10/2000 | Bierman | |
| 6,328,038 | B1 | 12/2001 | Kessler et al. | |
| D492,411 | S | 6/2004 | Bierman | |
| D503,977 | S | 4/2005 | Bierman | |
| D528,206 | S | 9/2006 | Bierman | |
| D563,552 | S | 3/2008 | Bierman et al. | |
| D601,249 | S | 9/2009 | Su et al. | |
| D604,411 | S | 11/2009 | Gomez | |
| D608,444 | S | 1/2010 | Kyvik et al. | |
| D838,841 | S | 1/2019 | Johnson et al. | |
| 2002/0157673 | A1 * | 10/2002 | Kessler | A61M 16/06 128/205.25 |
| 2003/0154987 | A1 | 8/2003 | Palmer | |
| 2004/0244799 | A1 * | 12/2004 | Landis | A61M 16/0683 128/206.21 |
| 2005/0092328 | A1 | 5/2005 | Herrick et al. | |
| 2009/0032018 | A1 * | 2/2009 | Eaton | A61M 16/0666 128/201.22 |
| 2010/0229872 | A1 * | 9/2010 | Ho | A61M 16/06 128/206.25 |
| 2010/0292649 | A1 * | 11/2010 | Morrison | A61M 25/02 604/180 |
| 2011/0303224 | A1 * | 12/2011 | Widgerow | A61M 16/0666 128/207.18 |
| 2012/0037167 | A1 * | 2/2012 | Quiray | A61M 16/0666 128/858 |
| 2012/0111332 | A1 * | 5/2012 | Gusky | A61M 16/0666 128/205.25 |
| 2012/0167894 | A1 * | 7/2012 | O'Leary | A61M 16/0666 128/207.18 |

* cited by examiner

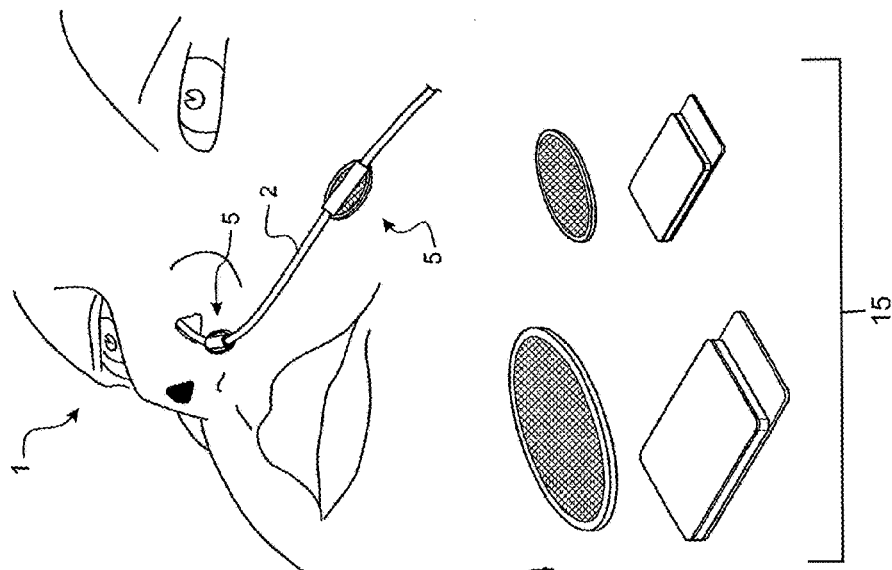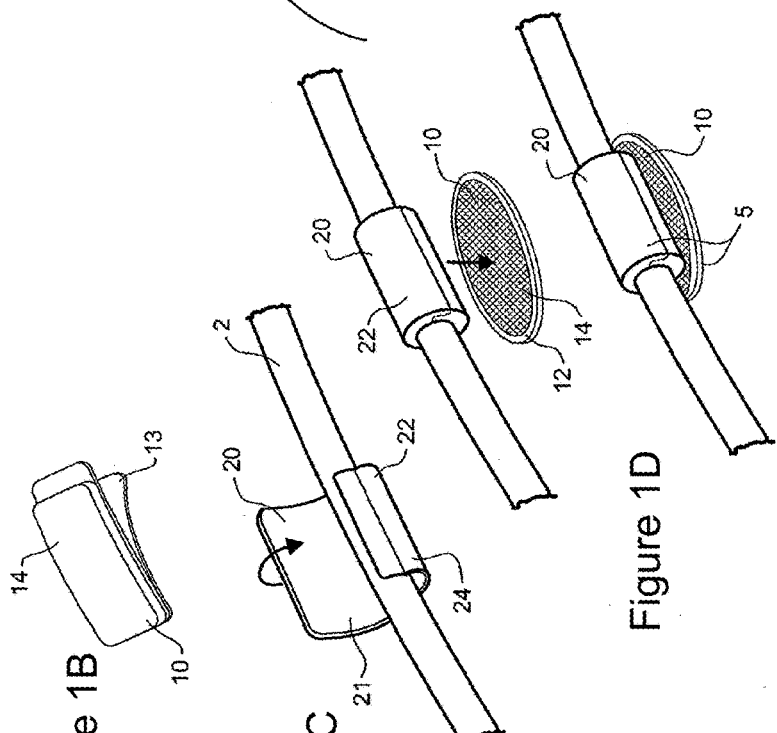

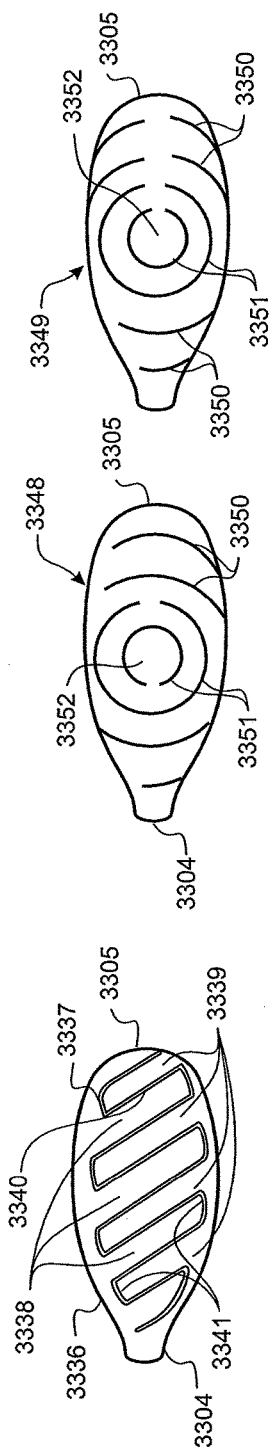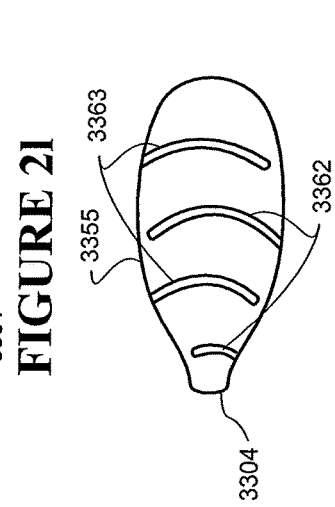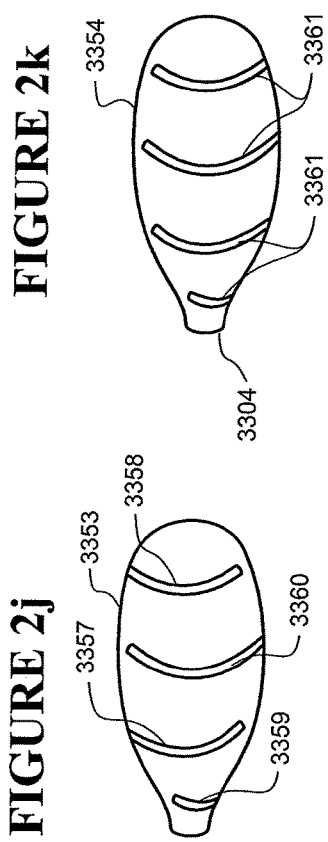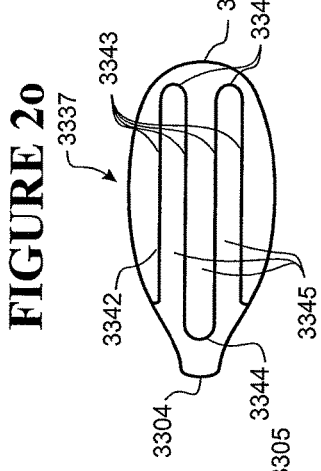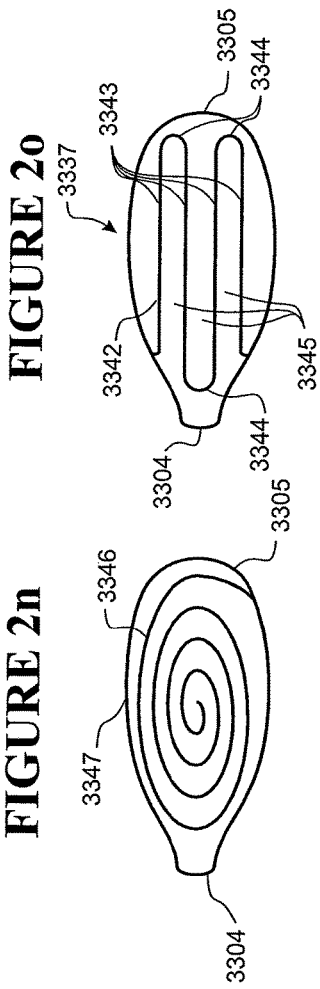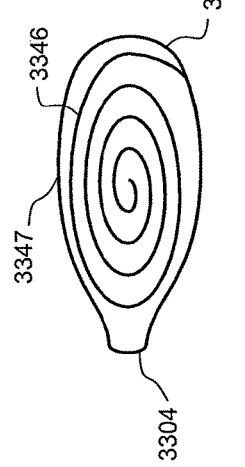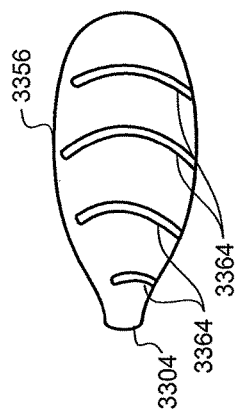

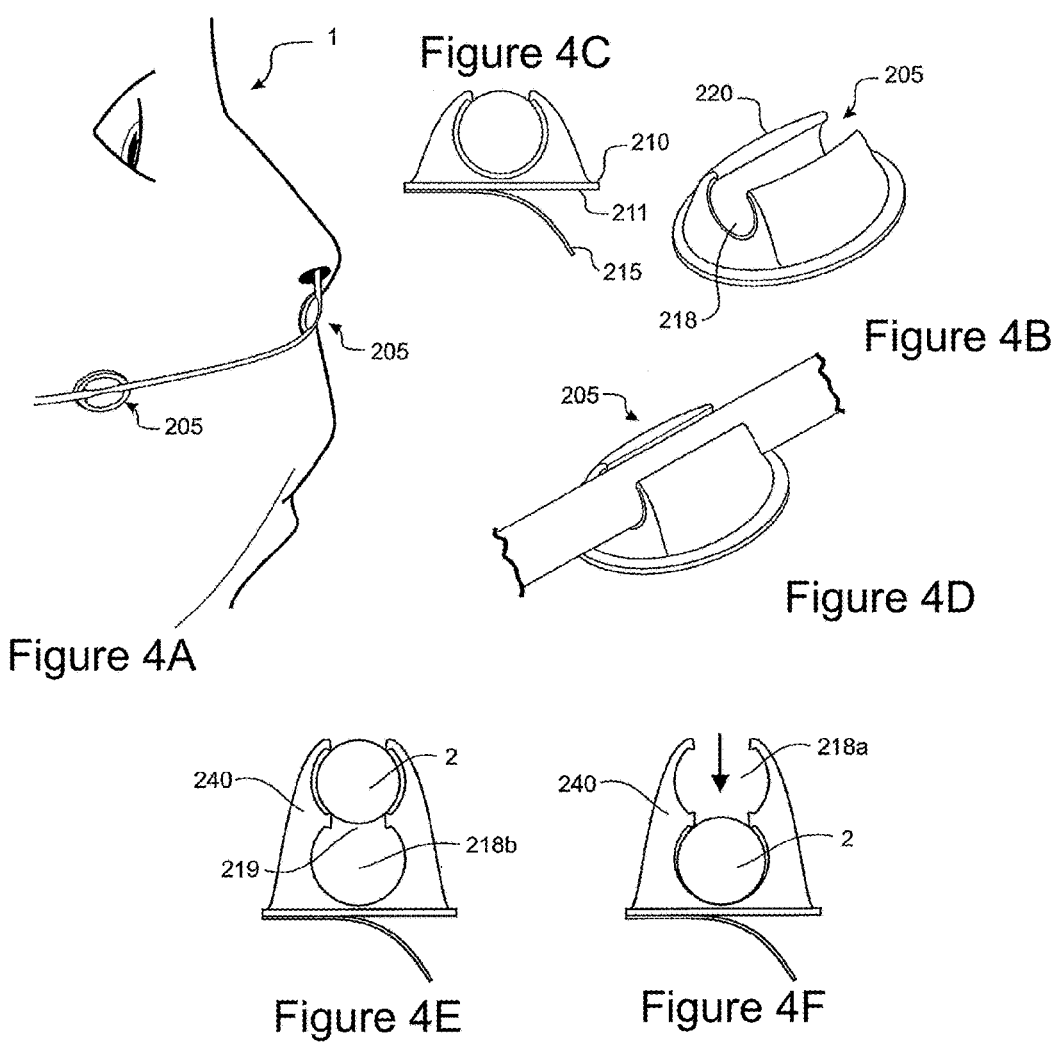

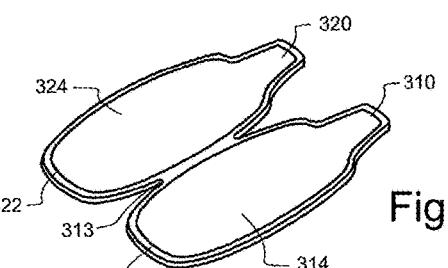
Figure 12A
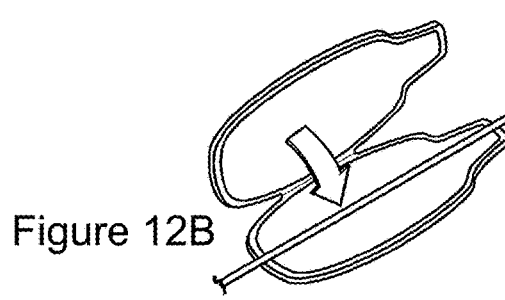
Figure 12B
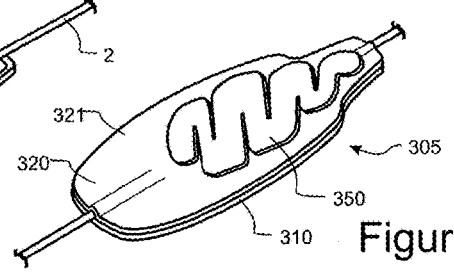
Figure 12C
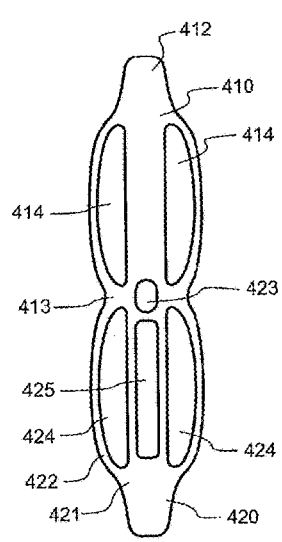
Figure 13A
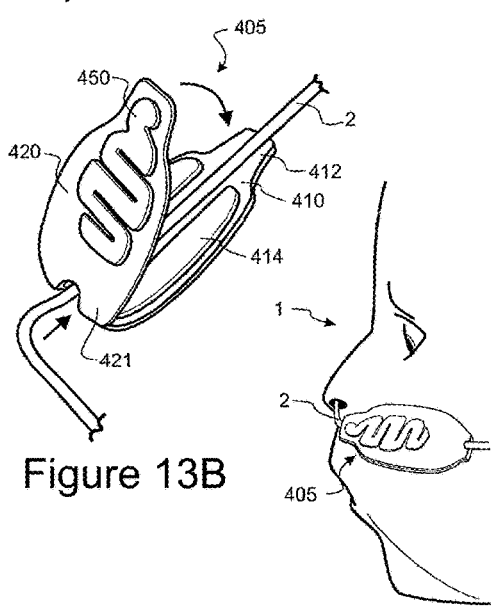
Figure 13B
Figure 13C

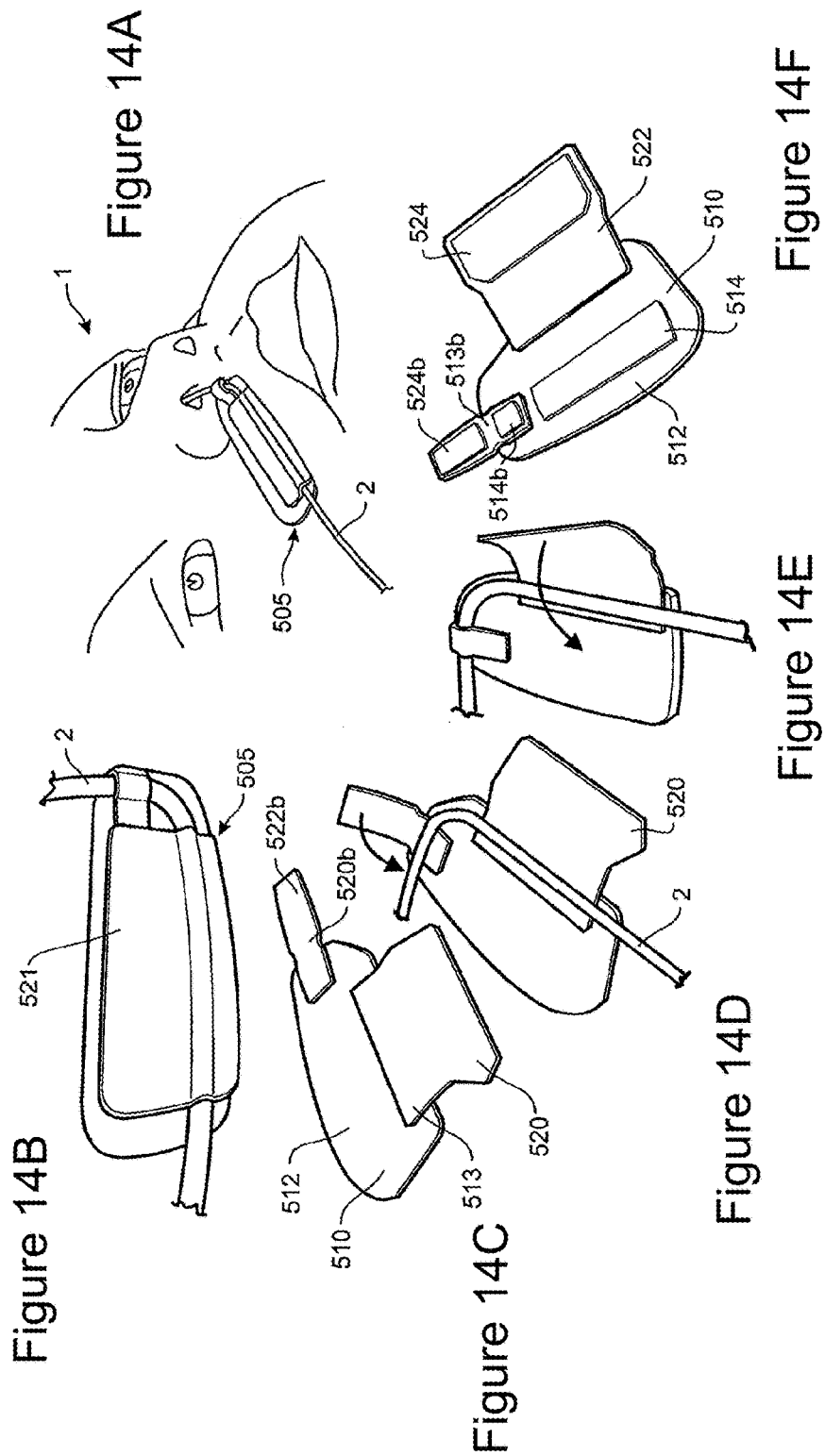

Figure 15A
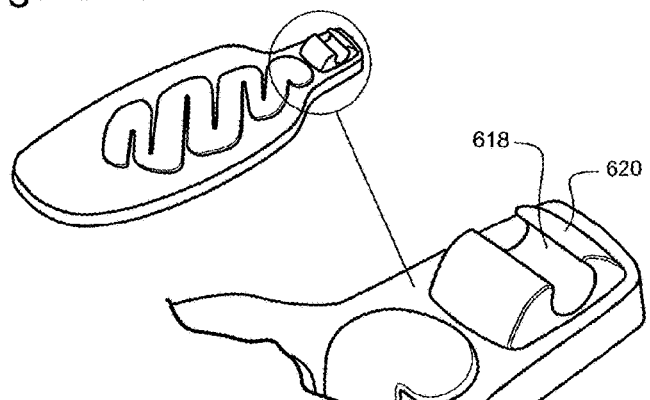
Figure 15B
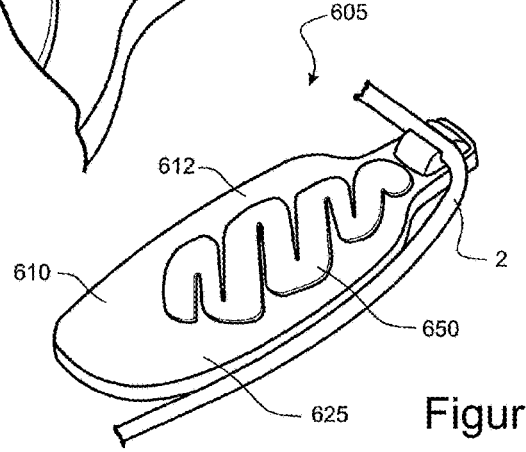
Figure 15C
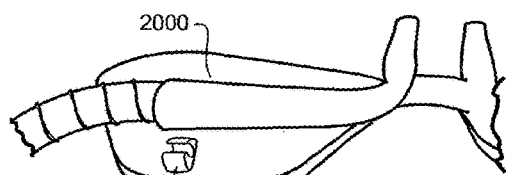
Figure 15D
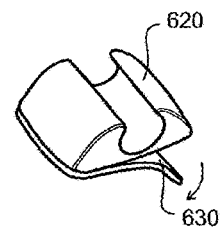
Figure 15E

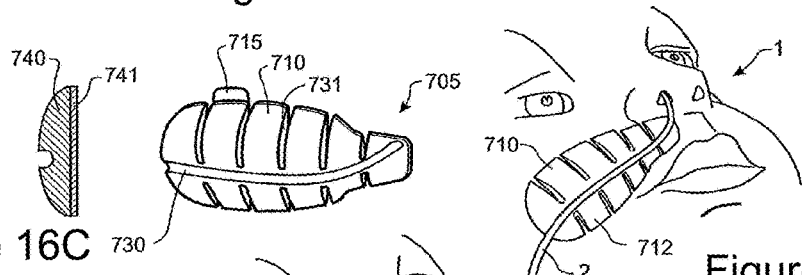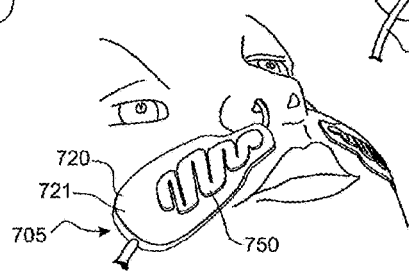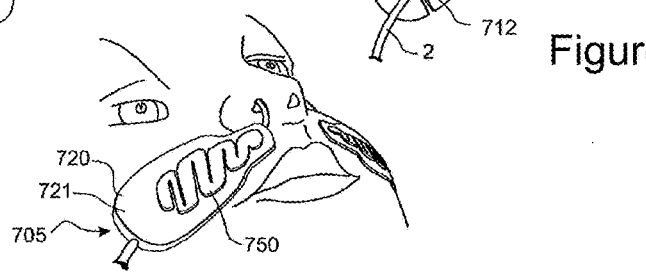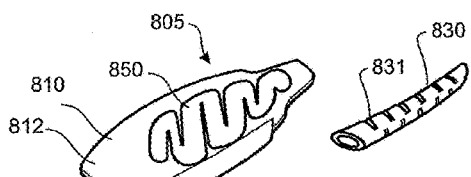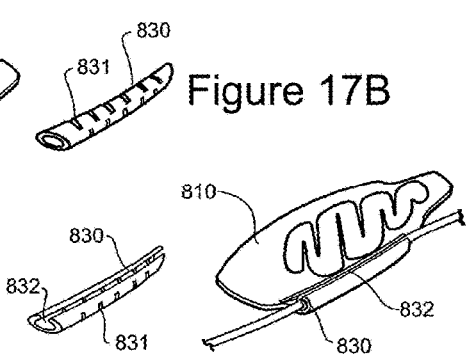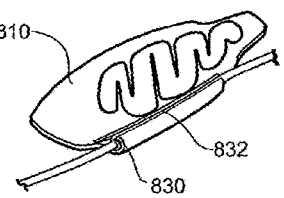

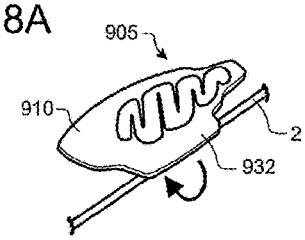
Figure 18A
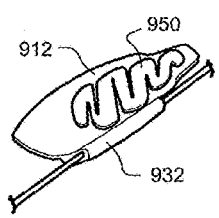
Figure 18B
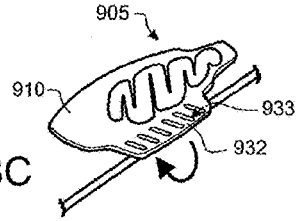
Figure 18C
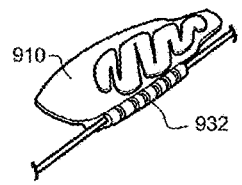
Figure 18D
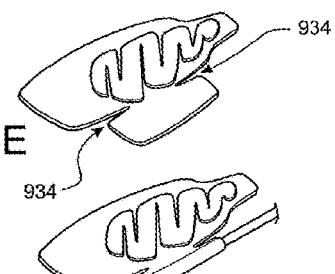
Figure 18E
Figure 18F
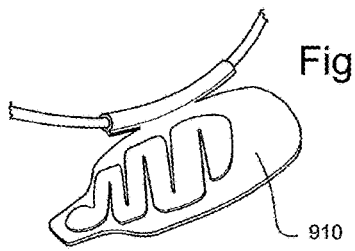
Figure 18H
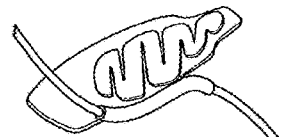
Figure 18G
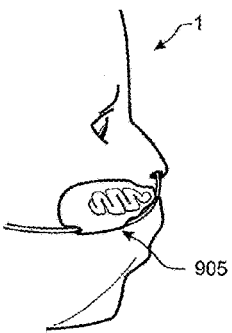
Figure 18I

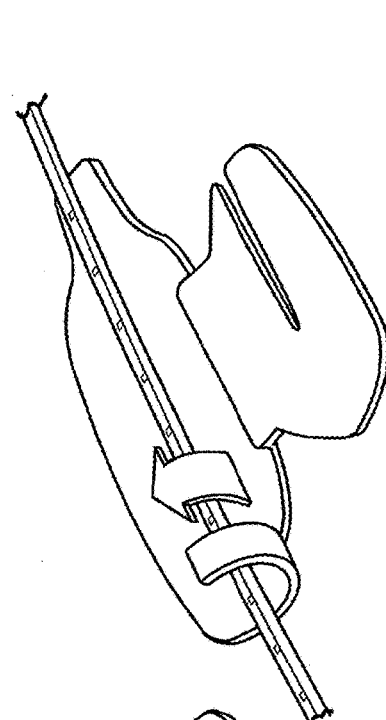
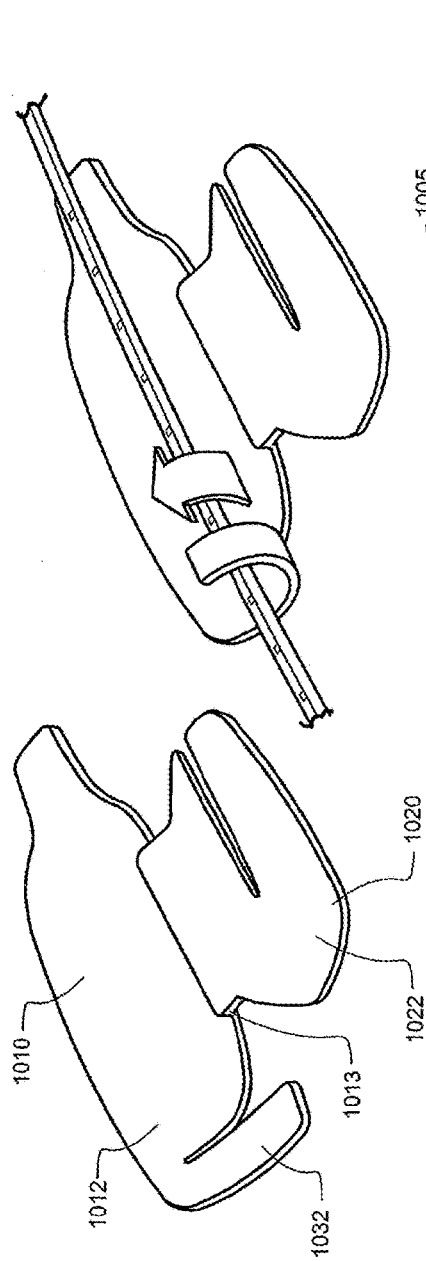
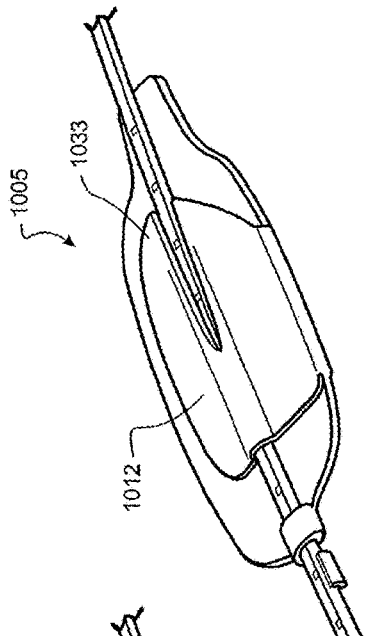
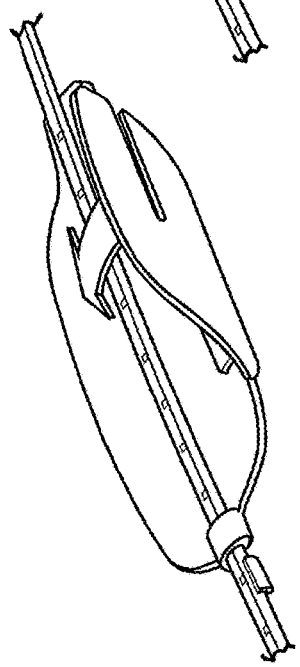

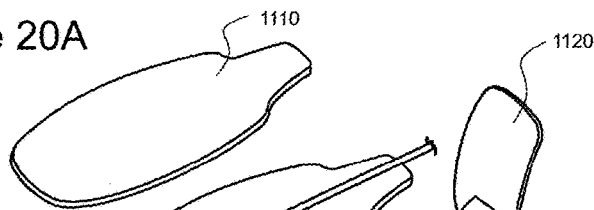
Figure 20A
Figure 20B
Figure 20C
Figure 20D
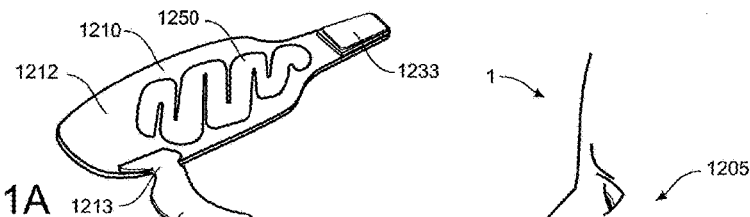
Figure 21A
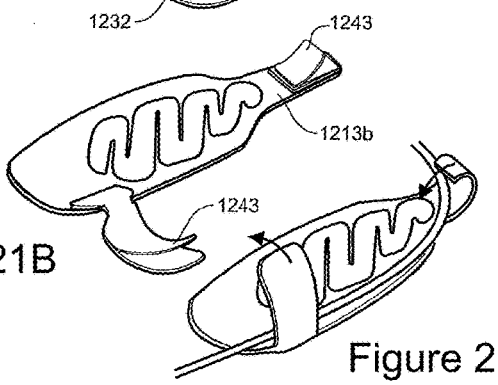
Figure 21B
Figure 21C
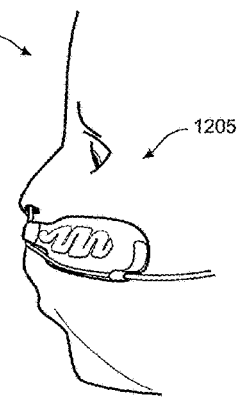
Figure 21D

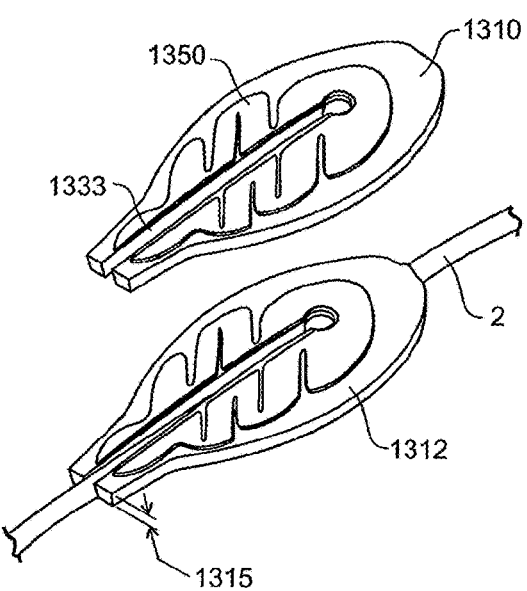
Figure 22A
Figure 22B
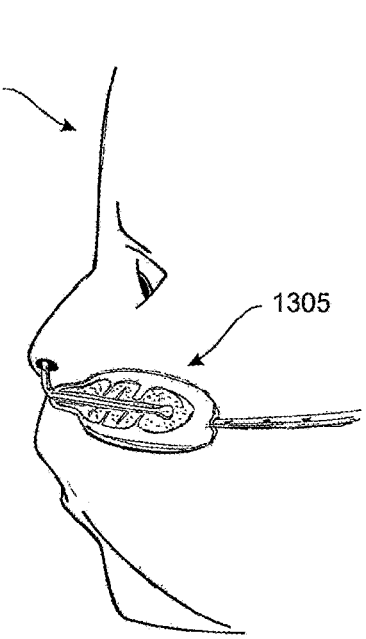
Figure 22C

Figure 23A
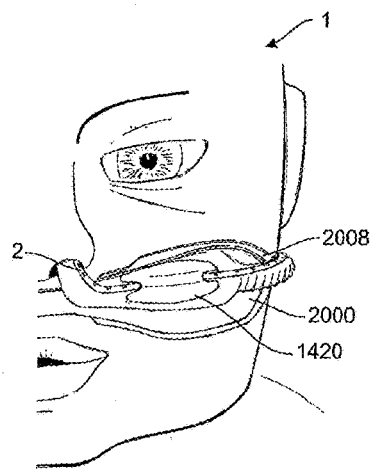
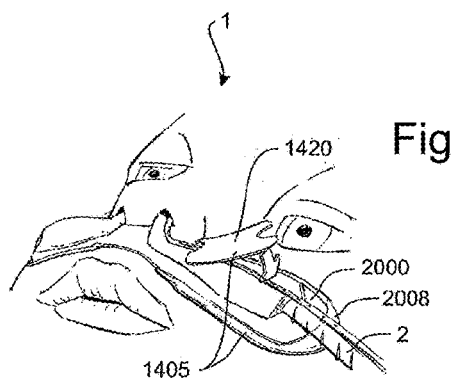
Figure 23B
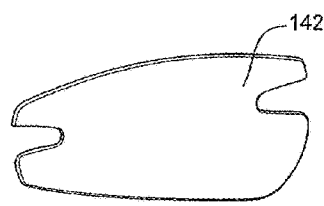
Figure 23C
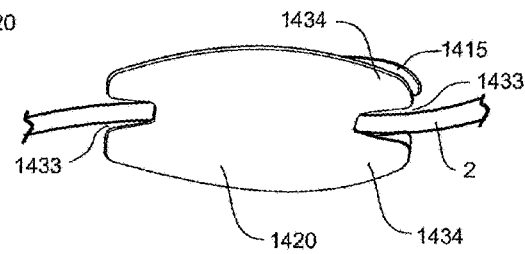
Figure 23D
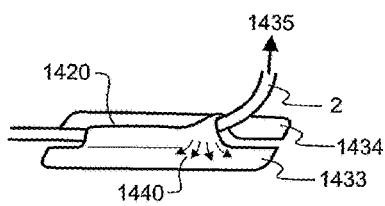
Figure 23E

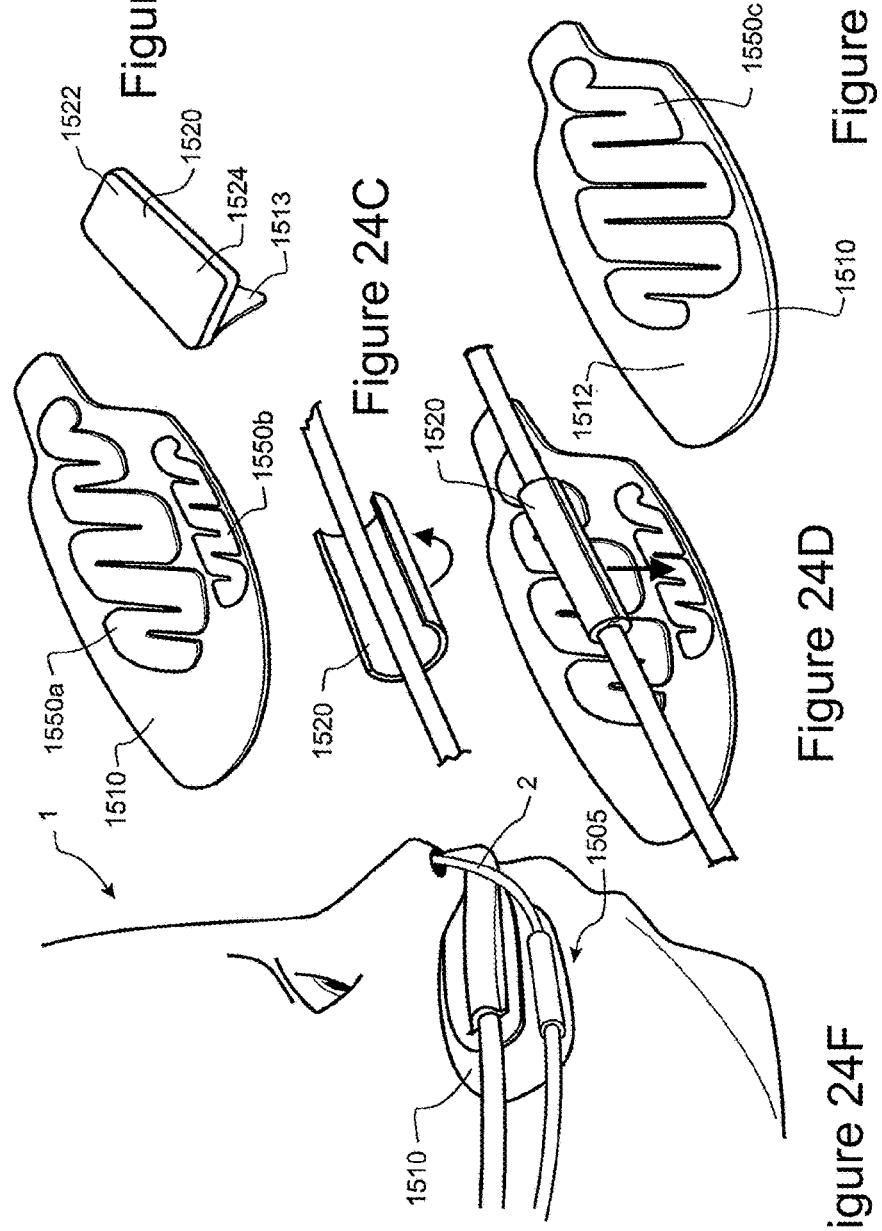

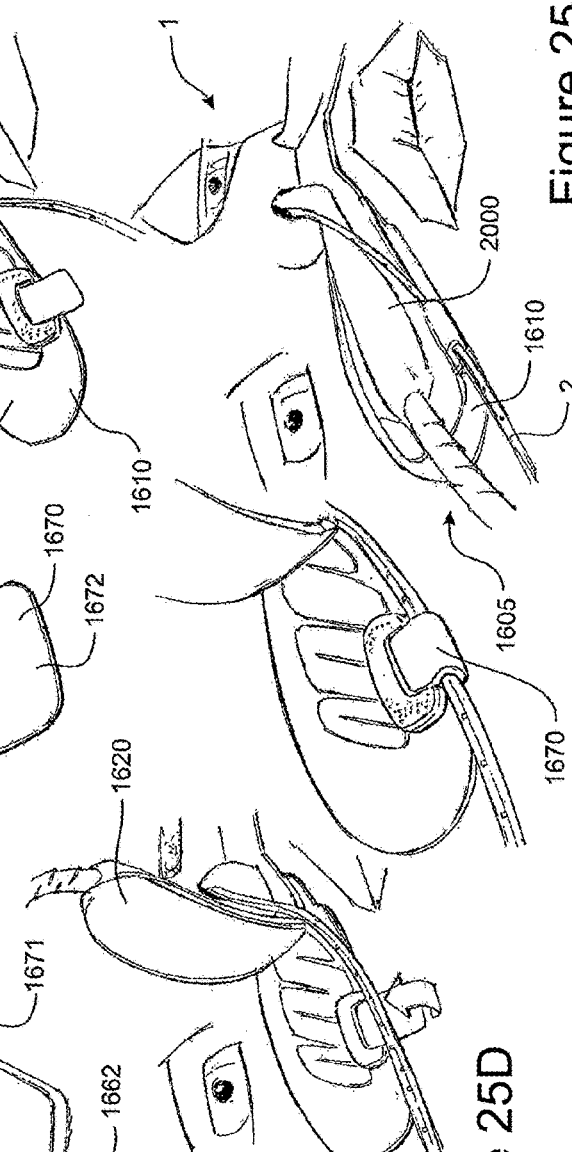

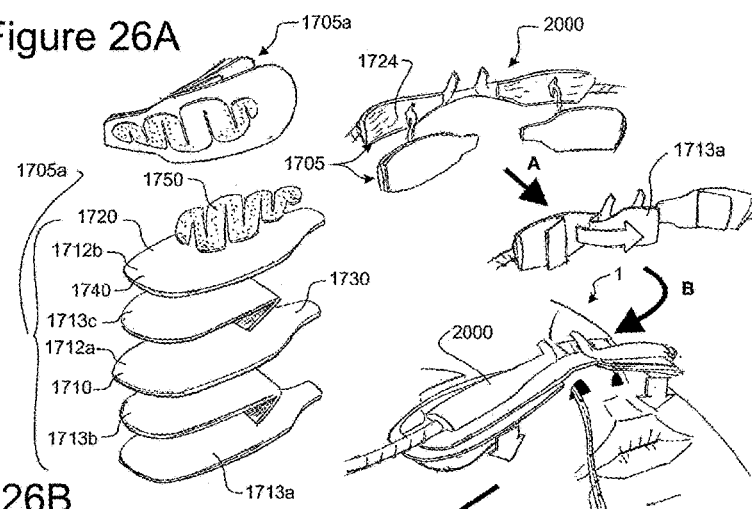
Figure 26A
Figure 26B
Figure 26C
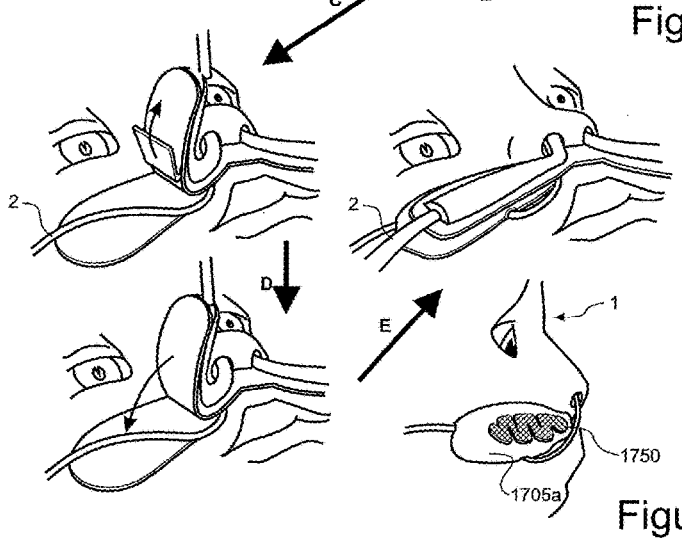
Figure 26D

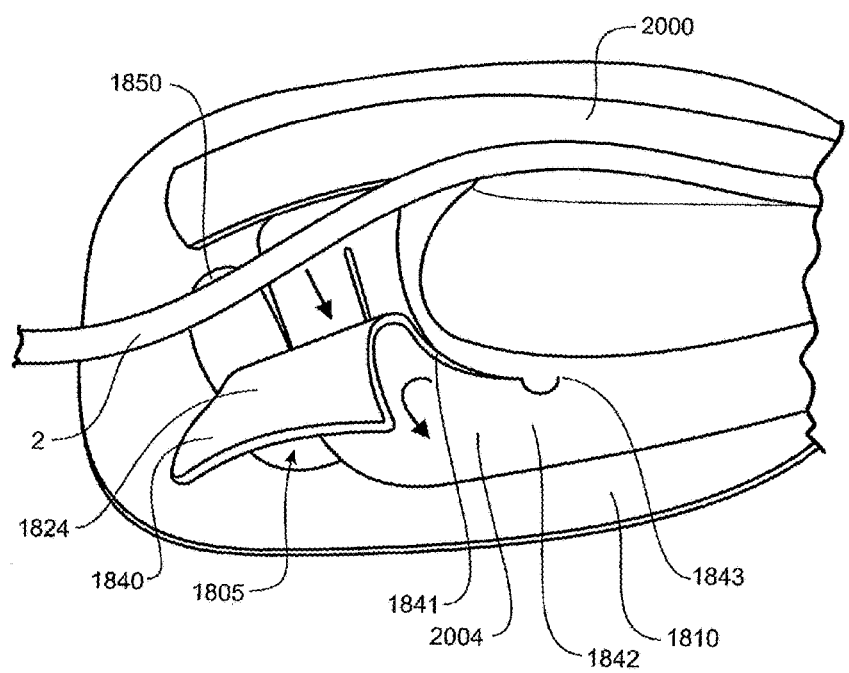
Figure 27A
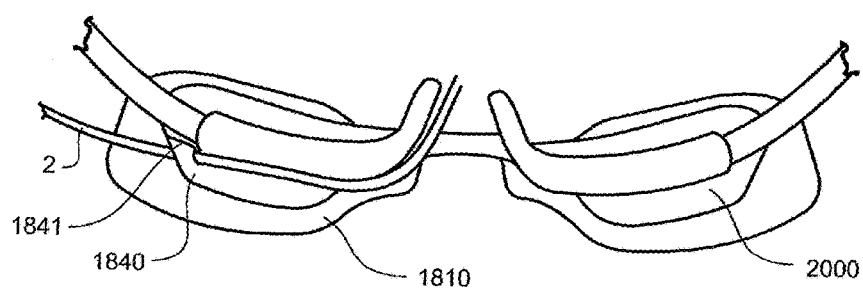
Figure 27B
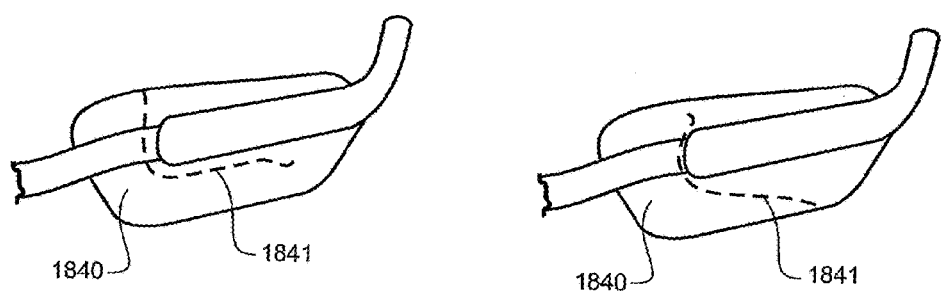
Figure 27C
Figure 27D

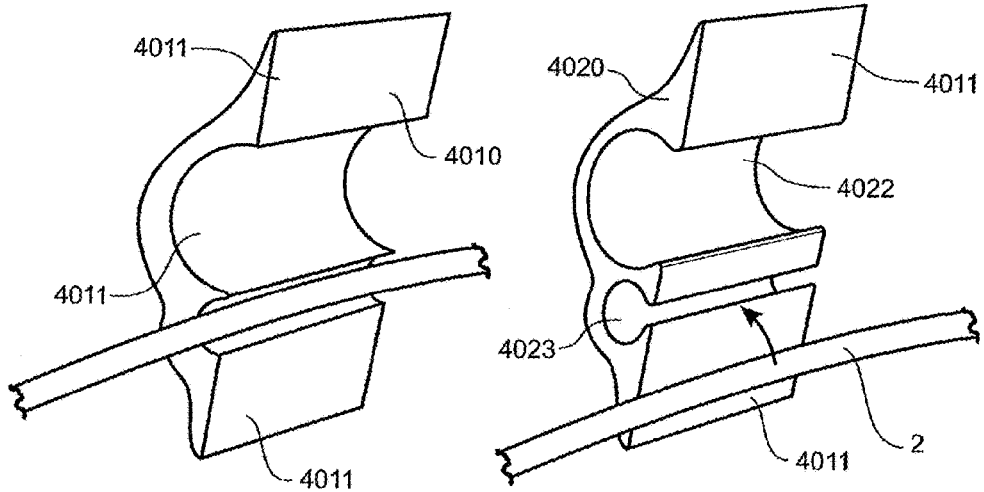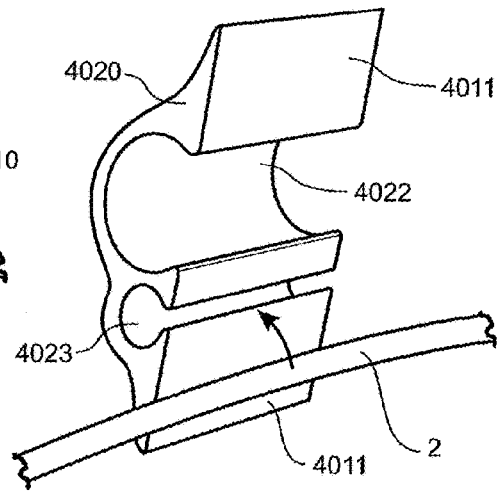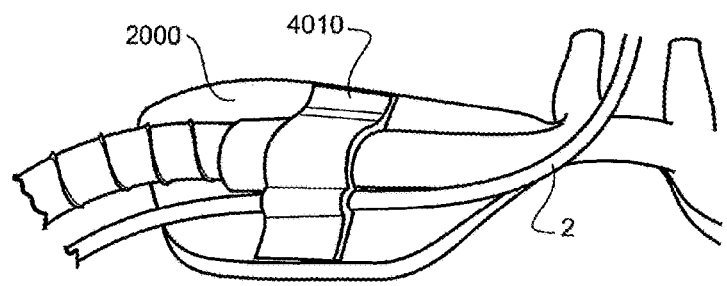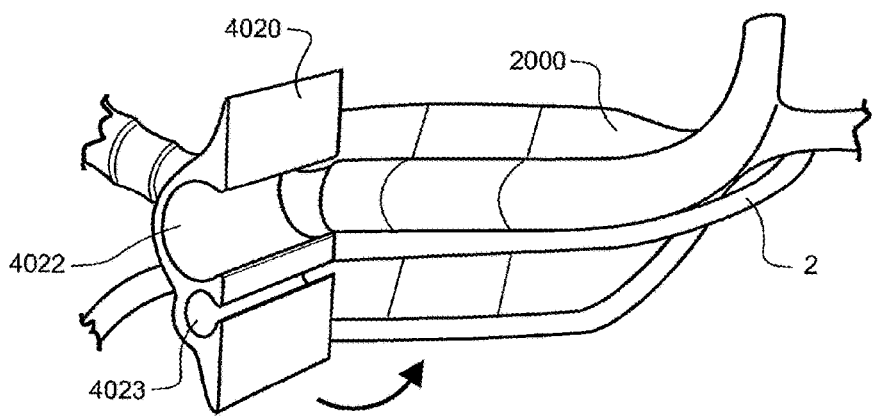

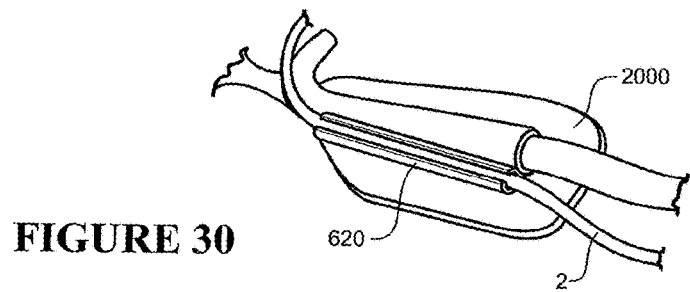
FIGURE 30
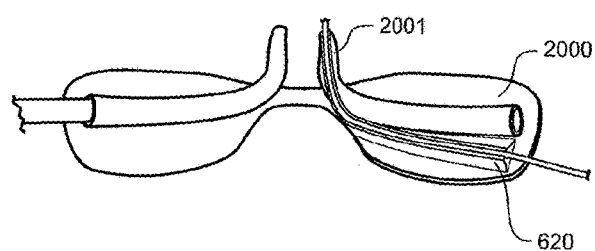
FIGURE 31
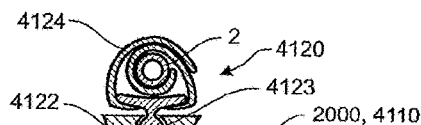
Figure 32B
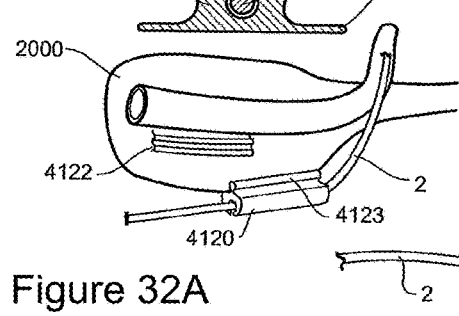
Figure 32A
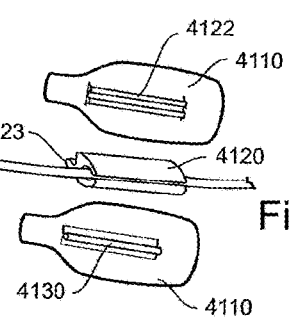
Figure 32C
Figure 32D
Figure 32E

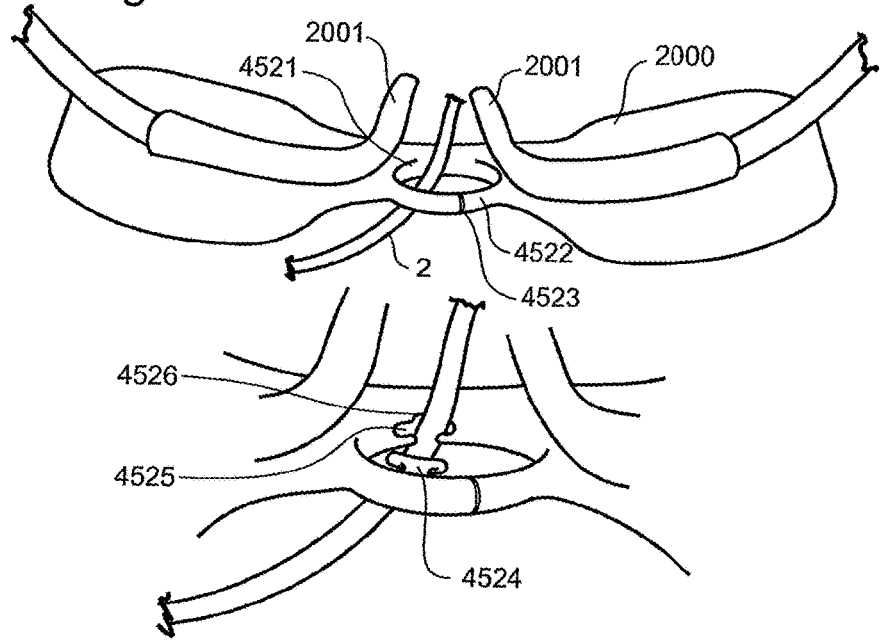
Figure 37A
Figure 37B
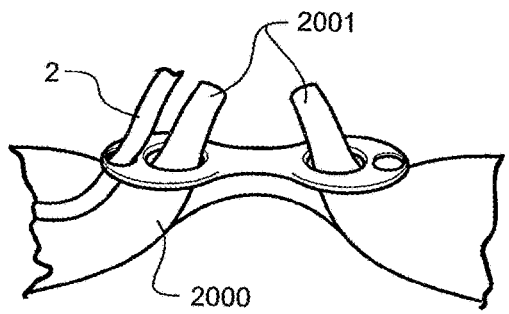
Figure 38A
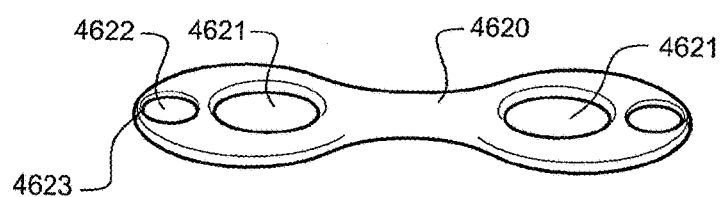
Figure 38B

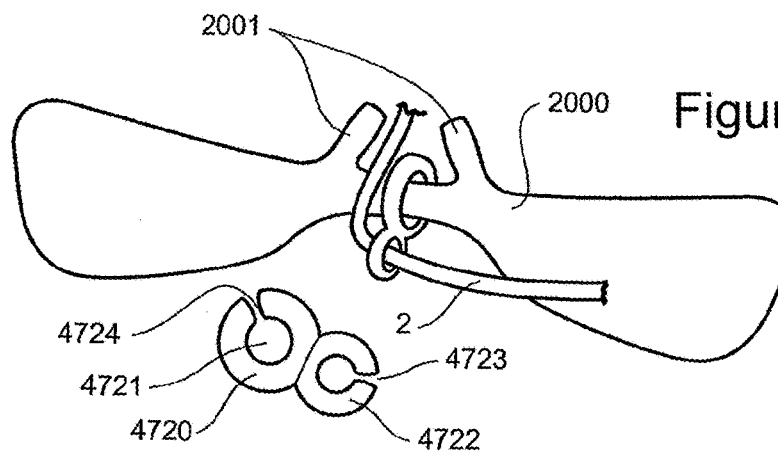
Figure 39B
Figure 39A
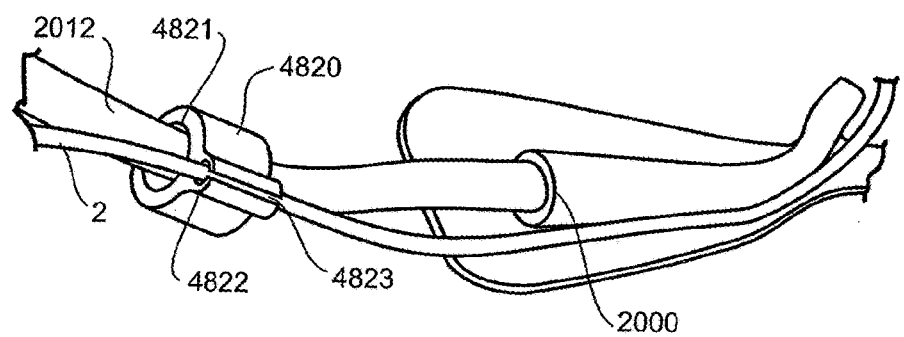
FIGURE 40
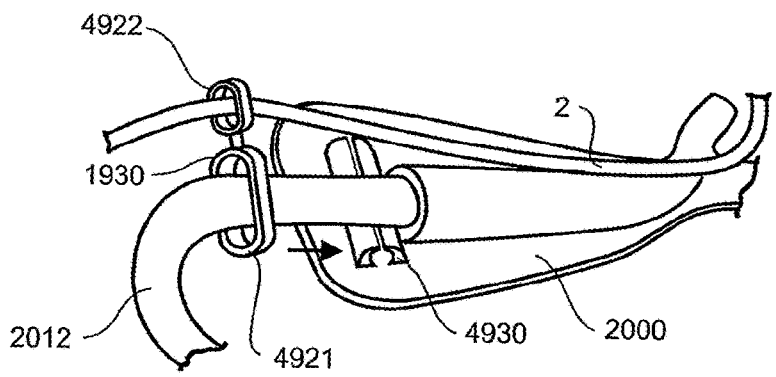
FIGURE 41

TUBE SECUREMENT SYSTEM

CROSS-REFERENCE TO RELATED APPLICATIONS

The present application is a National Phase Application of PCT International Application Number PCT/NZ2013/000069, filed Apr. 17, 2013, which claims priority benefit of U.S. Provisional Application Nos. 61/625,583, filed Apr. 17, 2012, and 61/678,028, filed Jul. 31, 2012, each of which is hereby incorporated by reference herein.

FIELD OF THE INVENTION

The present disclosure generally relates to a system or method for positioning a patient tube, such as a feeding tube, in an operational position for and/or on a user. The disclosure also relates to a system or method for positioning both a patient feeding tube and a patient interface together in an operational position for and/or on a user.

BACKGROUND OF THE INVENTION

Premature babies and paediatric children can require food and or drugs to be delivered to them via a feeding tube. Depending upon the baby/child's individual requirements a different type and size of feeding tube may be used and it may be inserted nasally (naso) or orally (oro). The main types of feeding tubes are nasogastric, nasoduodenal and nasojejunal. A nasogastric tube is inserted though the nostril, down the throat and into the patient's stomach. A nasoduodenal tube is inserted through the nostril, down the throat and through the stomach and into the duodenum, the first part of the small intestine. And a nasojejunal tube is inserted through the nostril, down the throat and through the stomach and into the jejunum, the second part of the small intestine. Generally the size of tube used for infants range from 5 Fr to 10 Fr (diameter 1.67 mm to 3.3 mm).

In use a feeding tube must be adequately secured so that it cannot be pulled out by the baby requiring replacement or repositioning by the nurse/caregiver. Correct checks must be performed to ensure a feeding tube is correctly positioned. For example, if a nasogastric tube is pulled out during feeding, the tube may be repositioned incorrectly in the patient's lungs and not the stomach.

Problems with prior art placement methods for securing a feeding tube to a patients face include pressure sores on the patient's face and pain or damage to facial skin upon removal or replacement of the tube. Further, combined therapy of a feeding tube and a respiratory treatment interface such as a cannula for provision of a flow of respiratory gases via the nares can result in tubes competing for space in the nostril. This can exacerbate pressure sores and irritation to the skin, and feeding tube and breathing tube interference and entanglement can increase the risk for the feeding tube to be pulled out.

Primary considerations for methods for securing a feeding tube in place are the time required for a nurse to prepare and secure the feeding tube, the frequency and effort needed to replace the securement method and/or the feeding tube under normal patient care, the ability to reapply the securement method when patient therapy requires cycling of respiratory treatments, for example between CPAP and nasal high flow therapies, the dexterity required to place the securement method when dealing with an agitated baby, the ability for different nurses to apply and secure the feeding tube in a consistent method with minimal variation, and the amount of force translated into painful tension of the skin when the tube is pulled.

Adhesive tapes or adhesive patches (when repeatedly applied and remove), particularly for infants, create problems. Problems include, but are not limited to, skin irritation from adhesive chemicals (or adhesive removal chemicals, such as solvents) or tape materials (e.g. due to skin sensitivities), damage to user skin due to repeated application and removal of dermal patches or tapes for positioning or re-positioning of the interface for the user.

In the specification where reference has been made to patent specifications, other external documents, or other sources of information, this is generally for the purpose of providing a context for discussing the features of the disclosure. Unless specifically stated otherwise, reference to such external documents is not to be construed as an admission that such documents, or such sources of information, in any jurisdiction, are prior art, or form part of the common general knowledge in the art.

It is an object of the present invention to overcome one or more of the above mentioned disadvantages, or to provide an improved method or system for securing a feeding tube in place on a patients face, or to at least provide the medical profession or users with a useful choice.

SUMMARY OF THE INVENTION

In one aspect, the present invention broadly consists in a securement system for securing a tube to a patient's face, comprising:
  a tube two-part releasable connection arrangement,
  a dermal patch having a patient side and a tube side, the patient side of the dermal patch being attachable to the skin of a user, the tube side of the dermal patch being provided with a first part of the tube two-part releasable connection arrangement, and
  a complementary second part of the tube two-part releasable connection arrangement being attachable or connectable to the tube, in use the first part and second part releasably connected together for affixing the tube to the dermal patch.

Preferably a first part of an interface two-part releasable connection arrangement provided to the tube side of the dermal patch for releasably connecting to a complementary second part of the interface two-part releasable connection arrangement coupled to or formed with a patient interface.

Preferably the securement system comprises a common first part being common to both the tube two-part releasable connection arrangement and the interface two-part releasable connection arrangement, the common first part being both the first part of tube two-part releasable connection arrangement and the first part of the interface two-part releasable connection arrangement.

Preferably the second part of the tube two-part releasable connection arrangement is a pad for wrapping around a portion of the tube.

Preferably the first part of the tube two-part releasable connection arrangement comprises a hook or a loop, and the second part of the tube two-part releasable connection arrangement comprises the other of the hook or loop.

Preferably the securement system comprises an interface patch for attaching to a patient interface, and the second part of the interface two-part releasable connection arrangement provided on a patient side of the interface patch.

In another aspect, the present invention broadly consists in a securement system for securing a tube to a patient interface comprising:

a tube two-part releasable connection arrangement, a patient interface being provided with a first part of the tube two-part releasable connection arrangement, and a complementary second part of the tube two-part releasable connection arrangement being attachable or connectable to the tube, in use the first part and second part releasably connected together for affixing the tube to the patient interface.

Preferably the second part of the tube two-part releasable connection arrangement is a pad for wrapping around a portion of the tube.

Preferably the first part of the tube two-part releasable connection arrangement comprises a hook or a loop, and the second part of the tube two-part releasable connection arrangement comprises the other of the hook or loop.

Preferably the first part of the tube two-part releasable connection arrangement comprises hooks integrally formed with the patient interface, for connection to loops of the second part of the tube two-part releasable connection arrangement attached to the feeding tube.

Preferably the securement system comprises a dermal patch having a patient side and an interface side, the patient side of the dermal patch being attachable to the skin of a user, the interface side of the dermal patch being provided with a first part of an interface two-part releasable connection arrangement for releasably connecting to a complementary second part of the interface two-part releasable connection arrangement coupled to or formed with a patient side of the patient interface.

Preferably the second part of the interface two-part releasable connection arrangement comprises hooks integrally formed with the patient side of the patient interface, for connection to loops of the first part of the interface two-part releasable connection arrangement provided to the dermal patch.

In another aspect, the present invention broadly consists in a securement system for securing a tube to a patient's face, comprising:

a two-part releasable connection arrangement, a dermal patch having a patient side and a tube side, the patient side of the dermal patch being attachable to the skin of a user, the tube side of the dermal patch being provided with a first part of the two-part releasable connection arrangement, and a panel having a tube side, the tube side being provided with a complementary second part of the two-part releasable connection arrangement, in use the panel and the dermal patch being releasably connected by the two-part releasable connection arrangement to hold the tube between the panel and the dermal patch.

Preferably an interface side of the panel is provided with a first part of an interface two-part releasable connection arrangement for connection to a complementary second part of the interface two-part releasable connection arrangement coupled to or formed with a patient interface.

Preferably the panel and the dermal patch are permanently coupled together at a fold region.

Preferably the fold region is approximately parallel to an intended secured position of the tube.

Preferably the fold region crosses over an intended secured position of the tube, the fold region comprising a hole or slot for the tube to extend through.

Preferably the tube side of the dermal patch comprises an adhesive for fixing the position of the tube before the first and second parts of the two-part releasable connection arrangement are engaged.

Preferably the tube side of the dermal patch comprises high surface friction material for contacting the tube.

Preferably the high surface friction material is a rubber material.

Preferably the high surface friction material is a silicone.

Preferably the fold region is perpendicular to the intended secured position of the tube.

Preferably a side of the panel opposite the tube side is adapted for being written on by a pen or pencil or other writing instrument.

Preferably the first part of the two-part releasable connection arrangement comprises a hook or a loop, and the second part of the two-part releasable connection arrangement comprises the other of the hook or loop.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face comprising a clip for releasably receiving the tube, a patient side of the clip attachable to a patient's skin or attachable to or permanently fixed to or integrally formed with one of a dermal patch and a patient interface.

Preferably the clip comprises a recess or channel for receiving the tube, the recess or channel having a lateral dimension similar to or slightly smaller than a diameter of the tube for firmly gripping the tube.

Preferably the clip is located on the dermal patch or the patient interface with the recess in a position intended to be aligned to a patient's nostril.

Preferably the clip is releasable from or permanently fixed to the dermal patch or the patient interface.

Preferably a plurality of clips provided to the dermal patch or the patient interface.

Preferably a first clip is provided at an angle to a second clip, the first and second clips thus arranged to maintain a bend in a tube secured by the first and second clip.

Preferably a surface of the recess for contacting the tube is formed from a rubber material or a material having a high surface friction.

Preferably the clip comprises a primary recess and a secondary recess, the primary recess having a first internal dimension for holding the tube, and the secondary recess having a second internal dimension for holding the tube, and the first internal dimension being larger than the second internal dimension, the primary recess and the secondary recess coupled together via an opening.

Preferably the clips are arranged to route the tube across a patient's face and into the patient's nostril.

Preferably the securement system comprises a dermal patch and a first part of a two-part releasable connection arrangement is provided to a tube side of the dermal patch, the first part adapted to be releasably connected to a second part of the two-part releasable connection arrangement attached to or formed with a patient interface.

Preferably the securement system comprises an interface patch for attaching to a patient interface, and the second part of the two-part releasable connection arrangement provided on a patient side of the interface patch.

Preferably the first part of the two-part releasable connection arrangement comprises a hook or a loop, the second part of the two-part releasable connection arrangement comprising the other of the hook or loop.

Preferably the clip is integrally formed with a patient interface comprising a nasal prong, the clip comprising a channel, the channel extending along the nasal prong.

Preferably the channel extends from the prong and along a body of the patient interface, the channel comprising a bend to direct the tube from the prong and along the body.

In another aspect, the present invention broadly consists in a securement system for securing a tube and a patient interface to a patient's face, comprising:
- a dermal patch having a patient side and a tube side, the patient side of the dermal patch being attachable to the skin of a user, and
- a panel having a tube side and an interface side, the tube side of the dermal patch and the tube side of the panel adapted to be connected together to retain the tube there between, and
- a first part of a two-part releasable connection arrangement provided to the interface side of the panel, the first part adapted to be connected to a second part of the two-part releasable connection arrangement attached to or formed with the patient interface.

Preferably the securement system comprises an interface patch, the interface patch having a patient side and an interface side, and the second part of the two-part releasable connection provided to the patient side of the interface patch, and the interface side of the interface patch adapted to be connected to the patient interface.

Preferably the securement system comprises a second two-part releasable connection arrangement, a first part of the second two-part releasable connection arrangement being provided to the tube side of the dermal patch, and a second part of the second two-part releasable connection arrangement being provided to the tube side of the panel.

Preferably the panel and the dermal patch are permanently coupled together at a fold region.

Preferably the tube side of the panel and the tube side of the dermal patch are adapted to be adhered together to secure the tube there between.

Preferably an intermediate removable protective backing sheet is provided between a portion of the dermal pad and a portion of the panel, a portion of the panel and dermal pad being permanently attached.

Preferably the patient side of the dermal patch is provided with a first removable protective backing sheet removably attached to a first portion of the dermal patch and a second removable protective backing sheet attached to a second remaining portion of the dermal patch.

Preferably the first part of the two-part releasable connection arrangement comprises a hook or a loop, and the second part of the two-part releasable connection arrangement comprises the other of the hook or loop.

Preferably the first part of the second two-part releasable connection arrangement comprises a hook or a loop, and the second part of the second two-part releasable connection arrangement comprises the other of the hook or loop.

In another aspect, the present invention broadly consists in a securement system for securing a tube to a patient's face, comprising:
- a dermal patch having a patient side and a tube side, the patient side of the dermal patch being attachable to the skin of a user,
- a tail portion coupled to the dermal patch for attaching to a tube, the tube positioned on the tube side of the dermal patch, to secure a first portion of the tube,
- a head portion coupled to the dermal patch for attaching to the tube to secure a second portion of the tube.

Preferably the tail portion is adapted for folding at a first fold line to place the tail portion over the tube, a tube side of the tail portion or the tube side of the dermal patch adapted to fix the tube side of the tail portion to the tube side of the dermal patch to secure the first portion of the tube, the head portion being adapted for folding at a second fold line to place the head portion over the tube, a tube side of the head portion or the tube side of the dermal patch adapted to fix the tube side of the head portion to the tube side of the dermal patch to secure a second portion of the tube Preferably the second fold line is arranged at an angle to the first fold line, the head and tail portions holding a bend in the tube between the first and second portions of the tube.

Preferably the tail portion is a panel covering a significant portion of the tube side of the dermal patch, the tail portion being larger than the head portion.

Preferably the head portion is a panel covering a significant portion of the tube side of the dermal patch, the head portion being larger than the tail portion.

Preferably the panel has a slot for assisting the panel to conform to a profile of the tube, the slot extending longitudinally with respect to an intended position of the tube on the dermal patch, the slot extending partway along the panel.

Preferably the tail portion is adapted for being wrapped around at least a full circumference of the first portion of the tube.

Preferably a first part of a first two-part releasable connection arrangement is provided to the tube side of the dermal patch and a second part of the first two part releasable connection arrangement is provided to the tail portion.

Preferably a first part of a second two-part releasable connection arrangement is provided to the tube side of the dermal patch and a second part of the second two-part releasable connection arrangement is provided to the head portion.

Preferably a first part of an interface two-part releasable connection arrangement is provided to an interface side of one of the head portion, the tail portion or the dermal patch, the first part of the interface two-part releasable connection arrangement for releasably connecting to a second part of the interface two-part releasable connection arrangement coupled to a patient interface.

Preferably the securement system comprises an interface patch for attaching to a patient interface, and the second part of the interface two-part releasable connection arrangement provided on a patient side of the interface patch.

Preferably the first part of the two-part releasable connection arrangement comprises a hook or a loop, and the second part of the two-part releasable connection arrangement comprises the other of the hook or loop.

Preferably the first part of the second two-part releasable connection arrangement comprises a hook or a loop, and the second part of the second two-part releasable connection arrangement comprises the other of the hook or loop.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face, comprising:

a dermal patch having a patient side and a tube side, the patient side of the dermal patch being attachable to the skin of a user, a channel formed in the tube side of the dermal patch for receiving the tube, the dermal patch having thickness dimension sufficient to accommodate the channel.

Preferably the channel is curved to align the tube with a patient's nasal passage when the dermal patch is positioned on the patient's face and direct the tube across and above the patient's upper lip.

Preferably the dermal patch comprises notches for providing flexibility to the dermal patch, the channel being formed along a back bone of the dermal patch.

Preferably the securement system comprises a panel for covering the tube side of the dermal patch.

Preferably the panel and dermal patch are adapted to be adhered together.

Preferably the securement system comprises a two-part releasable connection arrangement between the panel and the dermal patch.

Preferably a first part of an interface two-part releasable connection arrangement is provided to an interface side of the panel for releasably connecting to a second part of the interface two-part releasable connection arrangement coupled to or formed with a patient interface.

Preferably a first part of an interface two-part releasable connection arrangement is provided to the tube side of the dermal patch for releasably connecting to a second part of the interface two-part releasable connection arrangement coupled to or formed with a patient interface.

Preferably the securement system comprises an interface patch for attaching to a patient interface, and the second part of the interface two-part releasable connection arrangement is provided on a patient side of the interface patch.

Preferably the dermal patch is formed from a polymer.

Preferably the dermal patch is formed from a polymer bonded to a backing sheet.

Preferably the polymer is a silicone.

Preferably the backing sheet is a hydrocolloid.

Preferably a first part of the two-part releasable connection arrangement comprises a hook or a loop, and a second part of the two-part releasable connection arrangement comprises the other of the hook or loop.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face, comprising:

a dermal patch having a patient side and a tube side, the patient side of the dermal patch being attachable to the skin of a user, a channel for receiving the tube, the channel attached to, or the dermal patch or channel attachable to the other one of the channel or dermal patch, to secure the tube to the dermal patch via the channel.

Preferably the channel comprises notches for providing flexibility to the channel.

Preferably the channel is slotted or open to one side.

Preferably a first part of an interface two-part releasable connection arrangement is provided to the tube side of the dermal patch for releasably connecting to a second part of the interface two-part releasable connection arrangement coupled to or formed with a patient interface.

Preferably the securement system comprises an interface patch for attaching to a patient interface, and the second part of the interface two-part releasable connection arrangement provided on a patient side of the interface patch.

Preferably at least a surface of the channel for contacting the tube is formed from a rubber material or a material having a high surface friction.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face, comprising:

a dermal patch having a patient side attachable to the skin of a user, the dermal patch comprising a wing portion attachable to the tube for affixing the tube to the dermal patch by wrapping the wing portion around the tube so that an initially patient facing side of the wing portion adheres to the tube.

Preferably a first part of an interface two-part releasable connection arrangement is provided to an outer side of the dermal patch for releasably connecting to a second part of the interface two-part releasable connection arrangement coupled to or formed with a patient interface.

Preferably the securement system comprises an interface patch for attaching to a patient interface, and the second part of the interface two-part releasable connection arrangement provided on a patient side of the interface patch.

Preferably the securement system comprises a plurality of transverse notches located along the wing portion.

Preferably the wing portion is detachable from a main portion of the dermal patch for attachment to the patient.

Preferably the dermal patch comprises a notch along a join line between a main portion of the patch and the wing portion.

Preferably the dermal patch comprises a notch along the join line at each end of the join line.

Preferably the patient side comprises an adhesive, the adhesive of the winged portion providing a releasable bond to itself or the tube once wrapped around the tube.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face, comprising:

a dermal patch having a patient side attachable to the skin of a user, the dermal patch comprising a wing portion attachable to the tube for affixing the tube to the dermal patch by wrapping the wing portion around the tube, and a plurality of transverse notches located along the wing portion.

In another aspect, the present invention broadly consists in a securement system for securing a tube to a patient's face, comprising:

a dermal patch having a patient side attachable to the skin of a user, the dermal patch comprising a wing portion attachable to the tube for affixing the tube to the dermal patch by wrapping the wing portion around the tube, and a notch along a join line between a main portion of the patch and the wing portion.

Preferably the dermal patch comprises a notch along the join line at each end of the join line.

In another aspect, the present invention broadly consists in a securement system for securing a tube to a patient's face, comprising:
  a dermal patch having a patient side attachable to the skin of a user, for securing a tube to a patient by placing the dermal patch over the tube on the patient's face, the dermal patch comprising a slot extending longitudinally with respect to an intended position of the tube under the dermal patch, the slot extending partway along the dermal patch.

Preferably a first part of an interface two-part releasable connection arrangement is provided to an interface side of the dermal patch for releasably connecting to a second part of the interface two-part releasable connection arrangement coupled to a patient interface.

Preferably the securement system comprises an interface patch for attaching to a patient interface, and the second part of the interface two-part releasable connection arrangement provided on a patient side of the interface patch.

Preferably the dermal pad has a thickness similar to or greater than a diameter of the tube.

Preferably the first part of the interface two-part releasable connection arrangement comprises a hook or a loop, and the second part of the interface two-part releasable connection arrangement comprises the other of the hook or loop.

In another aspect, the present invention broadly consists in a securement system for securing a tube to a patient's face, comprising:
  a dermal patch having a patient side and a tube side, the patient side of the dermal patch being attachable to the skin of a user,
  a tube pad comprising:
    a patient side and an outer side, the patient side of the tube pad attachable to the tube side of the dermal patch, and
    a tab for wrapping about the tube and adhering to the tube.

Preferably the securement system comprises a cover patch for applying to the tube side of the dermal patch and covering at least a portion of the outer side of the tube pad.

Preferably the securement system comprises a two-part releasable connection arrangement, a first part of the two-part releasable connection arrangement provided to the tube side of the dermal patch and a complementary second part of the two-part releasable connection arrangement provided to the patient side of the tube pad.

Preferably the securement system comprises a two-part releasable connection arrangement, a first part of the two-part releasable connection arrangement provided to the outer side of the tube pad and a complementary second part of the two-part releasable connection arrangement provided to a patient side of the cover patch.

Preferably the securement system comprises a two-part releasable connection arrangement, a first part of the two-part releasable connection arrangement provided to the tube side of the dermal patch and a complementary second part of the two-part releasable connection arrangement provided to a patient side of the cover patch.

Preferably the cover patch is an interface patch having a patient side and an interface side, the interface side attachable to a patient interface.

Preferably the cover patch is a backing of a patient interface attachable to the tube side of the dermal patch or the outer side of the tube pad.

Preferably the first part of the two-part releasable connection arrangements comprises a hook or a loop, and the second part of the two-part releasable connection arrangement comprises the other of the hook or loop.

In another aspect, the present invention broadly consists in a securement patch for securing a tube for treating a patient to a surface comprising:
  an adhesive applied to a side of the patch for adhering the patch to the surface,
  a notch in the edge of the patch at a position intended to be crossed by the tube, the patch comprising a foot either side of the notch.

Preferably the patch is a dermal patch for adhering to the skin of a patient for securing the tube to the patient.

Preferably the patch is a panel for adhering to a patient interface for securing the tube to the patient interface.

Preferably wherein the notch has a depth and the depth is equal to or greater than the diameter of the tube to be secured.

Preferably the depth is at least twice the diameter of the tube to be secured.

Preferably the depth is at least three times the diameter of the tube to be secured.

Preferably the depth is at least four times the diameter of the tube to be secured.

Preferably the patch has two said notches spaced apart on the perimeter of the patch.

Preferably when a force acts on the tube in a direction through the plane of the patch, that force is spread out over an area of the patch including the foot to prevent an edge of the patch crossed by the tube from peeling away from the surface.

In another aspect, the present invention broadly consists in a securement system for securing a tube to a patient's face, comprising:
  a dermal patch having a patient side and a tube side, the patient side of the dermal patch being attachable to the skin of a user, and
  a panel having a tube side and an opposite side, the tube side of the dermal patch and the tube side of the panel adapted to be connected together by an adhesive to retain the tube there between,
  a first portion of the dermal patch and the panel being coupled together at a fold region, and a removable liner being attached to a second portion of one of the dermal patch and the panel, the liner removable for connecting the tube side of the dermal patch and the tube side of the panel together.

Preferably the securement system comprises a second removable liner attached to the patient side of the dermal patch, the second removable liner removable for attaching the patient side of the dermal patch to a patient.

Preferably the second removable liner is attached to a first portion of the patient side of the dermal patch and a third removable liner is attached to a second portion of the patient side of the dermal patch and overlapping a portion of the second removable line, the second portion of the patient side of the dermal patch for attaching near the nostril of the patient.

Preferably a first part of a two-part releasable connection arrangement provided to the opposite side of the panel, the first part adapted to be connected to a second part of the two-part releasable connection arrangement attached to or formed with a patient interface.

Preferably the securement system comprises an interface patch, the interface patch having a patient side and an interface side, and the second part of the two-part releasable connection provided to the patient side of the interface patch, and the interface side of the interface patch adapted for connection to the patient interface.

Preferably the first part of the two-part releasable connection arrangement comprises a hook or a loop, the second part of the two-part releasable connection arrangement comprising the other of the hook or loop.

In another aspect, the present invention broadly consists in a securement system for securing a tube and a patient interface to a patient's face, comprising:
 a patient interface for providing a flow of gases to a patient, the patient interface comprising a backing for positioning on a patient's face,
 a dermal patch having a patient side and an interface side, the patient side of the dermal patch being attachable to the skin of a user, optionally the dermal patch comprising at least a first flap portion attachable to the tube for affixing the tube to the dermal patch by wrapping the flap portion around the tube,
 a two-part releasable connection arrangement for releasably securing the patient interface to the dermal patch, a first part of the two-part releasable connection arrangement provided to the interface side of the dermal patch and a complementary second part of the two-part releasable connection arrangement attached to or formed with a patient side of the backing of the patient interface, and optionally wherein
 the backing comprises a flap for securing over a feeding tube located between the flap and the dermal patch, the flap formed by a slit extending from an edge of the backing to a position inside of a perimeter of the backing.

Preferably the securement system comprises an over patch for securing over the flap and a portion of the dermal patch.

Preferably the first part of the two-part releasable connection arrangement comprises a hook or a loop, and the second part of the two-part releasable connection arrangement comprises the other of the hook or loop.

Preferably said flap is bifurcated or trifurcated.

Preferably said flap is divided into three flap portions, a first flap portion being a substantially central flap portion for connection to at least the septum region of a patient's nose, and a second and third flap portions each of which are substantially adjacent said first flap portion, one of the second or third flap portions for connection to at least a region about or near a nare or nostril of a patient's nose region and the other of the second or third flap portions for connection to the tube.

Preferably said second or third flap portion connected to said tube is a wrapped connection about said tube.

Preferably said flap comprises an adhesive for connection to said patient or said tube.

Preferably said adhesive is a pressure sensitive adhesive.

Preferably said flap secures or retains both a patient interface and said tube in an operational position on a patient.

Preferably said tube is a feeding tube.

In another aspect, the present invention broadly consists in a securement system for securing a tube to a patient interface or a dermal patch comprising:
 a holder, an interface side of the holder attachable to the patient interface or the dermal patch for securing a feeding tube to the patient interface or the dermal patch, optionally the holder comprising at least a first channel or recess (or aperture) for receiving the feeding tube to couple the feeding tube to the patient interface.

Preferably an adhesive is provided to the interface side of the holder for bonding the holder to the patient interface or dermal patch.

Preferably an adhesive is provided to the interface side of the holder for bonding the holder to the patient interface or dermal patch and the tube.

Preferably hook and loop material is provided between the holder and the patient interface or dermal patch.

Preferably the holder is formed from a soft or pliable material.

Preferably the holder is formed from a rigid material for clipping to the patient interface or dermal patch.

Preferably the holder comprises a male or female part or feature and the patient interface or dermal patch comprises a complementary other one of the male and female part, the male and female parts for securing the holder to the patient interface or the dermal patch.

Preferably the holder comprises a recess or channel for receiving the tube, or the channel or recess comprises an aperture for receiving of the tube.

Preferably the recess has a lateral dimension similar to or slightly smaller than a diameter of the tube for firmly gripping the tube.

Preferably a surface of the recess for contacting the tube is formed from a rubber material or a material having a high surface friction.

Preferably the holder comprises a material for wrapping around the tube to couple the holder to the tube.

Preferably the securement system comprises a dermal patch and the complimentary other one of the male and female part is permanently fixed to the dermal patch.

Preferably the material comprises a strap with adhesive on one or both sides for contact by wrapping the material around the tube and onto itself.

Preferably said holder comprises a body, said body including said first channel or recess for connecting, retaining or attaching to said tube, and wherein said body further comprises at least one further channel or recess (or aperture) for connecting, retaining or attaching to said patient interface.

Preferably said first channel or recess is a moulded region of said body receivable of said tube.

Preferably said at least one further channel or recess is a moulded region of said body receivable of a portion of said patient interface.

Preferably said first channel or recess extends substantially orthogonally relative to said at least one further channel or recess.

Preferably said holder is mounted, or mountable, to the patient interface or the dermal patch.

Preferably the first channel or recess is to have an internal dimension smaller than the diameter of the tube when the holder is in an unstressed or un-deformed state for gripping the tube, and said first channel or recess (or aperture) being elastically deformable to increase the internal dimension to be greater than the diameter of the tube to un-grip the tube for adjustment between the tube and the holder.

Preferably the at least one other channel or recess (or aperture) is sized to have an internal dimension smaller than a dimension of the patient interface or a portion of the patient interface when the holder is in an unstressed or un-deformed state for gripping the patient interface, and the at least one other channel or recess (or aperture) being elastically deformable to increase the internal dimension to be greater than the dimension of the patient interface or the portion of the patient interface dimension to un-grip the patient interface or said portion for adjustment between the patient interface and the holder.

In another aspect, the present invention broadly consists in a patient interface comprising a conduit for receiving a feeding tube for securing the feeding tube to the patient interface.

Preferably the patient interface comprises a nasal prong and the conduit comprises an elbow or bend for maintaining a bend in the feeding tube to align the feeding tube with the nasal prong.

Preferably the patient interface comprises a nasal prong and the conduit is provided within a nasal prong.

Preferably the conduit enters the prong at a base of the prong.

In another aspect, the present invention broadly consists in a securement system for securing a tube to a patient interface, the patient interface comprising a nasal prong, the securement system comprising:

a hollow member for receiving the patient interface nasal prong and the tube to couple the tube to the patient interface, the hollow member adapted to fit in the nasal passage of a patient.

Preferably the hollow member is shorter in length than the length of the nasal prong.

Preferably an inside surface of the hollow member comprises a high surface friction material for contacting the tube and the nasal prong.

Preferably the high surface friction material is a rubber material.

Preferably the hollow member is open along its length by a longitudinal slot for inserting the tube laterally into the hollow member.

Preferably the hollow member is formed of a soft material for conforming to the patient's nasal passage.

In another aspect, the present invention broadly consists in a patient interface comprising a ring of material defining an aperture for receiving a tube, and with the ring in an unstressed or un-deformed state, the aperture having an internal dimension smaller than the diameter of the tube for gripping the tube, and with the ring in an elastically deformed state the aperture having an internal dimension greater than the diameter of the tube to un-grip the tube for adjustment between the tube and the patient interface.

Preferably the patient interface comprises a second aperture for receiving the tube, the second aperture loosely capturing the tube to the patient interface.

Preferably the patient interface comprises two nasal prongs and the ring is located between the two nasal prongs.

Preferably the ring comprises a slot for inserting the tube into the aperture.

Preferably the ring of material comprises a clip for securing the tube at the aperture, the clip comprising a male part and a female part formed in the ring opposite the male part, the ring closable on the tube by mating the male and female parts.

Preferably the ring comprises a recess for receiving the tube, the tube lockable in the recess by mating the male part with the female part.

Preferably the ring is adapted to be squeezed by the thumb and forefinger of a user to elastically deform the aperture to release the tube.

In another aspect, the present invention broadly consists in a holder for securing a tube to a patient interface, the holder comprising a first aperture for receiving a part of the patient interface and a second aperture for receiving the tube to couple the tube to the patient interface.

Preferably the patient interface comprises a nasal prong and the first aperture is sized for receiving the nasal prong.

Preferably the patient interface comprises two nasal prongs and the holder comprises two first apertures each said first aperture for receiving a corresponding nasal prong.

Preferably the second aperture is open to a side via a slit.

Preferably the first aperture is open to a side via a slit.

Preferably the patient interface comprises two nasal prongs and the first aperture is sized to receive a portion of the patient interface extending between the two nasal prongs, the first aperture being open to a side via a slit.

Preferably the patient interface comprises two nasal prongs and the holder comprises a plurality of first apertures, each first aperture sized to receive a portion of the patient interface extending between the two nasal prongs or a portion of the patient interface outside of the two nasal prongs, each first aperture being open to a side via a slit.

Preferably the patient interface comprises a breathing tube and the first aperture is sized for receiving the breathing tube.

Preferably the first aperture is sized to allow the holder to slide longitudinally along the breathing tube.

Preferably the material bordering the first aperture comprises a high surface friction material for providing a grip surface to the patient interface.

Preferably the material bordering the second aperture comprises a high surface friction material for providing a grip surface to the tube.

Preferably the first aperture is sized to have an internal dimension smaller than a dimension of the patient interface when the holder is in an unstressed or un-deformed state for gripping the patient interface.

Preferably the first aperture is sized to have an internal dimension smaller than a dimension of the patient interface when the holder is in an unstressed or un-deformed state for gripping the patient interface, and the first aperture being elastically deformable to increase the internal dimension to be greater than the dimension of the patient interface dimension to un-grip the patient interface for adjustment between the patient interface and the holder.

Preferably the second aperture is sized to have an internal dimension smaller than the diameter of the tube when the holder is in an unstressed or un-deformed state for gripping the tube, and the second aperture being elastically deformable to increase the internal dimension to be greater than the diameter of the tube to un-grip the tube for adjustment between the tube and the holder.

Preferably the patient interface comprises a clip for coupling the holder to the patient interface.

Preferably the clip has a male or female part and the holder has a complementary other one of the male and female part for coupling the holder to the patient interface.

Preferably the second aperture are the same size or of a similar size.

Preferably the second aperture comprises a primary recess and a secondary recess, the primary recess having a first internal dimension for holding the tube, and the secondary recess having a second internal dimension for holding the tube, and the first internal dimension being larger than the second internal dimension, the primary recess and the secondary recess coupled together via an opening.

Preferably the holder comprises a base, the first and second apertures formed in the base, and a shield extending from the base, the shield for shrouding or enveloping the tube and the prong.

Preferably the shield extends around the first aperture and the second aperture.

Preferably the shield comprises a longitudinal slit providing an opening for inserting the feeding tube laterally into the shield.

Preferably the shield may having an approximately cylindrical or frusto-conical form extending from the base.

Preferably the holder is adapted to be squeezed by the thumb and forefinger of a user to elastically deform the first aperture to release the patient interface.

Preferably the holder is adapted to be squeezed by the thumb and forefinger of a user to elastically deform the second aperture to release the tube.

In one aspect, the present invention broadly consists in a securement system for securing a tube to a patient's face, comprising a dermal patch having a patient side attachable to the skin of a user, and a tube adhesive side, at least a portion of the tube adhesive side being provided with a first adhesive part of a tube two-part adhesive connection arrangement, and a complementary second tube adhesive part adhesively connectable to the first tube adhesive part on the dermal patch, for affixing the tube to the dermal patch, the second tube adhesive part having higher adhesion/bond strength than the first tube adhesive part.

In some embodiments the second tube adhesive part comprises a panel having a tube adhesive side, the panel and the dermal patch being adhesively connectable to hold a tube between the panel and the dermal patch. In some embodiments the panel is coupled to the dermal patch at a fold region. In other embodiments the panel is a separate component from the dermal patch.

Preferably the first tube adhesive part and the second or tube side adhesive part are provided with a removably attached protective backing sheet or sheets. In a preferred form the first adhesive part is provided with a first backing sheet and the second adhesive part is provided with a second backing sheet. The backing sheet or sheets may extend beyond an external periphery of the adhesive parts to facilitate manual removal of the backing sheets.

Preferably the patient side of the dermal patch is adhesively attachable to the skin of a user, and is also provided with a removably attached protective backing sheet.

The adhesion/bond strength of the first tube adhesive part may enable attachment of the tube thereto and then release and re-attachment of the tube thereto to reposition the tube on the patient side adhesive part. In some embodiments the adhesion/bond strength of the second tube adhesive part is at least two, five, or more times higher than the adhesion/bond strength of the first tube adhesive part. The securement system may also comprise a first part of an interface two-part connection arrangement provided to the tube side of the dermal patch for releasably connecting to a complementary second part of the interface two-part connection arrangement coupled to or formed with a patient interface. The securement system may also comprise a common first part being common to both the tube two-part connection arrangement and the interface two-part connection arrangement, the common first part being both the first part of tube two-part connection arrangement and the first part of the interface two-part connection arrangement.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

As used herein the term "and/or" means "and" or "or", or both.

As used herein "(s)" following a noun means the plural and/or singular forms of the noun. This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

The invention consists in the foregoing and also envisages constructions of which the following gives examples only.

BRIEF DESCRIPTION OF THE DRAWINGS

These and other features, aspects and advantages of the present disclosure will now be described with reference to the drawings of preferred embodiments, which embodiments are intended to illustrate and not to limit the disclosure, and in which:

FIGS. 1A-1F illustrate a securement system for securing a feeding tube in position on a patient's face.

FIG. 2A illustrates the outline of a dermal patch according to some embodiments.

FIGS. 2B to 2R illustrate various embodiments of a fastener substrate portion for securing to the dermal patch of FIG. 2A.

FIGS. 4A-4D illustrate an alternative embodiment of a securement system for securing a feeding tube in position on a patient's face.

FIGS. 4E-4F illustrate an alternative embodiment of a securement system for securing a feeding tube in position on a patient's face.

FIGS. 12A-12C illustrate a securement system for securing both a patient interface and a feeding tube together on a patient's face.

FIGS. 13A-13C illustrate an alternative embodiment of a securement system for securing both a patient interface and a feeding tube together on a patient's face.

FIGS. 14A-14F illustrate an alternative embodiment of a securement system for securing both a patient interface and a feeding tube together on a patient's face.

FIGS. 15A-15E illustrate an alternative embodiment of a securement system for securing both a patient interface and a feeding tube together on a patient's face.

FIGS. 16A-16D illustrate an alternative embodiment of a securement system for securing both a patient interface and a feeding tube together on a patient's face.

FIGS. 17A-17D illustrate an alternative embodiment of a securement system for securing both a patient interface and a feeding tube together on a patient's face.

FIGS. 18A-18I illustrate an alternative embodiment of a securement system for securing both a patient interface and a feeding tube together on a patient's face.

FIGS. 19A-19D illustrate an alternative embodiment of a securement system for securing both a patient interface and a feeding tube together on a patient's face.

FIGS. 20A-20D illustrate an alternative embodiment of a securement system for securing both a patient interface and a feeding tube together on a patient's face.

FIGS. 21A-21D illustrate an alternative embodiment of a securement system for securing both a patient interface and a feeding tube together on a patient's face.

FIGS. 22A-22C illustrate an alternative embodiment of a securement system for securing both a patient interface and a feeding tube together on a patient's face.

FIGS. 23A-23E illustrate an alternative embodiment of a securement system for securing both a patient interface and a feeding tube together on a patient's face.

FIGS. 24A-24F illustrate an alternative embodiment of a securement system for securing both a patient interface and a feeding tube together on a patient's face.

FIGS. 25A-25F illustrate an alternative embodiment of a securement system for securing both a patient interface and a feeding tube together on a patient's face.

FIGS. 26A-26D illustrate an alternative embodiment of a securement system for securing both a patient interface and a feeding tube together on a patient's face.

FIGS. 27A-27D illustrate an alternative embodiment of a securement system for securing both a patient interface and a feeding tube together on a patient's face.

FIGS. 29A-29D illustrate an alternative embodiment of a securement system for securing both a patient interface and a feeding tube together on a patient's face.

FIG. 30 illustrates a securement system for securing a feeding tube to a patient interface.

FIG. 31 illustrates a securement system for securing a feeding tube to a patient interface.

FIGS. 32A-32E illustrate a securement system for securing a feeding tube to a patient interface.

FIGS. 37A-37B illustrate a securement system for securing a feeding tube to a patient interface.

FIGS. 38A-38B illustrate a securement system for securing a feeding tube to a patient interface.

FIGS. 39A-39B illustrate a securement system for securing a feeding tube to a patient interface.

FIG. 40 illustrates a securement system for securing a feeding tube to a patient interface.

FIG. 41 illustrates a securement system for securing a feeding tube to a patient interface.

FIGS. 44A to 44J illustrate an embodiment of a securement system for securing a feeding tube in position on a patient's face: FIG. 44A shows the dermal patch in place on an infant's face securing a feeding tube in place, FIG. 44B is a top view of the product before use, FIG. 44C is a side view of the product before use, FIG. 44D is a cross-section view of the product before use along line I-I of FIG. 44C, FIG. 44E is a side view of the product applied to a patient's skin but before placement of a feeding tube, FIGS. 44F and 44G are side views of the product applied to a patient's skin similar to FIG. 44E, after placement of a feeding tube but before closing of the patch to fix the position of the feeding tube, and FIG. 44H is a side view and FIG. 44I is a top view, both of the product applied to a patient's skin after closing of the patch to fix the position of a feeding tube.

DETAILED DESCRIPTION OF THE PREFERRED EMBODIMENT

Feeding Tube Securement System

Figures 2A, 2B, 2C, 2D, 2E, 2F, 2G, 2H, 2I:
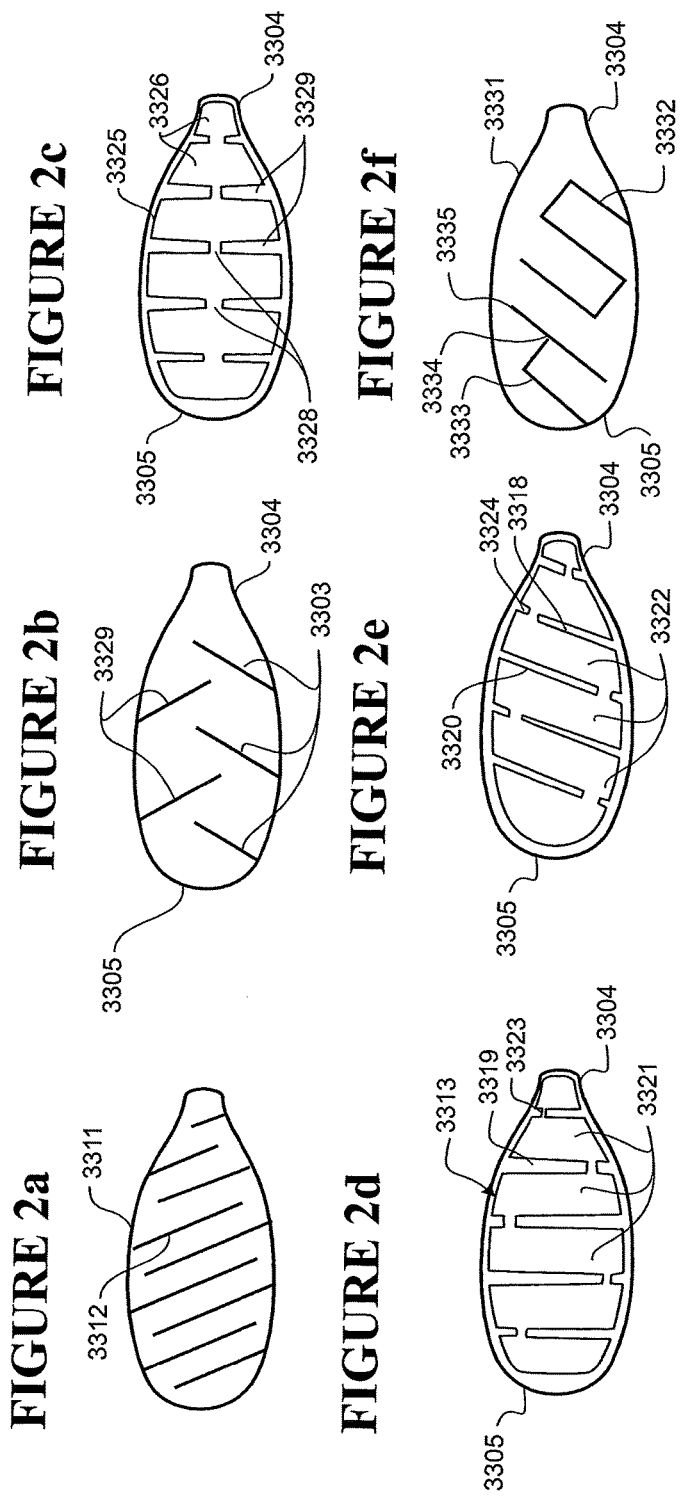

In one aspect, the present invention is a securement system for retaining, holding or securing a feeding tube in position on a patient's face. In one embodiment of the present invention, the securement system comprises a two-part releasable attachment or connection arrangement. The releasable connection arrangement acts between a pair of components that are affixed to the patient and the feeding tube respectively. With reference to FIGS. 1A-1F illustrating one embodiment of a securement system 5, the first component is a dermal patch 10 adhered or otherwise attached to the patient's skin. The dermal patch has a patient side (obstructed from view in FIGS. 1A-1F) that faces the patient's skin and a tube side 12. The patient side of the dermal patch may be attached to the skin of a patient 1 by a dermatologically sensitive adhesive, for example a polyurethane adhesive. Preferably the adhesive of the patient side of the dermal patch is protected for use with a removable backing material 13 that is removed by a nurse/carer immediately prior to positioning on the patient's face, as shown in FIG. 1B. Preferably a range 15 of sizes and/or shapes of dermal patches is provided, as shown in FIG. 1F. The tube side 12 of the dermal patch 10 is provided with a first part 14 of the two-part releasable attachment or connection system. The dermal patch is preferably formed from a hydrocolloid material with an adhesive provided to the patient side.

The second component is a tube patch or pad 20 for attachment to the feeding tube 2. The pad has a tube side 21 and a patient side 22. The tube side is attached to an outer surface of the tube by adhesive. In a preferred embodiment, the pad is adapted to be wrapped around the tube as illustrated in FIG. 1C, so that the patient side 22 of the pad is exposed around at least a portion of the circumference of the tube. Where the tube patch 20 is wrapped around the tube, the patch may or may not be adhered to the surface of the tube. In one embodiment, the tube patch is retained around the tube by overlapping portions of the patch being adhered or otherwise coupled together. For example, hook and loop material may be applied to a portion of the tube and patient sides of the pad so that overlapping portions are releasably coupled together once the pad is wrapped around the tube. The pad is provided with a second part 24 of the two-part releasable attachment or connection system. The patient side 22 of the pad 20 is disposed adjacent the tube side 12 of the patch 10 when the two-part releasable connection is engaged, affixing the tube pad to the dermal patch to fix the position of the tube in place on the patient's face as shown in FIGS. 1D, 1E, and 1A. As shown in FIG. 1A, more than one securement systems 5 may be used to fix a tube to a patients face, for example, as shown one securement system 5 may be used near the patient's nostril and another spaced from the nostril for directing the tube across the patient's face.

The two-part releasable attachment or connection arrangement may comprise a hook and loop material (such as Velcro™), a magnet or an array of magnets disposed on the respective patches with the poles suitably arranged, an adhesive arrangement that is activated when the patches are urged together or another suitable releasable suitable coupling. The tube side of the dermal patch 10 may have one of a hook or a loop material, and the patient side of the pad 20 may have the other of the hook or loop material, such that the dermal patch 10 and the pad 20 are releasably attachable or connectable to each other. The tube 2 with pad 20 applied may be released from the patient without removal of the dermal patch 10.

When we refer to a hook and loop material, we mean any one of a wide variety of area type mechanical fasteners. For example, the Velcro™ product range includes hook and loop product where the hook component includes upstanding nylon hooks (formed as cut loops through a woven backing web) which engage with any complementary loop pile material. The Velcro™ range also includes extruded hook products, typically of a smaller size and which mate with "fluffy" non-woven fiber backing materials. These hook materials are designed to work with a range of loop substrates and in some cases, these hook materials act as loop substrates as well. Other similar systems include the Dual-Lock™ recloseable fastener system from 3M of St Paul, Minn. USA. The common feature of these releasable fastening systems is that they engage at any part of the contact between the two parts of the system. Precise alignment of individual connectors is not required because a multitude of connectors are distributed across the area of the product. A wide range of releasable fastener systems within this field may be used in the releasable attachment system for providing releasable attachment between the dermal patch and the tube pad.

According to some embodiments, the dermal patch 10 is a generally planar pad having a thickness much less than both its width and its length. In some embodiments, the pad has an overall oval shape, but may take other shapes.

The dermal patch includes a first part 14 of the two-part releasable attachment system 5. In some embodiments, the construction of the dermal patch is such that the first part 14 of the releasable attachment system comprises a substrate and multitude of fastener elements (with effective hooks, effective loops or other elements) provided across the area of the substrate. The substrate is secured to the body of the dermal patch. In some embodiments, the substrate is secured by adhesive or by direct bonding during forming of the dermal patch.

In some embodiments, the substrate is smaller in area than the dermal patch and is located on the dermal patch so that it does not reach any edge of the dermal patch. In this way, the edge of the substrate is spread from the edge of the dermal patch all around the perimeter of the substrate.

Dermal Patches

In some embodiments, the substrate for the first part 14 of the two-part releasable attachment system is flexible such that the plane of the substrate may bend to follow a surface that is curved in one direction. However, the substrate is typically not also stretchable to be able to follow a surface curved in two orthogonal directions. However, the pad is of the dermal patch may be stretchable and conformable to surfaces curved in more than one direction such as may be required to conform to the contours of the location of placement on the patient.

According to some embodiments, this difficulty is alleviated by providing a first part 14 of the two-part releasable attachment in a form wherein the portion of substrate is divided by at least one slit or at least one slot into regions such that that different parts of the substrate portion may bend independently and thus the overall form of the substrate portion may deform to substantially match a surface curved in two directions. This will be the case even though the substrate portion is only curved in one direction at any individual location on the substrate portion.

Examples of such forms are illustrated in FIGS. 2B to 2R. The outline of a dermal patch for use in one or more securement system embodiments described herein is illustrated in FIG. 2A. Alternative shaped dermal patches may also be used. The illustrated configuration is particularly useful for the type of shapes where compound curves are most problematic, which is shapes where two or more bends in the substrate are more likely to intersect. Typically, these shapes which are fat, dumpy, stout, short and fat or short and stout, rather than elongate. For example, shapes of this type will have a short perimeter relative to the area. If they have concaves or hollows in the perimeter, then considering a virtual perimeter that is the shortest enclosing path outside the shape, the shapes will exhibit a small ratio of the square of the length of this virtual perimeter to the area of the shape. For example, the lowest ratio is exhibited by a circle at approximately 12.6:1, a square has a ratio of approximately 16:1, a two-by-one rectangle has a ratio 18:1. Whereas more elongated shapes have higher ratios, for example a five-by-one rectangle has a ratio of the square of the length of the perimeter to the area of 29:1. In some embodiments, the improvements that will be described with reference to FIGS. 2B to 2R are advantageously used for patch shapes having a ratio of the length square of the shortest enclosing perimeter to the area inside the perimeter of less than 25. In other embodiments, the improvements that will be described with reference to FIGS. 2B to 2R are advantageously used for releasable attachment substrate portions having a ratio of the length of the square of the shortest enclosing perimeter to the coverage area of the substrate less than 25.

The substrate may be formed as multiple disconnected parts as in the variation of FIG. 2A-2R, however the preferred form is for the substrate to be a single continuous part.

In some embodiments, the releasable attachment substrate portion covers substantially all of the area of the dermal patch 10. In other embodiments, the substrate portion covers most of the area of the dermal patch, for example, 50% or more of the area, 60% or more of the area, 70% or more of the area, or 80% or more of the area of the dermal patch.

Referring to FIG. 2A, in some embodiments, the dermal patch 10 includes a general elliptical or oval body 3602 with a small lateral extension 3600 at one end. In preferred embodiments, this shape has no sharp corners. Rounded or circular corners or curved edges are less readily lifted inadvertently than sharp corners are. In many of the example embodiments of fastener substrate, the fastener substrate includes an overall shape generally matching the overall shape of the dermal patch 10, including extending into the extended portion 3600.

In the illustrated embodiments of FIGS. 2B, 2F, 2G and 2H, the substrate portion does not extend entirely to the edges of the dermal patch 10. Around at least part of the edge, a narrow zone remains between the edge of the dermal patch and the edge of the substrate. This narrow zone may extend around the full perimeter of the substrate. In some embodiments, such as the embodiment of 2B, this zone between the edge of the dermal patch 100 and the edge of the substrate may be broader at some locations than at other locations. For example, in FIG. 2B, a broader zone 3615 is provided at the end intended to be placed further from the nose. This provides for retention of the attachments in the zone nearer the nose, but allows the user to initiate peeling for release of the releasable fastener at the zone further from the nose. A similar arrangement of substrate size and location on the dermal patch could be provided for the other examples of FIGS. 2C to 2R. For example, in each case, the example configuration could be constructed to a smaller area of the dermal patch and located closer to the nasal end of the dermal patch.

The other illustrated embodiments may also be sized to not extend to the edges of the dermal patch. Generally, in the embodiments of FIGS. 2B to 2R, the substrate portion comprises a squat overall shape, which occupies a high percentage of the area within a stretched perimeter (the shortest path enclosing the shape). Generally, the substrate portion is formed as one body, but might be formed of a small number of bodies (for example two bodies) closely interleaved, such as in FIG. 2R. Within this body, the substrate is divided into multiple portions and/or into elongate shapes by at least one slot of slit such that adjacent parts (or sub portions) of the substrate portion are opposed a cross the slit, slot or gap. Depending on the arrangements of slot, slit, gap (or slots, slits or gaps) the substrate may allow the underlying dermal patch to stretch in one or more directions in addition to curving or forming a compound curve. Referring then to the different substrate shapes and configurations, some of the salient features and characteristics will be described.

In each case, certain aspects of the embodiment are described. Many variations may be constructed using these aspects. The aspects of one embodiment may be readily combined with aspects of other embodiments. The arrangements of slits or slots may be oriented in other directions, or may be mirrored or reversed.

The substrate 3603 of FIG. 2B is essentially serpentine. The substrate has an end adjacent the first end 3304 of the dermal patch and a second end adjacent or toward the second end 3305 of the dermal patch. The substrate is formed in a series of switch back loops divided by slits 3306. The slits 3306 may be angled perpendicular to a line between ends 3304 and 3305 or at some other angle. For example, the slots 3306 may be angled such that the upper end of each slit is closer to the first end 3304 than the lower end of each slit, or vice versa that the lower end of each slit is closer to the first end 3304 than the upper end of each slit. There may be at least three slits, at least four slits, or at least five slits. The serpentine shape may provide a shortest uncut path between the first end of the substrate portion and the second end of the substrate portion that is at least twice the actual linear distance between these locations.

The series of slits in the serpentine shape provide alternating portions of the serpentine path, which may bend in different directions to allow the substrate to substantially conform to an underlying compound curve surface. For example, the loop back portions 3307 may bend independently of the straight portions 3308 and the outer surface of the pad of the dermal patch may be allowed to bend to be convex in two orthogonal directions.

Figures 36A, 36B:
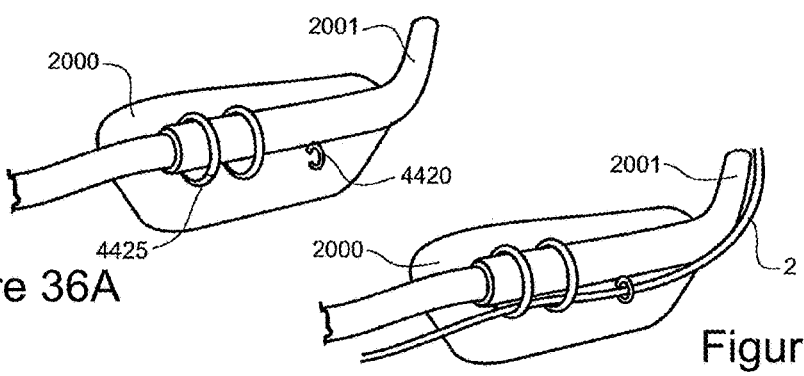
FIGS. 36A-36E illustrate a securement system for securing a feeding tube to a patient interface.
Figures 36C, 36D, 36E:
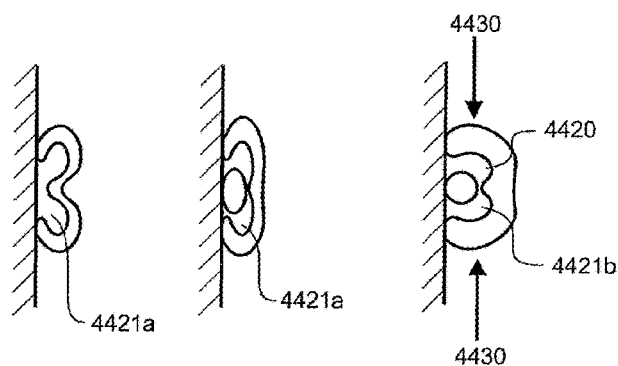

The serpentine shape of the substrate 3603 includes curved or circular corners. The curved or circular corners are less readily lifted, for example, by inadvertent contact, than sharp corners. Similar modifications may be made to any of the embodiments illustrated in FIGS. 36B to 36R.

The substrate portion of FIG. 2C is broadly similar to the substrate portion of FIG. 2B. This substrate portion 3309 is pictured entirely covering the dermal patch. One end fills the first end 3304 of the dermal patch while the other end reaches to the other end 3305 of the dermal patch. A series of alternating slits 3310 reaching from alternating edges of the substrate portion to leave a serpentine body extending between the ends 3304 and 3305. The substrate portion illustrated in FIG. 2C exhibits essentially the same flexing characteristics as the substrate portion of FIG. 2B.

The substrate portion of FIG. 2D shares essentially the same construction with the substrate portion in FIG. 2C except that the substrate portion 3311 in FIG. 2D includes slits 3312 which are further from the nasal end 3304 at the upper ends than the lower ends, whereas the slits 3310 of the substrate portion in FIG. 2C are closer to the nasal end 3304 at their upper ends than at their lower ends.

Other similar serpentine shapes are provided by substrate portion 3313 in FIG. 2G and substrate portion 3318 in FIG. 2H. In each of these cases, narrow slots are provided to separate the substrate portion into a series of adjacent islands 3321 and 3322 respectively along the length of the substrate portion. The slots 3318, 3319 are wider than slits of the previously described embodiments. A series of narrow bridges 3323 and 3324 respectively join between the islands 3321 and 3322 such that the patch forms a continuous serpentine structure. The continuous serpentine structure or the single piece structure improves the ease with which the substrate portion may be located on the dermal patch.

In the embodiment of FIG. 2G, the slots 3319 are oriented substantially orthogonal to a line between ends 3304 and 3305 of the dermal patch. In FIG. 2H, the slots 3320 are oriented with their upper ends closer to the nasal end 3304 than their lower ends—similar to FIG. 2C. In these embodiments, the width of each bridge 3323, 3324 is much smaller than the length of the slots. For example, on average, the width of the bridge portion may be less than 0.2, or less than 0.1 of the average length of the slots.

Other serpentine embodiments will be described below with reference to FIGS. 2M, 2O and 2E.

Another arrangement of substrate including a series of islands connected by bridges is illustrated in FIG. 2F. In this embodiment, the substrate portion 3325 includes islands 3326 and slots 3327. Bridges 3328 connect between the islands. In the illustrated form, the bridges of FIG. 2F are located along the centerline between ends 3304 and 3305. This arrangement might be described as having a central member with a series of leaf portions extending from both sides of the member. In the illustrated embodiment, the slots 3327 extend inward equal distance from each edge. The slots are oriented substantially perpendicular to the line between ends 3304 and 3305. The slots 3327 extend inward from the edge in alignment on opposite sides of the axis. Alternatively, they could be staggered. As with FIGS. 2H and 2B to 2D, the slots 3327 could be oriented at a non-orthogonal angle to the line between ends 3304 and 3305.

In the arrangements of FIGS. 2B, 2C, 2D, and 2F to 2H, the slots or slits are oriented substantially parallel to each other. In the arrangement of FIG. 2E, a series of slits 3329 and 3330 extend in from opposite sides of the substrate portion. In this embodiment, a first group of slits 3329 are oriented in a non-parallel angle with respect to a second group of slits 3330. In particular, in the illustrated embodiment, slits 3329 have their upper end further from the end 3304 of the dermal patch than their lower end, while slots 3330 have their upper end closer to end 3304 than their lower end. In some embodiments, the slits 3329 and 3330 pass the centerline of the substrate portion (the centerline extending from end 3304 to 3305) such that there is no straight linear path between ends 3304 and 3305 that is uncut by a slit 3329 or 3330. The slits 3329 and 3330 form a herring bone pattern.

The embodiments described with reference to FIGS. 2B to 2H have been essentially regular patterns. FIG. 2I illustrates an embodiment with a less regular pattern. In this embodiment, the substrate portion 3331 covers substantially the entire surface of the dermal patch and is divided by an irregular arrangement of slit or slits. For example, slit 3333 extends from one edge adjacent end 3304 in approximately an S shape creating a series of interleaved fingers from either side of the substrate portion 3331. A second slit 3333 extends from an edge of the substrate adjacent end 3305 of the dermal patch. The form of this slit includes a corner or a dog leg and divides at an intersection 3334 into a cross slit 3335. Slits 3332 and 3333 divide the area of the substrate portion 3331 into regions or zones of approximately equal width, with interleaved fingers and long joining portions. In this embodiment, the slits are largely internal to the substrate portion 3331 and only connect to edges of the substrate portion 3331 at two locations.

Similar arrangements of interleaved fingers are apparent in the substrate portion 3336 of FIG. 2J and the substrate portion 3337 of FIG. 2R. In the substrate portion 3336 of FIG. 2J, a single narrow slot 3337 having a small width extends from an edge of the substrate adjacent end 305 in a tortuous path along the length of the substrate portion to end adjacent edge 3304. In this embodiment, the single slot 3337 meets the edge of substrate 3336 at only one location. The slot 3337 divides the substrate portion 3336 into two major portions, each of which includes a series of fingers 3338 and 3339 respectively. The fingers 3339 and 3338 interleave. The location of the slot 3337 and the orientation of long legs 3340 between loop back portions 3341 provides the fingers 3339 and 3338 oriented along a direction that is transverse but at an angle to a line between ends 3304 and 3305.

In an alternative embodiment as illustrated in FIG. 2R, a single serpentine slot 3342 extends from an upper edge of the substrate portion 3337 to a lower edge of the substrate portion 3337. The slot 3342 extends on a serpentine path including straight portions 3343 and loop back ends 3344. This divides the substrate portion 3337 into two laterally separated portions, each of which includes at least one elongate finger 3345. The fingers of one portion are interleaved with the finger or fingers of the other portion. In this embodiment, the interleaved fingers are oriented substantially parallel with a line extending between ends 3304 and 3305.

Another embodiment including a single slot or slit is illustrated in FIG. 2K. In this embodiment, single slit 3346 extends from an edge location adjacent end 3305 in a generally spiral configuration to end at location approximately centered within the substrate portion 3347. The spiral slit 3346 divides the substrate portion 3347 into a single continuous spiral of substrate material. In some embodiments, multiple spirals slits could commence at difference locations around the perimeter of the substrate portion 3347 dividing the substrate portion into multiple interleaved spirals of substrate material.

The embodiment of FIG. 2Q includes substantially continuously curved slits compared with the embodiments of FIGS. 2B to 2J and 2R which use predominately straight slits, albeit in some cases with curved portions. FIGS. 2K to 2P illustrate other substrate portion embodiments with curved slits.

In the embodiments of FIGS. 2K and 2L, the substrate portion 3348 and 3349 respectively are each divided by a plurality of curved slits 3350 arranged, in each case, essentially on the loci of a series of concentric circles. Some of the slits 3350 reach from edges of the substrate portions 3348 and 3349.

Other slots 3351 commence and end within the body of the substrate portion 3348 and 3359. For example, in the substrate portion 3348, slits 3351 each describe an arc through greater than 315° but less than 360°, creating circular and ring-shaped portions within the substrate portion of 3348 which connect to other portions of the substrate portion 3348 via narrow bridges. Slits 3351 in substrate portion 3349 operate similarly to create circular and ring-shaped portions connected by narrow bridges.

In FIG. 2K, the arrangement of slits 3350 and 3351, and in particular the bridges between portions thus divided by the slits is such that tortuous paths of continuous uncut material are provided between end 3305 and end 3304 of the substrate portion and the centre 3352 of the substrate portion. Whereas in FIG. 2L, the arrangement of the curved slits 3350 and the substantially circular slits 3351 is such that the bridges are substantially aligned and more direct paths are provided between at least one end 3305 of the substrate portion and the centre 3352 of the substrate portion.

Another series of embodiments is illustrated in FIG. 2N to 2P. In this series, the substrate portions 3353, 3354, 3355 and 3356 respectively are each divided by a series of narrow curved slots, with each slot extending into the body of the substrate portion from either the upper or lower edge of the substrate portion. The series of curved slots in each substrate portion are arranged in parallel. In some embodiments, the spacing between the curved slots is substantially consistent along the length of the substrate portion. In some embodiments, the slots extend across the majority of the width of the substrate portion, but not entirely across the width of the substrate portion. For example, it may extend across greater than 70%, greater than 80% or greater than 90% of the width of the substrate portion. The slots may have circular corners at their closed end.

In the arrangement in FIG. 2M, the series of slots extend from alternating sides of the substrate portion with slots 3357 and 3358 extending from an upper edge of the substrate portion and slots 3359 and 3360 extending from a lower edge of the substrate portion. This divides the substrate portion into an essentially tortuous length. In this embodiment, the curve of each substrate slot is such that the upper and lower ends of each slot are further away from the end 3304 than the mid portions are.

In the embodiment of FIG. 2N, all four curved slots 3361 extend from the same edge of the substrate portion. This is reminiscent of a comb, with a series of fingers extending in the same direction form a single back bone. As for the embodiment 2N, in this example, the slots are curved such that their upper and lower ends are further from the first end 3304 of the dermal patch than their mid-portions are.

FIG. 2O illustrates a further embodiment similar to the embodiment in FIG. 2N. In FIG. 2O, the curved slots 3362 and 3363 extend from the lower edge and upper edge respectively of the substrate portion. The series of slots 3362 is interleaved with the series of slots 3363, leaving a serpentine or convoluted continuous path along the substrate portion. In the embodiment of FIG. 2O, the upper and lower ends of each curved slot are closer to first end 3304 than are the mid-portions of each curved slot.

Another variation is illustrated in FIG. 2P. In this embodiment, curved slots 3364 will extend from the same edge of the substrate portion. They may extend from the upper edge or the lower edge. The curved slots 3364 are all essentially arranged in a parallel configuration. The curved slots have their upper ends and lower ends closer to the first end 3304 than are their mid-portions.

Alternative Feeding Tube Securement Systems

Figure 3A:
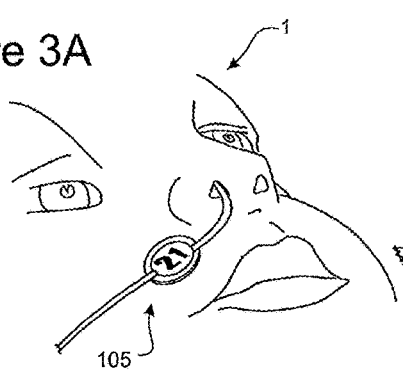
FIGS. 3A-3D illustrate an alternative embodiment of a securement system for securing a feeding tube in position on a patient's face.
Figure 3B:
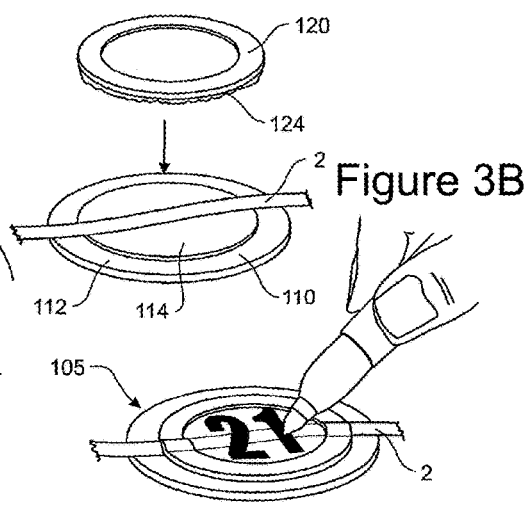
Figure 3C:

An alternative embodiment for a securement system 105 according to an aspect of the present invention is illustrated in FIGS. 3A-3D and comprises a dermal patch 110 and a tube patch or panel 120. In this alternative embodiment, the tube patch is not coupled directly to the tube 2, for example like the embodiment illustrated in FIGS. 1A-1F. In the embodiment of FIGS. 3A-3D, the tube patch 120 and the dermal patch 110 cooperate to sandwich the tube 2 and retain the tube between the tube patch and the dermal patch. The second part 124 of the two-part releasable attachment or connection system is located on the patient side (obstructed from view in FIGS. 3A-3D) of the tube patch, and the first part of the two part releasable attachment or connection system is located on the tube side of the dermal patch. The patient side of the tube patch 120 is disposed adjacent the tube side 112 of the patch 110 when the releasable connection system is engaged to sandwich the tube there between. The first and second parts 114, 124 cooperate to connect the dermal patch and the tube patch together with the tube retained there between. Preferably the first part or substrate 114 of the two-part releasable attachment system is divided by at least one slit or at least one slot into regions as described with reference to FIGS. 2A to 2R. For example, the substrate is illustrated in FIG. 3C in a form similar to that shown in FIG. 2B. The two-part releasable attachment or connection arrangement preferably comprises a hook and loop material (such as Velcro™). Alternatively the two-part connection arrangement comprises an adhesive. For example, the first part or the second part or both comprise an adhesive that releasably affixes the first and second parts together. The adhesive preferably allows the first and second parts to be affixed by a retention force, removed and replaced or affixed together again with the same retention force.

Figure 3D:
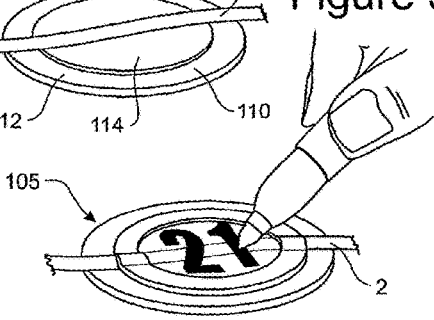

As illustrated in FIGS. 3A and 3D, the outward side or the side opposite the patient side of the tube patch is preferably adapted to be marked with information, for example label or date information, duration of tube insertion, or tube insertion depth, with a pen or other marker.

An alternative embodiment for a securement system 205 according to an aspect of the present invention is illustrated FIGS. 4A-4D. The embodiment of FIGS. 4A-4D comprises a dermal patch 210 for adhering to the skin of the patient, for example as described with reference to the embodiment of FIGS. 1A-1F. Preferably a protective backing 215 may be removed to expose adhesive on a patient side 211 of the dermal patch to stick the patch to the skin, as shown in FIG. 4C. Attached to or integrally formed with the dermal patch is a securement clip 220. The securement clip includes a recess or cavity 218 for receiving the tube 2. The recess is open so that a section of the tube may be pushed in a lateral direction with respect to a longitudinal axis of the tube into the clip. An end of the tube need not be threaded into or through the clip for securement. Preferably the recess has a lateral dimension similar to or slightly smaller than a diameter of the tube so that the tube is gripped firmly by the clip. In one embodiment, the clip is releasable from the dermal patch. For example, a two-part connection system as described with reference to the embodiment of FIGS. 3A-3D may be applied between the clip and the dermal patch. In use a number of securement systems 205 may be placed on the patient's face to hold the tube in position. Alternatively, the securement clip 220 may be attached to or integrally formed with a patient interface for securing the feeding tube to the patient interface. For example the clip has a removable backing liner protecting an adhesive for attaching the clip to a patient interface.

In a preferred embodiment, the clip is molded from a polymer. In one embodiment the clip recess 218 is provided with an adhesive for adhering to the tube positioned in the recess. Alternatively the clip or the recess is formed of a material having high surface friction, for example a rubber. For example, a silicone may be co-molded with the clip to form the surface of the clip recess 218 for interfacing or contacting the tube 2. High friction surface assists with gripping the feeding tube 2 securely.

An alternative clip 240 is also illustrated in FIGS. 4E-4F. The clip 240 comprises a two stage clip-in process. The clip 240 comprises a primary recess or aperture 218a, for example having a circular cross section, and a secondary recess or aperture 218b, for example also having a circular cross section. The primary aperture 218a has a larger diameter or internal dimension than the secondary aperture 218b. The internal diameter of the primary aperture may be slightly larger than the diameter of the feeding tube. And the internal diameter of the secondary aperture may be similar to or slightly smaller than the diameter of the feeding tube. This clip arrangement provides two different holding strengths, the first aperture provides a relatively loose holding force and the secondary aperture provides a relatively tight holding force. The first and second apertures are joined together via an opening 219 common to both first and second apertures. In use, a carer initially inserts the feeding tube into the primary aperture to initially hold the tube 2 'loosely' while further adjustments to the position of the feeding tube may be made. The primary recess provides the carer with a 'third hand', holding the tube in a position that is near to a final desired position. The carer may make further easy adjustment and checking of the feeding tube in the stomach/ intestines with the tube retained loosely or with the primary aperture functioning as a guidance aid. Once the tubing is placed correctly, the carer pushes the tube from the primary aperture to the secondary aperture via opening 219 with a single push to finally secure the feeding tube tightly in the second aperture 218b.

Patient Interface

Figure 5:
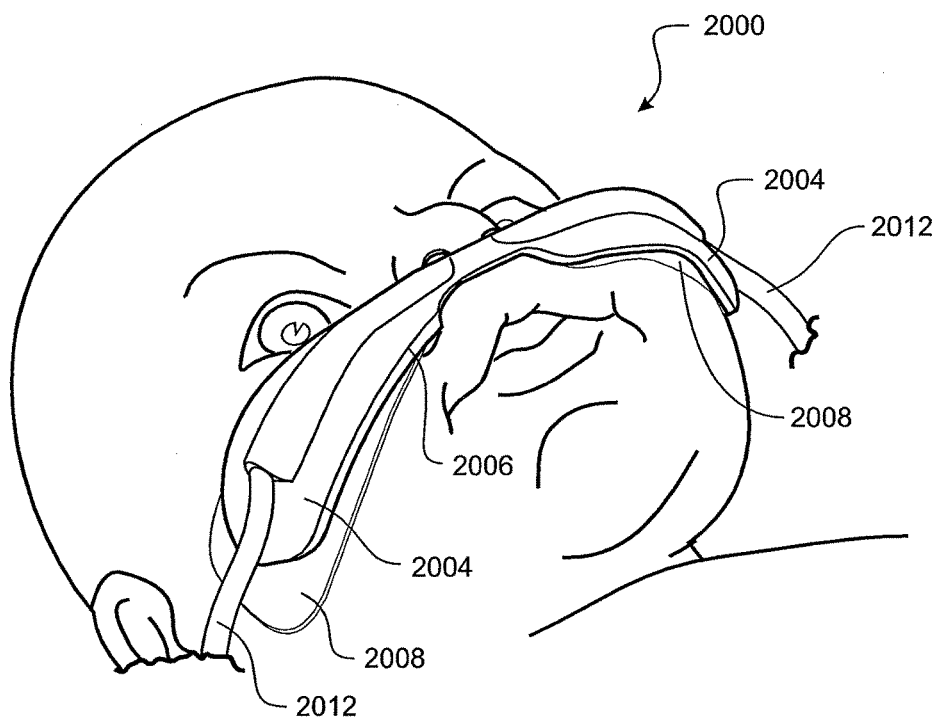
FIGS. 5 and 6 illustrate a nasal cannula and a securement system for securing the nasal cannula in position on a patient's face, the nasal cannula having a backing component comprising a lip.
Figure 6:
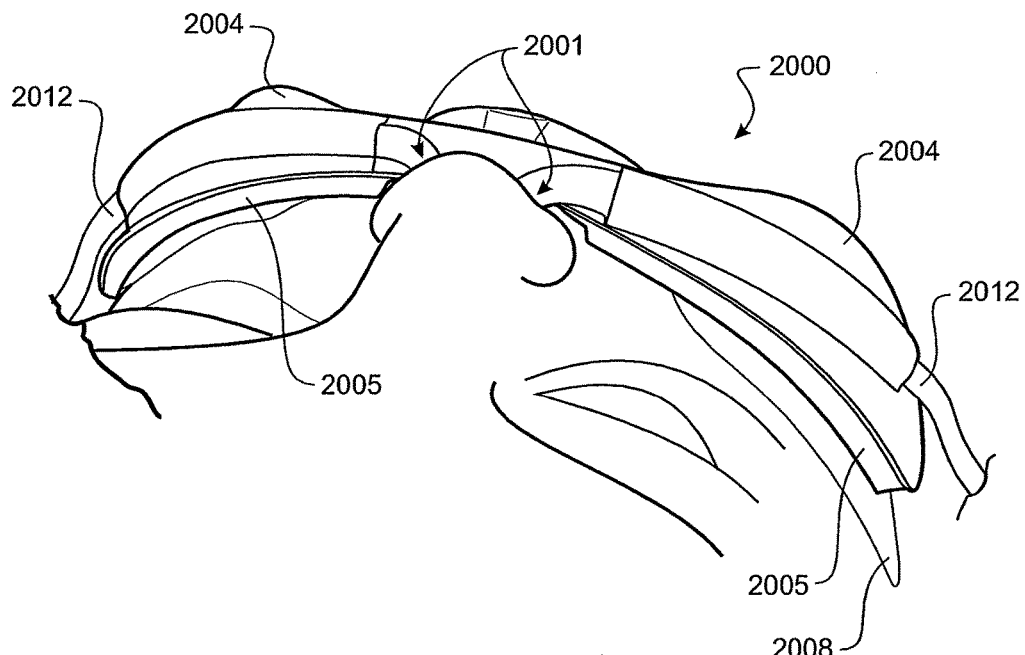

A nasal cannula 2000 is shown in FIGS. 5-11. The illustrated interface 2000 comprises a pair of nasal prongs 2001. Each prong 2001 is coupled to the terminal end of a tube 2012. The other end of the tubes 2012 can be coupled to a supply conduit to interconnect the prongs 2001 to a respiratory system. The tubes 2012 may be coupled to individual supply conduits or alternatively merged (e.g., by a Y coupling or other suitable connector, such as a manifold, for example) to form a single junction with a supply conduit and to facilitate delivery of breathing gases to the interface 2000. An embodiment of the user interface 2000 is illustrated in FIGS. 5 and 6 fitted to an infant.

Each prong 2001 defines a lumen for delivering respiratory gases to a user's nare and incorporates an aperture 2002 or gas outlet for this purpose. The aperture 2002 can be arranged concentrically with a terminal end of the prong so that there is minimal disturbance to flow exiting the prong 2001. A tube end of the prong can be anatomically shaped and/or conform closely to a user's nare, with the terminal end of the prong (i.e., the end incorporating the aperture 2002) being curved away from the septum, for example, to reduce the likelihood of irritation.

Configuration or design of the prongs may take various forms. In one preferred embodiment, the prongs and/or cannula that are over-moulded with the delivery tube may be as described in US Patent Publication No. 2010/0192957, which is hereby incorporated by reference in its entirety.

The tube 2012 to the prong 2001 via gas inlet 2003 fluidly connected to the gas outlet 2002. Preferably the gas inlet is moulded over the tube 2012 to create an integrated component.

The prongs 2001 preferably are held in spaced relation. A backing or harness 2050 is coupled to both prongs 2001 in the illustrated embodiment. The backing 2004 preferably retains the prongs 2001 in fixed spaced relation. Different interface 2000 sizes may be produced to accommodate variations in nasal spacing.

Figure 7:
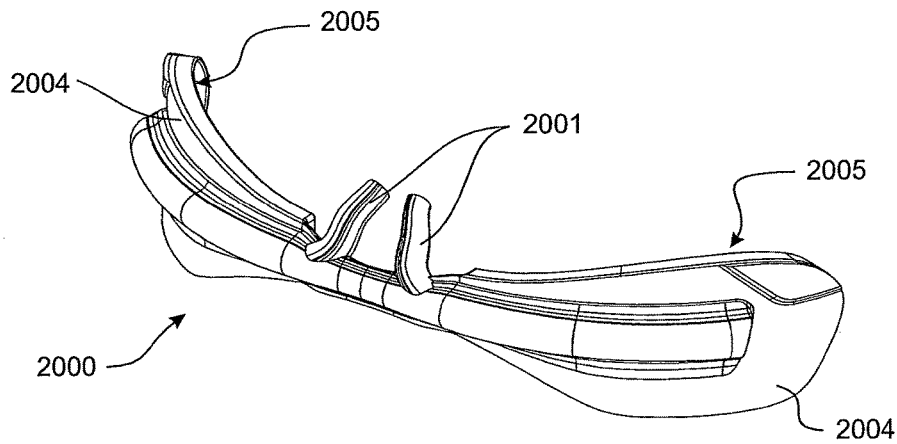
FIG. 7 is a front perspective view of the nasal cannula of FIGS. 5 and 6.
Figure 8:
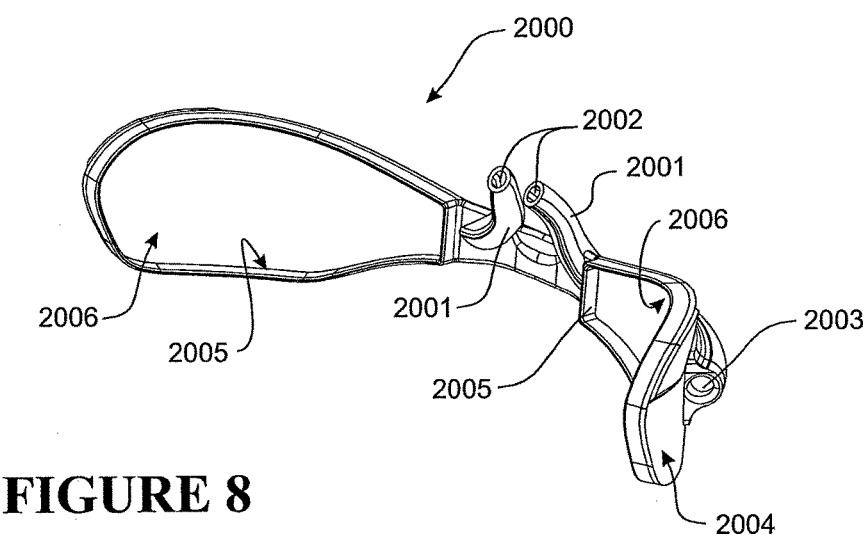
FIG. 8 is a rear perspective view of the nasal cannula of FIGS. 5 and 6.
Figure 9:
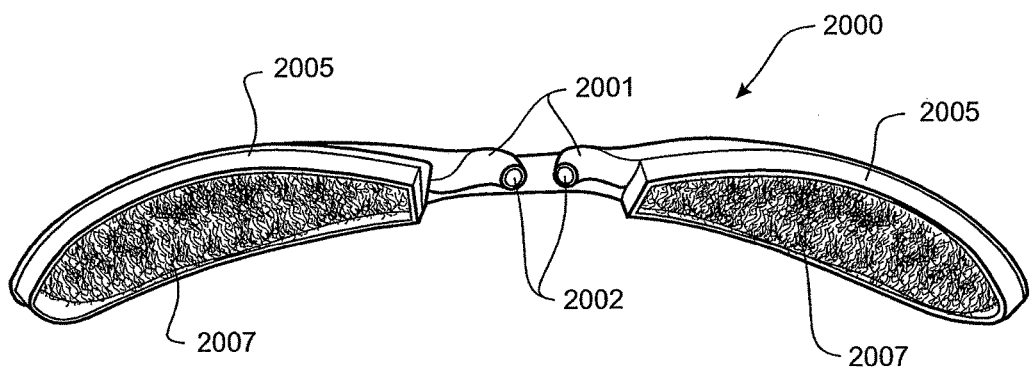
FIG. 9 is a top rear perspective view of the nasal cannula of FIGS. 5 and 6 showing an interface patch on a rear surface of the backing component.

The backing 2004 may take the form of a substantially planar or flat or even contoured (such as a pre-formed curve as shown by FIGS. 7 to 9) backing that is configured to rest on a patient's face. The backing 2004 may generally extend laterally outward from the at least one nasal prong 2001, away from the septum of a user. Such a backing 2004 can assist in operating as a stabilizer of the prong(s) 2001 in the nare(s) of a user.

It will also be appreciated the nasal cannula 2000 can have a pair of prongs 2001 for inserting into the nares of a user, each prong 2001 having an adjacent or associated backing 2004. Where a pair of prongs 2001 is provided, the prongs may be independent of each other, or may utilize a harness to structurally join the prongs together for additional stability.

Patient Interface Securement System

An interface securement system for securing a user interface and/or user interface tubing to a patient is described with reference to 5 to 11. Beneficially, an interface securement system provides for a generally more rapid and improved or simplified ease of installation of a user interface into an operational position on a user. Further, these benefits may also contribute to improved or simplified ease of application of alternative user interfaces or removal of a user interface from a user when cycling a user between different therapies (such as gas treatments, e.g. CPAP or high-flow applications).

Certain user interfaces may be provided specifically for interaction or accommodation with the system of the described embodiments. Alternatively, non-modified user interfaces can be accommodated by the described embodiments and can also be positioned relatively easily and with a minimum of time involved in an installation procedure.

In various embodiments provided by the securement system, such a system may provide for quick location of an interface to a user, and may provide for the secured positioning of the interface.

The ease with which a user interface may be positioned for a user is particularly useful. Providing a system whereby a care giver (e.g. nurse) is able to apply the securement system with a single hand or single handedly, particularly where the interface user is an infant, is particularly advantageous.

A securement system comprising a two-part releasable attachment or connection arrangement is provided to act between a pair of patches that are affixed to the patient and the user interface respectively. The first patch is a dermal patch 2008 that is adhered or otherwise attached to the patient's skin. The dermal patch has a patient side that faces the patient's skin and an interface side that faces the patient interface. The patient side of the dermal patch may be attached to the skin of a user by a dermatologically sensitive adhesive, such as a hydrocolloid.

The second patch is an interface patch 2010. The interface patch 2010 also has a patient side and an interface side. The interface side of the interface patch is adhered or otherwise attached to the backing 2004 of the patient interface. The patient side of the interface patch is disposed adjacent the dermal patch when the securement system is engaged.

A two-part releasable attachment or connection arrangement is provided to releasably attach the interface patch and the dermal patch together. The interface side of the dermal patch is provided with a first part of the two-part releasable attachment or connection system, and the patient side of the interface patch is provided with a second part of the two-part releasable attachment or connection system.

The complementary second part of the two-part releasable attachment or connection system is affixed to the patient side of the interface patch, so that the respective parts of the two-part releasable attachment or connection system are easily engagable when the patches 2007, 2008 are brought together. The interface side of the interface patch is affixed to the patient interface. The interface patch may be integrated with or suitably adhered to the patient interface. In one embodiment, the backing 2004 of the patient interface is the interface patch, the second part 2010 being suitably adhered to the backing 2004.

A part or corner of the user interface patch may include a region that does not attach to the dermal patch. The general purpose of this is to allow a region (or tab) that can be more easily gripped by a user or carer for removing or detaching the interface from the dermal patch. For example, the backing 2004 may also comprise of such a corner region.

The two-part releasable attachment or connection arrangement may comprise a hook and loop material (such as Velcro™), a magnet or an array of magnets disposed on the respective patches with the poles suitably arranged, an adhesive arrangement that is activated when the patches are urged together or another suitable releasable suitable coupling. The interface side of the dermal patch may have one of a hook or a loop material, and the patient side of the user interface patch may have the other of the hook or loop material, such that the dermal and user interface patches are releasably attachable or connectable to each other.

FIGS. 5 and 6 show the cannula arrangement 2000 with backing 2004 in connection with a dermal patch 2008 affixed to a patient's face. A lip 2005 is shown in contact with the dermal patch 2008, thereby providing a barrier to fluids that may otherwise leak to the underside of backing 2004 and the rear surface 2006 to which an interface patch 2007 is retained. As shown, the interface patch 2007 is located in-board of lip 2005.

Figure 11:
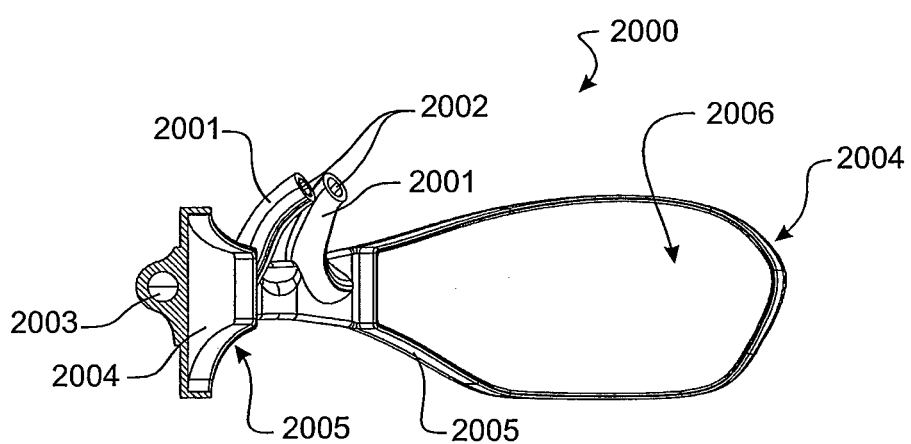
FIG. 11 is a cross sectional view of the nasal cannula arrangement of FIGS. 5 and 6.

As shown by FIGS. 8 and 11, the rear surface 2006 can be initially provided without an interface patch, i.e. the surface 2006 is configured to receive or retain an interface patch 2007. Such user interface patch 2007 may be connected to the rear surface 2006 by an adhesive or other suitable connection. Once the patch is then in position, it is ready to be connected to or receive a dermal patch.

In one form, the interface patch may be one part of a two-part connection system, for example the loops of a hook and loop system. In such an instance, the interface facing surface of a dermal patch 2008 would comprise of hooks that are engageable with the loops of the interface patch. See FIG. 9 illustrating rear surface 2006 retaining an interface patch with loops ready for connection to the hooks of a dermal patch.

Figure 10:
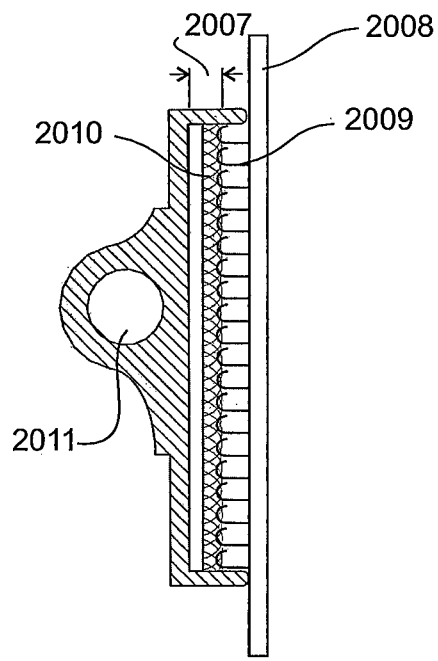
FIG. 10 is a cross sectional view through the nasal cannula of FIG. 9 when the interface patch is in connection with a dermal patch.

FIG. 10 shows a section through a cannula 2000 with the hooks 2009 of a dermal patch engaged with the loops 2010 of a user interface patch. Also shown is lumen 2011 or gas passage pathway for gas being supplied to the gas inlet of the cannula for delivery to the gas outlet 2002 of prongs 2001.

The first part of the two-part releasable attachment or connection system may be adhered to the user interface side of the dermal patch with a suitable adhesive and occupy up to 100% or less than about 90%, or about 85%, or about 75%, or about 60% or about 50% or about 40% or about 30% or about 20% or about 10% of the interface side surface area of the dermal patch.

In addition, in another embodiment, the securement system provides for a first level of securement of a user interface to a user. For example, such a first level of securement may be that as shown by FIG. 10. Where a user requires additional or heightened security of user interface positioning or securement, a secondary level of interface securement can be utilized. Such an additional level may include application of an over patch. Such an over patch may be an adhesive patch and can be installed over the top of the user interface and/or tubing and adhered to a portion of the dermal patch.

Feeding Tube and Patient Interface Securement System

A feeding tube may be used together with a patient interface such as a nasal cannula for providing a flow of respiratory gases to the patent. Combined therapy of a feeding tube and a respiratory treatment interface such as a cannula for provision of a flow of respiratory gases via the nares can result in tubes competing for space in the nostril. To alleviate this problem or help position a feeding tube together with a patient interface, further embodiments of the present invention comprise a securement system that secures both a patient interface and a feeding tube to position both therapy systems together securely.

A securement system 305 for securing both a patient interface and a feeding tube together according to one embodiment of an aspect of the present invention is illustrated in FIGS. 12A-12C. The securement system 305 comprises a dermal patch 310 and a panel 320. The dermal patch 310 and the panel 320 cooperate to sandwich the tube 2 and retain the tube between the panel and the dermal patch. Preferably the dermal patch and the panel are formed from a hydrocolloid material. The first part of a two part releasable attachment or connection system is located on a tube side of the dermal patch. The second part of the two-part releasable attachment or connection system is located on a patient side of the panel. The dermal patch and the panel co-operate to sandwich and secure a feeding tube there between in a similar way to the embodiment of FIGS. 3A-3D. In the illustrated embodiment, the dermal patch 310 and the panel 320 are coupled together at an edge region 313. To couple the first and second parts of the two-part releasable attachment system together, the panel is folded onto the dermal patch at the fold region 313 to bring the patient side 322 of the panel adjacent to the tube side 312 of the dermal patch to couple the first and second parts 314, 324 of the two-part connection system together to capture or sandwich the tube 2 there between. The fold region is located approximately parallel to the intended position of the feeding tube. The panel 320 may be integrally formed with the dermal patch 310.

In addition to the two-part connection arrangement for securing the tube, the securement system 305 further comprises a second two-part connection arrangement for securing a patient interface to the dermal patch. A first part of the second two part connection arrangement is provided to an interface side 321 of the panel. The panel and dermal patch combine to provide a two layered dermal patch with the first part 350 provided to the interface side of the panel for interfacing with a patient interface comprising a second part of the second two part connection arrangement. For example, the layered dermal patch comprising the dermal patch 310 and the panel 320 with first part 350 may replace the dermal patch 2008 for use with the patient interface 2000 comprising the interface patch 2007. In a preferred embodiment, the first part 350 is a substrate divided by at least one slit or at least one slot into regions as described with reference to FIGS. 2A to 2R. For example, the substrate is illustrated in FIG. 12C in a form similar to that shown in FIG. 2B.

An alternative embodiment for a securement system 405 according to an aspect of the present invention is illustrated FIGS. 13A-13C. The embodiment of FIGS. 13A-13C is similar in operation to the embodiment of FIGS. 12A-12C, however, the fold region 413 between the dermal patch 410 and the panel 420 is across or lateral to the anticipated path of the tube 2. In use, the dermal patch is adhered to the skin of the patient. With the panel 420 folded away from the dermal patch, a care giver or nurse passes the tube through a hole or opening 423 near to or at the fold region 413. Once the feeding tube is correctly positioned, the position of the tube is retained by closing the interface patch onto the dermal patch so that the first and second parts 414, 424 of the releasable connection arrangement come into contact to retain the tube between the panel and the dermal patch. In the illustrated embodiment, the first part 414 comprises two parts located either side of an area of the patch intended for placement of the tube 2. Similarly, the second part 424 comprises two parts located either side of an area of the panel intended for placement of the tube 2. One or both of the dermal patch and the panel may comprise an adhesive area to help maintain the position of the tube between the patches. For example, as illustrated in FIG. 13A, an adhesive strip 425 is positioned on the interface patch in an area intended for positioning of the tube. Alternatively, the strip 425 may be a material having a high surface friction, for example, rubber or silicone. For example, a silicone may be co-molded with the patch to form the strip 425. A high friction surface assists with gripping the feeding tube 2 securely between the panel and the dermal patch and reduces the risk of the tube being pulled longitudinally through the securement system 405. In an alternative embodiment, the hole 423 for receiving the tube may be open to one side of the dermal patch and/or the panel, so that the dermal patch may be positioned on the patient after the tube has been inserted in the patient's nostril. The interface patch 420 may be integrally formed with the dermal patch 410.

In addition to the two-part connection arrangement for securing the tube, the securement system 405 further comprises a second two-part connection arrangement for securing a patient interface to the dermal patch. A first part of the second two part connection arrangement is provided to an interface side 421 of the panel. The panel and dermal patch combine to provide a two layered dermal patch with the first part 450 provided to the interface side of the panel for interfacing with a patient interface comprising a second part of the second two part connection arrangement. For example, the layered dermal patch comprising the dermal patch 410 and the panel 420 with first part 450 may replace the dermal patch 2008 for use with the patient interface 2000 comprising the interface patch 2007. In a preferred embodiment, the first part 450 is a substrate divided by at least one slit or at least one slot into regions as described with reference to FIGS. 2A to 2R. For example, the substrate is illustrated in FIGS. 13B-13C in a form similar to that shown in FIG. 2B.

An alternative embodiment for a securement system 505 according to an aspect of the present invention is illustrated FIGS. 14A-14F. The embodiment of FIGS. 14A-14F is similar in operation to the embodiment of FIGS. 12A-12C. The dermal patch 510 and the panel 520 are coupled together at an edge region 513. To couple the first and second parts of the two-part releasable attachment system together, the panel is folded onto the dermal patch at the fold region 513 to bring the patient side 522 of the panel adjacent to the interface side 512 of the dermal patch to couple the first and second parts 514, 524 of the two-part connection system together to capture or sandwich the tube 2 there between. The fold region is located approximately parallel to the axis of the intended position of the tube.

The embodiment of FIGS. 14A-14F further comprises a second two-part connection. A first part 514*b* of the second two-part connection is preferably positioned on the tube side of the dermal patch. A second part 524*b* of the second two-part connection is positioned on a patient side 522*b* of a tab 520*b*.

The first two-part connection system comprising first and second parts 514 and 524 retains a first section or portion of tube 2. The second two-part connection system retains a second section or portion of tube at an angle to the first portion of the tube. The first and second two-part connection arrangements cooperate to maintain a bend or curve in the tube, to assist with alignment of the portion of the tube at the patient's nostril with the patient's nasal passage. Where the tab 520*b* is attached to the dermal patch 510 by a second fold region 513*b*, the second fold region 513*b* is arranged at an angle to the fold region 513 between the panel 520 and the dermal patch 510. In operation, a carer or nurse adheres the dermal patch to the patient's face. Once the tube is correctly positioned, preferably the nurse secures a portion of the tube near the patient's nostril with the second two-part releasable connection arrangement so that the secured portion of the tube is aligned with the patient's nostril. The nurse folds the tab along the fold region 513*b* onto the dermal patch to align the two parts of the second two-part connection arrangement. Securement of the tube near the patient's nostril has the benefit of preventing the patient from using a finger to hook the tube out of the patient's nose. The location of the second part 522*b* functions to reduce the length of exposed tube going into the nares which is often grabbed and pulled out by the patient. The first two-part connection system is then used by the nurse or carer to secure the tube further from the patient's nostril at an angle to the portion of the tube inserted in the nostril, so that the tube is secured to extend away from the patient's nostril and mouth. Preferably the first and second two-part connections maintain an angle of bend in the tube of between 60 and 150 degrees. Preferably the first and second two-part connections maintain an angle of bend in the tube of between 90 and 120 degrees. In one embodiment, the first and second two-part connections are not releasable connections. For example, adhesive applied to one or more of the patient side 522 of the panel, the patient side 522*b* of the tab 520*b*, and the tube side 512 of the dermal patch to bond or stick the panel or the tab or both to the dermal patch to secure the tube 2. The panel 520 or tab 520*b* or both may be integrally formed with the dermal patch 510.

The embodiment illustrated in FIGS. 14A-14F may further comprise a first part (not illustrated) of a third releasable connection arrangement on an interface side 521 of the panel, for connection with a corresponding second part of the third releasable connection system adhered or otherwise fixed to a patient interface.

An alternative embodiment for a securement system 605 according to an aspect of the present invention is illustrated FIGS. 15A-15E. The embodiment of FIGS. 15A-15E comprises a dermal patch 610 for adhering to the skin of the patient, for example as described with reference to the embodiment of FIGS. 4A-4D. Attached to or integrally formed with the dermal patch is a securement clip 620. The securement clip includes a recess or cavity or channel for receiving the tube 2. The recess is open so that a section of the tube may be pushed in a lateral direction with respect to a longitudinal axis of the tube into the clip. An end of the tube need not be pushed through the clip for securement. Preferably the recess has a lateral dimension similar to or slightly smaller than a diameter of the tube so that the tube is gripped firmly by the clip. The recess may be formed from or lined with a material having high surface friction, for example a rubber. For example, a silicone may be co-molded with the clip to form the surface of the recess 618 for interfacing or contacting the tube 2. High friction surface assists with gripping the feeding tube 2 securely. In one embodiment, the clip is releasable from the dermal patch, as shown in FIGS. 15A-15C. For example, a two-part connection system as described previously may be applied between the clip and the dermal patch. Alternatively, the clip may be releasably attached to a patient interface 2000, as shown in FIG. 15D. For example the clip has a removable backing liner 630 protecting an adhesive for attaching the clip to a patient interface, as shown in FIG. 15E. In a further alternative embodiment, FIG. 30 illustrates a patient interface 2000 comprising an integrally formed clip 620. In the embodiment of FIG. 30, the clip has a length many times the diameter of the feeding tube 2. FIG. 31 illustrates a further alternative embodiment comprising a clip or channel integrally formed with a patient interface 2000. The channel 620 is formed to extend along one prong of the patient interface so that the feeding tube is aligned with a patient's nasal passage. The channel extends from the prong and along a body (for example the backing 2004) of the patient interface. The channel comprises a bend to direct the tube from the prong and along the body, so that in use the tube extends from a patient's nostril and across the patients face.

The securement system of FIGS. 15A-15E may comprise more than one securement clips spaced apart on the dermal patch 610. For example, a second clip may be located at position 625 at an angle to the illustrated clip 620 so maintain a bend in the tube 2 to assist with alignment of the tube inserted into the patient's nostril.

The embodiment illustrated in FIGS. 15A-15E may further comprise a first part 650 of a two part releasable connection arrangement on an interface or tube side 612 of the dermal patch, for connection with a corresponding second part of the two-part releasable connection system adhered or otherwise fixed to a patient interface, for example patient interface 2000 described earlier.

An alternative embodiment for a securement system 705 according to an aspect of the present invention is illustrated FIGS. 16A-16D. The embodiment illustrated in FIGS. 16A-16D comprises a dermal patch comprising a thickness dimension sufficient to accommodate a channel 730 for receiving the tube 2. In one embodiment, the channel retains the tube in a similar way as the recess or cavity of the clip of the securement system illustrated in FIGS. 4A-4F and 15A-15E, as shown in FIG. 16B. Alternatively or additionally the tube is retained in the channel by a panel or over patch 720, as shown in FIG. 16D.

The patch 710 may be molded from a polymer 740, for example silicone, bonded to a backing sheet 741 for affixing to a patient, as shown in cross section in FIG. 16C. The backing sheet is preferably a hydrocolloid. Alternatively the dermal patch may be formed from silicone with a dermatologically sensitive adhesive such as a hydrocolloid applied to the patient side of the patch. The channel is open so that a section of the tube may be pushed in a lateral direction with respect to a longitudinal axis of the tube into the channel. An end of the tube need not be threaded through the channel for securement. Preferably the channel has a lateral dimension similar to or slightly smaller than a diameter of the tube so that the tube is gripped firmly by the channel. Preferably the channel is curved at the end that is placed near the patient's nostril to assist with a transition of the tube into the patient's nostril. The thickness dimension of the dermal patch is greater than the thickness of the dermal patch in other embodiments described herein. To allow for flex of the greater thickness dermal patch, notches 731 are provided either side of the channel 730 extending to the edges of the dermal patch. The channel is thus formed along a backbone of the patch. The dermal patch notches are formed in a similar shape to the shape of the substrate described with reference to FIG. 2f. A peelable backing sheet may be removed to expose an adhesive on a patient side of the dermal patch for attaching the patch to the skin of a patient.

Preferably the channel is curved or shaped to maintain a bend in the tube 2 to assist with alignment of the tube with the patient's nostril.

The embodiment of FIGS. 16A-16D may further comprise a panel 720 for attaching to a tube side 712 of the dermal patch 710, as shown in FIG. 16D. In one embodiment the panel 720 is adhered to the tube side of the dermal patch using a suitable adhesive. Alternatively a two part releasable connection system may be used between the panel and the dermal patch to attach the panel. The panel assists with maintaining the tube within channel 730.

The embodiment illustrated in FIG. 16D comprises a substrate or a first part 750 of a two-part connection arrangement on an interface side 721 of the panel 720, for connection with a corresponding second part of the two part releasable connection system adhered or otherwise fixed to a patient interface, for example patient interface 2000 described earlier.

An alternative embodiment for a securement system 805 according to an aspect of the present invention is illustrated FIGS. 17A-D. The embodiment illustrated in FIGS. 17A-17D comprises a dermal patch 810 comprising a guide channel 830 for retaining the feeding tube 2. The guide channel is preferably located at an edge of the dermal patch 810. In use, the dermal patch is adhered to the patient's face. The feeding tube is threaded through the guide channel from one end of the guide channel, as shown in FIG. 17A. Alternatively, the guide channel has a longitudinal slot 832, as shown in FIGS. 17C-17D, or is open to one side so that the feeding tube may be pushed laterally into the guide channel after the tube has been inserted in the patient's nostril. The guide channel is preferably formed from a material having a high surface friction such as a rubber, for example a silicone, for securely holding the tube and reducing the risk of the tube being pulled out of the channel. The guide channel preferably comprises notches 831 for flexibility, as shown in FIGS. 17B-17C. The guide channel is bonded or fixed to the dermal patch. For example, a portion of the dermal patch is wrapped around and bonded to an outer surface of the guide channel. The portion of dermal patch may be wrapped around the guide channel during a manufacturing process. Alternatively, the guide channel and dermal patch may be supplied for use separately as a kit. In use the guide channel may be applied to the tube 2, and then fixed to the dermal patch by, for example, removing a backing cover from an adhesive portion of the dermal patch and wrapping that portion around the guide channel to couple the tube 2 to the dermal patch attached to the patient's face. A backing sheet (not illustrated in FIGS. 17A-17D) is provided to the patient side of the dermal patch for removal immediately prior to affixing the patch onto the user's face. Preferably the backing sheet is in two parts, a first part covering a main portion of the patient side of the dermal patch for affixing the patch to the user's face, and a second part for covering the portion of the patch to be wrapped around the channel 830. Alternatively, an additional patch or tape may be provided for adhering or affixing the channel to the dermal patch.

The embodiment illustrated in FIGS. 17A-17D comprises a substrate or a first part 850 of a two-part connection arrangement on an interface side 812 of the dermal patch, for connection with a corresponding second part of the two part releasable connection arrangement adhered or otherwise fixed to a patient interface, for example patient interface 2000 described earlier.

The embodiment of FIGS. 18A-18I is similar to the embodiment of FIG. 17. The securement system 905 of FIGS. 18A-18I comprises a dermal patch 910 for attaching to the face of a patient. The dermal patch comprises a wing portion 932 for wrapping about the tube 2 once the tube has been correctly positioned in the patient's nostril. A backing sheet (not illustrated in FIG. 18) is provided to the patient side of the dermal patch for removal immediately prior to affixing the patch onto the user's face. Preferably the backing sheet is in two parts, a first part covering a main portion of the patient side of the dermal patch for affixing the patch to the user's face, and a second part for covering the wing portion 932. In use a nurse or carer initially removes the first part of the backing sheet and affixes the dermal patch to the patient's face. Once the nurse is ready to fix the tube to the dermal patch, the nurse removes the second part of the backing sheet for fixing the tube to the wing portion 932. Alternatively, adhesive may be applied to an opposite side 912 of the wing portion for affixing to the tube 2.

The wing portion 932 may extend significantly along the full length (not illustrated in FIGS. 18A-18I) of the patch 910. The wing portion may contain notches 933 along its length to reduce buckling and increase flexibility of the wing, as shown in FIGS. 18C-18D. The notches are arranged transverse to the intended position of a feeding tube on the wing portion. Further, the patch may comprise a notch 934 along a join line between the main portion of the patch 910 and the wing portion 932, as shown in FIGS. 18E-18H. Preferably the patch comprises a notch 934 at each end of the join line. These notches function to reduce or prevent peeling of the edges of the patch from the patient's face at the join line from forces applied to the main portion of the patch by the wing (potentially from pulling and/or flexing of the fixed tubing as illustrated). The wing part may be integrally formed with the patch 910. Alternatively, the wing portion may be separately attached to the patch. In one embodiment, the wing portion may be releasably attached to the patch, for example by an adhesive which can be repeatedly bonded and separated. In one embodiment, the adhesive of the winged portion provides a releasable bond to itself and/or the tube once wrapped onto the tube to allow for tubing adjustment during placement in the stomach/intestines by the nurse/caregiver.

The embodiment illustrated in FIGS. 18A-19I comprises a substrate or a first part 950 of a two-part connection arrangement on an interface side 912 of the dermal patch, for connection with a corresponding second part of the two part releasable connection arrangement adhered or otherwise fixed to a patient interface, for example patient interface 2000 described earlier.

An alternative embodiment for a securement system 1005 according to an aspect of the present invention is illustrated in FIGS. 19A-19D. The embodiment of FIGS. 19A-19D is similar in operation to the embodiment of FIGS. 12A-12C. The dermal patch 1010 and the panel 1020 are coupled together at an edge region 1013. The tube side of the dermal patch or the patient side of the panel, or both, comprises an adhesive for bonding the two patches together. Alternatively, a two-part releasable connection, for example comprising hook and loop connection as described with reference to other embodiments, may be applied between the panel and the dermal patch. In use, the tube 2 is laid over the dermal patch once the dermal patch is affixed to the patient's face. To couple the panel and the dermal patch together and retain the tube 2, the panel is folded onto the dermal patch at the fold region 1013 to bring the patient side 1022 of the panel adjacent to the tube side 1012 of the dermal patch to couple the panel and dermal patch together and capture the tube 2 there between. The panel 1020 may be integrally formed with the dermal patch 1010. The panel may comprise a slot 1033 to allow the panel to flex and conform more easily to the profile of the tube 2. The slot extends longitudinally with respect to the intended position of the tube on the dermal patch and partway along the panel.

The embodiment illustrated in FIGS. 19A-19D comprises a substrate or a first part 1050 of a two-part connection arrangement on an interface side 1012 of the dermal patch, for connection with a corresponding second part of the two part releasable connection arrangement adhered or otherwise fixed to a patient interface, for example patient interface 2000 described earlier.

The dermal patch 1010 comprises a tail portion 1032 to assist with fixing the tube 2 to the securement system 1005. The tail portion 1032 comprises adhesive on a tube side 1012 of the dermal patch 1010 protected by a removable backing sheet. In use the tail is wrapped around the tube to affix the tail portion to the tube. A nurse or carer may initially fix the tube to the dermal patch using the tail portion prior to sandwiching the tube between the panel 1020 and the dermal patch 1010.

An alternative embodiment for a securement system 1105 according to an aspect of the present invention is illustrated in FIGS. 20A-20D. The embodiment of FIGS. 20A-20D is similar in operation to the embodiment of FIGS. 12A-12C, however, the dermal patch 1110 and the panel 1120 are separate items, and are held together to sandwich the tube 2 there between by bonding the panel to the dermal patch. The tube side of the dermal patch or the patient side of the panel, or both, comprises an adhesive for bonding the two components together.

The embodiment illustrated in FIGS. 20A-20D comprises a substrate or a first part 1150 of a two-part connection arrangement on an interface side 1112 of the panel, for connection with a corresponding second part of the two part releasable connection arrangement adhered or otherwise fixed to a patient interface, for example patient interface 2000 described earlier.

An alternative embodiment for a securement system 1205 according to an aspect of the present invention is illustrated in FIGS. 21A-21D. The embodiment of FIGS. 21A-21D is similar in operation to the embodiment of FIGS. 14A-14F. The dermal patch 1210 comprises a head portion 1233 and a tail portion 1232. By comparison with the embodiment of FIGS. 14A-14F, the tail portion 1232 functions in the same way as the panel 520 of FIGS. 14A-14F, and the head portion 1233 functions in the same way as the tab 520b. The tail and head portions are folded onto the interface or tube side of the dermal patch about fold regions 1213 and 1213b. Adhesive on the tail and head portions or on the interface side of the dermal patch fix the head and tail portions to the interface side of the dermal patch to retain the tube 2. Preferably the adhesive surfaces are protected by backing material 1243. The tail retains a first portion of the tube and the head retains a second portion of the tube at an angle to the first portion of the tube. The head and tail portions bonded to the dermal patch cooperate to maintain a bend or curve in the tube, to assist with alignment of the portion of the tube at the patient's nostril with the patient's nasal passage. The first and second fold regions 1213 and 1213b are arranged at an angle to each other. In operation, a carer or nurse adheres the dermal patch to the patient's face. Once the tube is correctly positioned, preferably the nurse secures a portion of the tube near the patient's nostril with the head portion so that the secured portion of the tube is aligned with the patient's nostril. Securement of the tube near the patient's nostril has the benefit of preventing the patient from using a finger to hook the tube out of the patient's nose. The tail is then used by the nurse or carer to secure the tube further from the patient's nostril at an angle to the portion of the tube inserted in the nostril, so that the tube is secured to extend away from the patient's nostril and mouth. Preferably the head and tail portions maintain an angle of bend in the tube of between 60 and 150 degrees. Preferably the head and tail portions maintain an angle of bend in the tube of between 90 and 120 degrees. In one embodiment, releasable two-part connections may be used to secure the tail and the head portions to the interface side of the dermal patch. The head and tail portions may be integrally formed with the dermal patch 1210.

The embodiment illustrated in FIGS. 21A-21D comprises a substrate or a first part 1250 of a two-part connection arrangement on an interface side 1212 of the panel, for connection with a corresponding second part of the two part releasable connection arrangement adhered or otherwise fixed to a patient interface, for example patient interface 2000 described earlier.

An alternative embodiment for a securement system 1305 according to an aspect of the present invention is illustrated in FIGS. 22A-22C. A dermal patch 1310 secures a feeding tube 2 to a patient's face. In use a carer (for example a nurse) removes a protective backing from a patient side of the dermal patch and, having positioned the feeding tube correctly, retains the position of the tube on the patient's face by direct fastening or adhering the dermal patch over the tube. The patient side of the dermal patch may be attached to the skin of a patient over the tube by a dermatologically sensitive adhesive, such as a hydrocolloid. Preferably the dermal patch 1333 comprises a slit or opening to allow the panel to flex and conform more easily to the profile of the tube 2. The embodiment illustrated in FIGS. 22A-22C comprises a substrate or a first part 1350 of a two-part connection arrangement on an interface side 1312 of the dermal patch, for connection with a corresponding second part of the two part releasable connection arrangement adhered or otherwise fixed to a patient interface, for example patient interface 2000 described earlier. The slot accommodates the tube 2 so that the patch presents a relatively flat surface for interfacing with a patient interface. Where the thickness of the patch is similar to or more than the diameter of the tube 2, the tube located in the slot is flush with or below a surface of the patch that interfaces with a patient interface. As indicated by dimension labeled as 1315, FIG. 22B illustrates the patch thickness being similar to the diameter of tube 2 so that the patch lies flat on the patient's skin except for the portion of the patch covering the tube. By accommodating the tube in the slot, the tube does not cause a raised portion in the surface of the patch. A raised portion can reduce the coupling strength between the first part 1350 and a corresponding second part of a two-part releasable connection arrangement, or compromise the fit of a patient interface attached to the patch 1310 into the nares of the patient.

FIGS. 23A-23E illustrates an alternative embodiment for a securement system 1405 for securing both a patient interface and a feeding tube together on a user's face. A two part releasable connection arrangement is provided between an interface patch (hidden from view in FIGS. 23A-23E) attached to or integrated with a patient interface 2000, and a dermal patch 2008 adhered to the skin of the patient as described earlier with reference to FIGS. 5 to 11. The two part releasable connection arrangement affixes the patient interface to the dermal patch attached to the user's face. To couple or fix the feeding tube relative to the user's face, a panel or tube patch 1420 is provided. Once the feeding tube is correctly positioned, a carer attaches the feeding tube to the patient interface by applying the patch 1420 over the feeding tube and adhering the tube patch to the tube and patient interface. In one embodiment, where a user requires additional or heightened security of user interface and tube positioning or securement, a secondary level of interface securement can be utilized by providing a patch 1420 sized sufficiently to be installed over the top of the tube and user interface to be adhered to a portion of the dermal patch attached to the user's skin.

A backing sheet 1415 is provided for protecting an adhesive applied to an interface side of the panel 1420, as shown in FIG. 23D. Preferably the panel 1420 comprises a notch 1433 in the perimeter of the panel at one or two positions. Preferably notches 1433 are provided at two perimeter positions where the tube 2 is intended to cross the perimeter of the patch 1420. A foot 1434 is formed either side of each notch. Where a force is applied laterally to the feeding tube, the force tends to cause the edge of the patch to peel away and lift from the patient interface. Where the patch includes notches 1433, lateral force acting on the tube is resisted by the connection between the feet and the patient interface over the area or length of each foot. The position that the tube crosses the perimeter of the patch is spaced inwards from a distal end of the feet. The force acting on the tube in a direction through the plane of the patch (indicated by arrow 1435) causes a shear force component to act over the area or length of the feet and area of the patch adjacent to the tube. The force is spread or distributed over an area of the patch, as illustrated by arrows 1440 in FIG. 23E. The connection between the patch and the interface is stronger since the force is spread out over a larger area of the patch compared to a patch without notches. Therefore the notches (or feet) result in a higher holding force compared to the same sized patch without notches 1433. The feet prevent the edge of the patch crossed by the tube from peeling away from the patient interface for a given force applied to the tube in a direction through the plane of the patch. The feet provide anchor points or areas spaced from the edge of the patch crossed by the feeding tube. Without notches, lateral force is concentrated at an edge of the patch and the patch tends to lift more easily.

Preferably the notch extends from the edge of the patch inwards by a notch depth that is equal to or greater than the diameter of the tube to be secured (or the length of the feet is equal to or greater than the diameter of the tube). More preferably the notch extends from the edge of the patch inwards by a notch depth at least two or three times the diameter of the tube to be secured. Most preferably, the notch extends from the edge of the patch inwards by a notch depth at least four times the diameter of the tube to be secured. In one embodiment, the notch depth is more than ten times the diameter of the tube to be secured.

The patch 1420 comprising notches 1433 is illustrated in FIGS. 23A-23E for use with a patient interface. Alternatively, the patch 1420 comprising notches 1433 may be used for securing a feeding tube to a dermal patch attached to the skin of a patient. For example, patch 1420 may be used as panel 1120 in the embodiment described with reference to FIGS. 20A-20D. And the patch 1420 comprising notches 1433 may be used for securing a feeding tube directly to the skin of a patient.

An alternative embodiment for a securement system 1505 for retaining, holding or securing a feeding tube in position on a patient's face is illustrated in FIGS. 24A-24F. A dermal patch 1510 is provided for affixing to the skin of a patient 1 as previously described. The dermal patch is provided with a first part 1550*a* of an interface two-part releasable connection arrangement for interfacing to a corresponding second part of the interface two part releasable connection arrangement formed with or attached to a patient interface, for example via an interface patch as described with reference to FIGS. 5 to 11.

The securement system 1505 is further provided with a second two-part releasable connection arrangement. The second two-part releasable connection arrangement is a tube two-part releasable connection arrangement comprising a first part 1550*b* fixed to an interface side 1512 of the dermal patch 1510, and a second part 1520 for attachment to the tube 2. The first part of the interface two-part releasable connection arrangement and the first part of the tube two-part releasable connection arrangement is located side-by-side on the interface side of the dermal patch. The second part of the tube two-part releasable connection arrangement in the illustrated embodiment is a wrap-around pad 1520 previously described with reference to FIG. 1. The tube pad 1520 is provided for attachment to the feeding tube 2. The pad 1520 is attached to an outer surface of the tube by adhesive. In a preferred embodiment, the pad is adapted to be wrapped around the tube as illustrated in FIG. 24, so that a patient side 1522 of the pad is exposed around at least a portion of the circumference of the tube. Where the tube patch 1520 is wrapped around the tube, the patch may or may not be adhered to the surface of the tube. In one embodiment, the tube patch is retained around the tube by overlapping portions of the patch being adhered or otherwise coupled together. For example, hook and loop material may be applied to a portion of the tube and patient sides of the pad so that overlapping portions are releasably coupled together once the pad is wrapped around the tube. The pad 1520 is provided with a second part 1524 of the tube two-part releasable attachment or connection. The patient side 1522 of the pad 1520 is disposed adjacent the tube side 1512 of the dermal patch 1510 when the tube two-part releasable connection is engaged, affixing the tube pad to the dermal patch to fix the position of the tube in place on the patient's face and beside the patient interface as shown in FIG. 24F In an alternative embodiment illustrated in FIG. 24E, a single first part or substrate 1550c is the first part of the tube two-part releasable connection arrangement and the first part of the interface two-part releasable connection arrangement. Both the patient interface 2000 and the tube are coupled to the dermal patch via the second part of the interface two-part releasable connection and the second part of the tube two-part releasable connection and the first part 1550c common to both tube and interface releasable connection arrangements.

Figure 28:
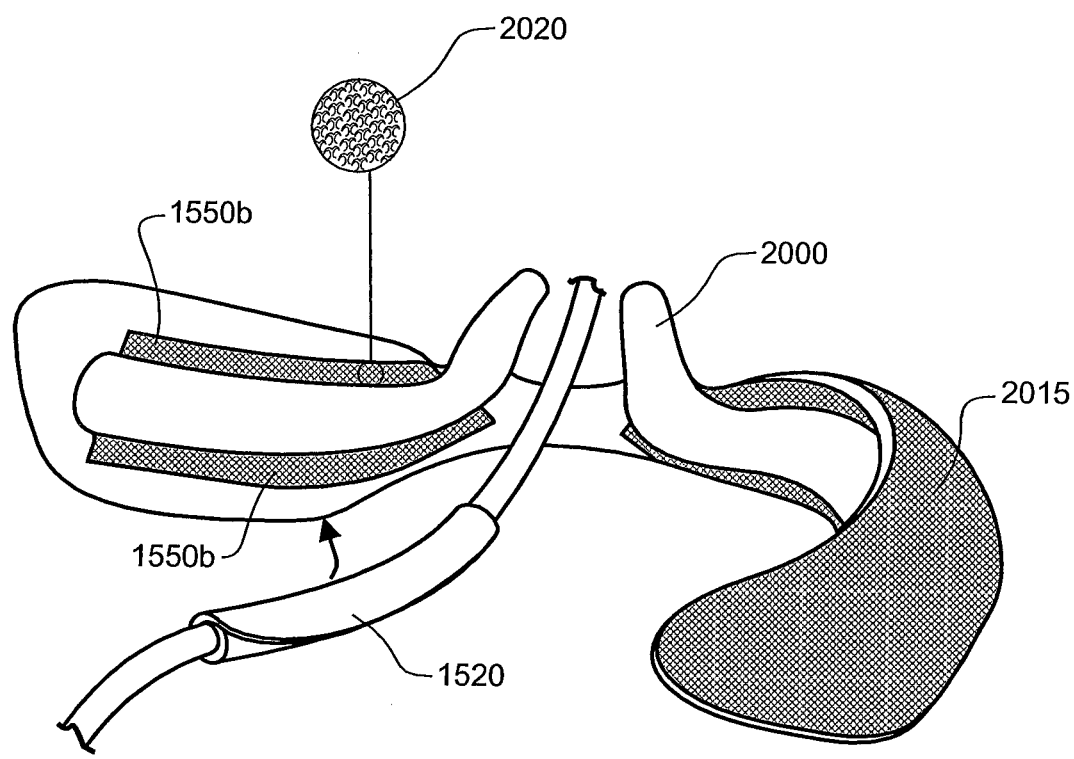
FIG. 28 illustrate an alternative embodiment of a securement system for securing both a patient interface and a feeding tube together on a patient's face.

The embodiment of FIG. 28 is similar to the embodiment of FIGS. 24A-24F. In the embodiment of FIG. 28, the first part 1550b of the tube two-part releasable connection arrangement is fixed to or formed with a front or outer surface of the patient interface 2000. The second part 1520 of the tube two-part releasable connection arrangement attached to the tube. The tube is secured to the front of the patient interface via the first and second parts 1550b and 1520 of the tube two-part releasable connection arrangement.

FIGS. 25A-25F illustrate an alternative embodiment of a securement system 1605 for securing both a patient interface and a feeding tube together on a user's face. A two part releasable connection arrangement is provided between an interface patch 1620 attached to or integrated with a patient interface 2000, and a dermal patch 1610 adhered to the skin of the patient as described earlier with reference to FIGS. 5 to 11. The two part releasable connection arrangement affixes the patient interface to the dermal patch attached to the user's face. To couple or fix the feeding tube relative to the user's face, a tube pad 1660 is provided. The tube pad comprising a patient side (obscured from view in FIGS. 25A-25F) and an interface side 1661. A second part 1662 of a two-part releasable connection arrangement is provided on the patient side of the tube pad 1660. The second part 1662 corresponds with a first part 1614 of an interface two-part releasable connection arrangement provided on the interface side 1612 of the dermal patch 1610. The interface side of the tube pad 1660 is provided with a first part 1663 of a two-part releasable connection arrangement. The first part 1663 corresponds with a second part 1624 of an interface two-part releasable connection arrangement provided on the patient side 1622 of the interface patch 1620. Further, the tube pad comprises a tab 1670 for adhering to the tube 2. A tube side of the tab 1670 is provided with adhesive preferably protected with a removable backing sheet 1671.

In use, a carer or nurse affixes the dermal pad to the patient's skin. The feeding tube and the patient interface are correctly positioned. The tube pad is attached to the dermal pad via the two-part releasable connection arrangement comprising first part 1614 applied to the dermal pad and second part 1662 applied to the tube pad. With the feeding tube correctly positioned, the feeding tube is retained by the feeding tube pad tab 1670. The tab 1670 is wrapped around the tube so that the adhesive of the tab 1670 fixes the tube to the tab. With the tube retained by the tube pad, the patient interface is affixed to the dermal patch over the tube pad. With the patient interface fixed in position on the dermal patch, the tube pad is spaced between the patient interface and the dermal patch. The patient interface is affixed to the dermal patch via the two-part releasable connection arrangement comprising first part 1614 applied to the dermal pad and second part 1624 applied to the patient interface or to the interface patch 1620 fixed to the patient interface 2000. The second part 1624 is releasably connected to both of the first part 1614 adhered to the dermal patch 1610 and the first part 1663 adhered to the tube pad. With the tab 1670 wrapped around the tube to secure the tube 2, preferably an end 1672 of the tab is positioned between the interface patch 1620 and the dermal patch 1610. To accommodate the end 1672 of the tab, preferably the first part 1663 on the interface side of the tube pad comprises a recess 1674. With the tab 1670 wrapped around the tube 2 and with the end of the tab positioned in the recess 1674, the end of the tab is covered by the interface patch with the interface patch affixed to the dermal patch via the two-part releasable connection comprising parts 1614 and 1624.

The embodiment illustrated in FIGS. 25A-25F may be used to secure a feeding tube for use without a patient interface. For example, the tube pad may be attached to the dermal patch via the two-part releasable connection system 1614, 1662, without a covering component covering the dermal patch and interface side of the tube pad. Alternatively, the pad may be attached to the dermal patch via the two-part releasable connection system 1614, 1662, and a panel or patch may be applied over the dermal patch and tube pad to assist with securement of the tube pad to the dermal patch. The panel (not illustrated in FIGS. 25A-25F) may comprise a second part of a two-part releasable connection arrangement for connection to first parts 1614 and 1663 of the dermal patch and tube pad.

A construction of the tube pad is illustrated in FIG. 25A by a stack of parts 1680. Preferably one or both of facing surfaces of the first and second parts 1663 and 1662 is provided with adhesive for bonding the first and second parts together, with a portion of the tab 1670 captured there between.

FIGS. 26A-26D illustrates an alternative embodiment of a securement system 1705 for securing both a patient interface and a feeding tube together on a user's face. The embodiment illustrated in FIGS. 26A-26D is similar in operation to the embodiments described with reference to FIGS. 12A-12C and 20A-20D. A dermal patch 1710 is provided for affixing to the skin of a patient. An over patch or panel 1720 is provided for affixing to a tube side 1712a of the dermal patch. The tube side 1712a of the dermal patch 1710 or a patient side of the panel, or both, comprises an adhesive for bonding the two components together. A first part 1750 of a two-part connection arrangement is provided on an interface side 1712b of the panel, for connection with a corresponding second part 1724 of the two part releasable connection arrangement adhered or otherwise fixed to a patient interface 2000. Alternatively the second part 1724 may be attached to an interface patch affixed to the patient interface. The securement system 1705 comprises a first 1713a and second 1713b primary backing sheets or liners for protecting adhesive on a patient side of the dermal patch, and an intermediate backing liner or sheet 1713c for protecting an adhesive layer on the back of the panel 1720. The dermal patch 1710, panel 1720, first part 1750, primary backing liners 1713a and 1713b, and the intermediate backing liner 1713c are provided as a dermal patch assembly 1705a, as shown in FIGS. 26A-26B. A portion 1730 of the dermal patch is adhered to the panel, the intermediate backing liner covering a remaining portion of the tube side of the panel.

In use, the dermal patch assembly 1705a is attached to the patient interface 2000 by the two part releasable connection system comprising first and second parts 1750 and 1724. Preferably a carer removes one of the primary backing liners 1713a to expose adhesive on a portion of the patient side of the dermal patch 1710 to be fixed near to the patient's nostril. Preferably once the carer has adhered the patient interface to the patient's skin in position below the patient's nose, the carer removes the second primary backing sheet 1713b to expose the remainder of the adhesive on the patient side of the dermal patch, and affixes the remainder of the dermal patch in place on the patient's face. Preferably the patient interface is attached to the patient's face as described after a feeding tube has been inserted in the patient's nostril, the patient interface placed over the tube 2, as illustrated in FIGS. 19A-19D. Alternatively, the feeding tube 2 may be inserted in the patient's nostril after the patient interface has been positioned on the patient's face, the feeding tube passing over the patient interface.

With the patient interface fixed to the patient's face, the carer lifts a distal end 1740 of the interface and panel 1720 and removes the intermediate backing liner 1713c to expose adhesive on the tube side of the panel 1720. While holding the panel away from a tube side of the dermal patch, the carer places a portion of the feeding tube 2 across the tube side of the dermal patch. With the tube correctly positioned on the tube side of the dermal patch, the panel is fixed onto the dermal patch to capture and retain the tube 2 between the panel and the dermal patch.

The illustrated embodiment shows the intermediate backing liner fixed to the tube side of the panel 1720. Alternatively the tube side of the dermal patch 1710 is provided with adhesive and the intermediate liner 1713c. Once the intermediate liner 1713c is removed, adhesive on the tube side of the dermal patch is exposed. Placement of the tube 2 onto the dermal patch is assisted by the adhesive on the tube side of the dermal patch which affixes the feeding tube thereto before the panel is applied over the tube and dermal patch to secure the feeding tube between the panel and the feeding tube.

The described preferred sequence for applying the securement system 1705 is illustrated in FIG. 26C by arrows A to E, the finally installed patient interface and feeding tube illustrated following arrow E.

FIGS. 27A-27D illustrates an alternative embodiment of a securement system 1805 for securing both a patient interface and a feeding tube together on a user's face. The securement system comprises a dermal patch 1810 and a two-part releasable connection arrangement for attaching the patient interface 2000 to the dermal patch, as described earlier with reference to FIGS. 5 to 11. In this embodiment, the backing 2004 comprises a flap 1840 formed by a slit 1841 extending from an edge of the backing to a position inside of the perimeter of the backing 2004, the flap being connected to the backing by a portion 1842 of the backing or flap at an inside end 1843 of the slit.

As described with reference to FIGS. 5 to 11, the patient interface is connected to the dermal patch via a two-part releasable connection arrangement. A first part 1850 of the releasable connection arrangement is attached to or formed with the dermal patch. A second part 1824 of the releasable connection arrangement is attached to or formed with the patient interface. A portion of the second part is attached to or formed with a patient side of the flap 1840. With the patient interface secured to the dermal patch attached to a patient's face, the flap of backing 2004 is secured to the dermal patch via the two-part releasable connection system. Without removing the patient interface from the dermal patch attached to the patient's face, the flap may be removed or peeled away from the dermal patch to release the connection between the first part and the second part attached to or formed with the flap portion of the backing 2004. A remaining portion of the backing is retained by the dermal patch while the flap is peeling off the dermal patch. The feeding tube, once installed in the patient's nostril, is positioned over the patient interface and over the dermal patch with the flap peeled away from the dermal patch. The flap repositioned over the tube and dermal patch to secure the tube between the dermal patch and flap, the flap being retained over the tube by the two-part releasable connection arrangement.

Where a user requires additional or heightened security of user interface and/or feeding tube positioning or securement, a secondary level of securement can be utilized. Such an additional level may include application of an over patch. Such an over patch may be an adhesive patch and can be installed over the top of the user interface and/or tubing and adhered to a portion of the dermal patch.

The flap provides an advantage in that it provides the nurse or carer with a "third hand". With the patient interface positioned on the patient's face and secured to the dermal patch, the carer may use both hands to position the feeding tube 2 by lifting the flap with one hand, positioning the tube on the dermal patch with the other hand, and then replacing the flap to secure the tube to the dermal patch. With the tube correctly retained by the flap, the nurse has both hands free for preparing and attaching an over patch to complete securement of the tube in position. Without the flap and where the securement method is to tape the feeding tube to the patient's face or patient interface with adhesive tape, the carer is required to prepare a piece of tape or an adhesive patch and hold the tube in position which can be difficult with a single pair of hands.

FIGS. 27A-27D disclose a number of slightly different embodiments. In one embodiment, shown in FIG. 27C, the flap is created by a slot that extends to an upper edge of the backing. In another embodiment, shown in FIG. 27D, the flap is created by a slot that extends to a lower edge of the backing. And in another embodiment, shown in FIG. 27B, the flap is created by a slot that extends to an outer edge of the backing. The slot may extend to any part of the perimeter of the backing, however the illustrated embodiments are preferred.

Other securement systems for securing a feeding tube to a patient interface are described with reference to FIGS. 29A to 41.

FIGS. 29A-29B illustrates a clip or holder 4010 for attaching to the front of a patient interface to secure a feeding tube to the patient interface. An interface side 4011 of the holder is adapted to be affixed to the patient interface to fix the feeding tube 2 between the holder and the patient interface to couple the feeding tube and patient interface together. For example, an adhesive is provided to the interface side of the holder 4010 for bonding the holder to the patient interface. The adhesive may be provided over the full surface of the holder interface side 4011 so that when the holder is attached to the interface the holder is bonded to both the interface and the tube. Alternatively, a hook and loop material two-part releasable connection arrangement may be applied between the holder and the patient interface. The interface side of the holder is shaped to be complementary with the shape of the patient interface. The holder 4010 may be formed from a soft material, such as a foam material.

An alternative holder 4020 is illustrated in FIGS. 29C-29D. The holder 4020 is formed from a suitably rigid material for clipping to the patient interface. The holder is shaped to clip over a complementarily shaped feature on the patient interface. For example, the holder comprises a recess 4022 or female part for clipping over a complementary male part or shape on the patient interface. Alternatively the holder comprises a male part for clipping to a female part on the patient interface. Alternatively or additionally the feeding tube securement system comprises a two-part releasable connection arrangement for connecting the holder to the patient interface. Alternatively the holder may be fixed to the patient interface with an adhesive. The holder 4020 comprises a recess 4023 for receiving the tube 2. In use, the tube may be fitted or clipped to the recess 4023 prior to fitting the holder to the patient interface. The recess 4023 may comprise the same features as the recess 218 of clip 220 described with reference to FIGS. 4A-4F.

FIG. 32A illustrates a securement system for securing a feeding tube 2 to a patient interface 2000 comprising an integrally formed female feature 4122 or part for connection with a feeding tube holder 4120 comprising a complementary male feature 4123 or part. The holder 4120 may comprise a channel or aperture for receiving the tube 2. Alternatively, as shown in cross section in FIG. 32B, the tube holder may comprise a material 4124 for wrapping around the tube 2 to couple the holder 4120 to the tube 2. For example, an adhesive is provided to one or both sides of the material 4124 for affixing the material to the tube and to itself by wrapping the material around the tube and onto itself.

An alternative embodiment for a feeding tube securement system is illustrated in FIGS. 32C-32E and comprises a dermal patch 4110 with a male or female part 4122, 4130 for interfacing with a holder 1420 comprising a complementary part attached to the tube, for example male part 4123 as illustrated.

Figure 33:
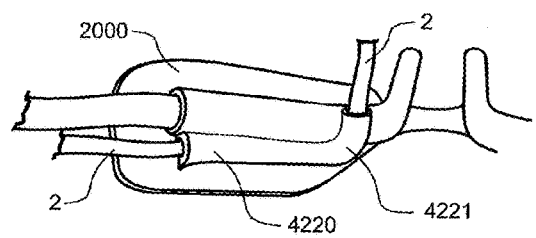
FIG. 33 illustrates a securement system for securing a feeding tube to a patient interface.
Figure 34A:
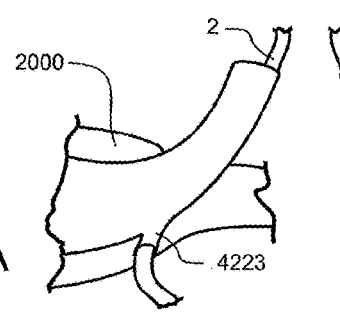
FIGS. 34A-34C illustrate a securement system for securing a feeding tube to a patient interface.
Figure 34B:
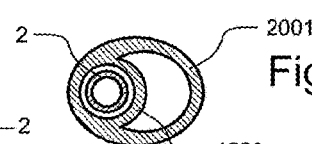
Figure 34C:
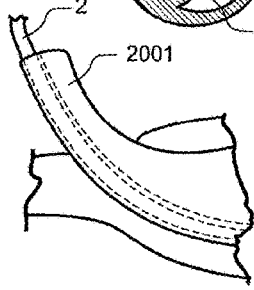

FIG. 33 illustrates a securement system for securing a feeding tube 2 to a patient interface 2000 comprising an integrally formed conduit or closed channel 4220 for retaining the feeding tube. Preferably the channel comprises an elbow 4221 for maintaining a bend in the feeding tube to align the feeding tube with the patient's nasal passage. FIGS. 34A-34C illustrates a similar embodiment wherein the integrally formed conduit or closed channel 4220 is provided within a nasal prong 2001 of the patient interface 2000, as shown in cross section in FIG. 34B. As shown in FIG. 34A, the channel formed within a prong may have an entry point 4223 at a base of a prong 2001. Alternatively, as shown in FIG. 34C, the channel may extend beyond the base of the prong to channel the feeding tube across the patient's face with the patient interface fitted to the patient's face. The conduit 4220 and prong are formed together to have an approximately circular outer wall common to both the prong and the conduit. The approximately circular encompassing perimeter of the prong reduces a stress concentration within the nares from the competing feeding tube and prongs, thus increasing comfort and reducing areas of irritation and possibly infection.

Figure 35A:
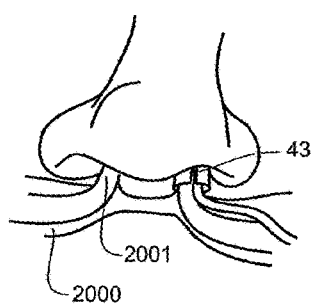
FIGS. 35A-35C illustrate a securement system for securing a feeding tube to a patient interface.
Figure 35B:
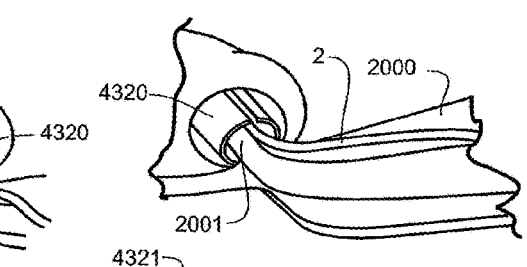
Figure 35C:
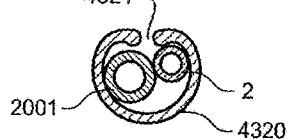

FIGS. 35A-35C illustrates an alternative embodiment of a securement system for securing a feeding tube to a patient interface 2000. The securement system comprises a tube or hollow member 4320 for receiving the patient interface nasal prong 2001 and the feeding tube 2. The hollow member is preferably shorter in length than the length of the nasal prong. In use, the hollow member is fitted over the nasal prong. The feeding tube may be threaded through the hollow member prior to fitting the hollow member over the prong. In the illustrated embodiment, the hollow member is open along its length by a longitudinal slot 4321. The feeding tube may be inserted longitudinally via the slot into the hollow member. Preferably the hollow member is formed of a soft material for providing a comfort fit within the patient's nostril. The hollow member or an inner surface of the hollow member may be formed from a material having high surface friction, for example a rubber. For example, a silicone may be co-molded with the hollow member for contacting the tube and nasal prong.

The embodiment of FIGS. 36A-36E is a patient interface comprising a clip 4420 for securing the feeding tube 2 to the patient interface. The clip provides a continuous ring of material defining an aperture for receiving the feeding tube. The ring 4420 is formed to have, in an unstressed or un-deformed state, a relatively closed aperture 4421a, shown in FIG. 36C. A carer (for example a nurse) elastically deforms the clip 4420 to open the aperture to a relatively opened state 4421b by pressing opposite sides of the clip (for example with forefinger and thumb) as indicated by arrows 4430, shown in FIG. 36E. With the aperture held in the open state, the carer may thread the feeding tube through the opened aperture 4421b. With the feeding tube in place in the patient's nare, the carer may position the tube within the clip to a desirable position before releasing the sides of the clip. Once the sides of the clip are released, the clip returns elastically towards the un-deformed closed state. The diameter of the tube is larger than an internal dimension of the aperture in the fully closed or un-deformed state. The tube is gripped by the clip as the tube prevents the clip from fully returning to the fully closed or un-deformed state, illustrated in FIG. 36D. As illustrated, the patient interface may comprise other features for retaining or fixing the tube to the patient interface, for example rings 4425.

The embodiment of FIGS. 37A-37B is a patient interface comprising an aperture 4521 for receiving a feeding tube 2. The aperture is arranged below and between the nasal prongs 2001 of the patient interface 2000 so that the tube 2 is routed approximately towards the nares of the patient once the tube is passed through the aperture 4521. The aperture is formed by a ring of material 4522. Preferably the ring of material comprises a slot 4523 for inserting the tube laterally into the aperture.

According to the embodiment of FIGS. 37A-37B the ring of material comprises a clip for securing the tube at the aperture. The clip comprises a male part 4524 and a female part 4525 formed in the ring opposite the male part. The aperture is closed on the tube by mating the male and female parts to secure the tube. In the illustrated embodiment the ring of material also comprises a recess 4526 for receiving the tube 2. The tube 2 is locked in the recess by mating the male part with the female part. With the male and female parts mated, the recess is closed to form a sub-aperture in the ring material. A dimension of the sub-aperture is preferably sized to be slightly smaller than the diameter of the tube so that the tube is firmly gripped once the male and female parts are mated together.

The aperture 4521 provides a carer with a 'third hand', holding the tube loosely. The carer may make further easy adjustment and checking of the feeding tube in the stomach/intestines with the tube retained loosely by the aperture 4521 or with the aperture functioning as a guidance aid. Once the tubing is placed correctly, the carer pushes the male and female parts 4524, 4525 together to secure the feeding tube tightly.

FIGS. 38A-38B illustrates a holder 4620 for securing a tube 2 to a patient interface 2000. The holder comprises apertures 4621 for receiving the prongs 2001 of the patient interface 2000. The holder also comprises an aperture 4622 for receiving the feeding tube. The aperture may be open to a side via a slit 4623 in the material bordering the aperture. In use a carer threads the tube through the aperture or inserts the tube laterally into the aperture via the slit 4623. The holder may be placed over the prongs 2001 before or after the tube is positioned in aperture 4622. The illustrated embodiment comprises a left and a right aperture 4623 for receiving a tube. In use a carer may choose to use either the left of the right aperture 4623.

Figure 43A:
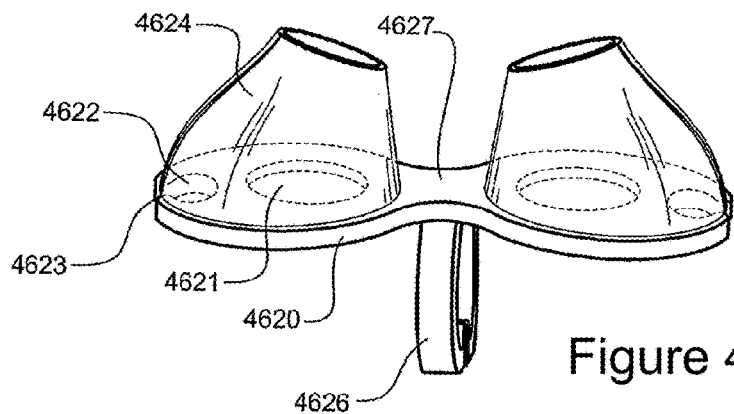
FIGS. 43A-43C illustrate a securement system for securing a feeding tube to a patient interface.
Figure 43B:
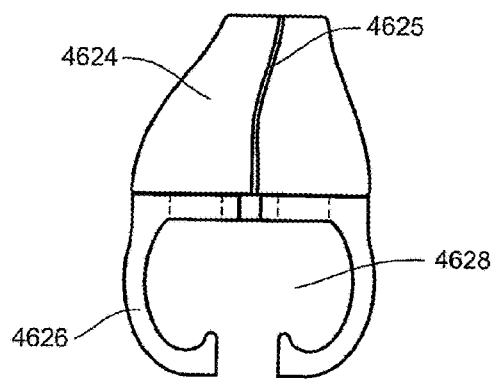
Figure 43C:
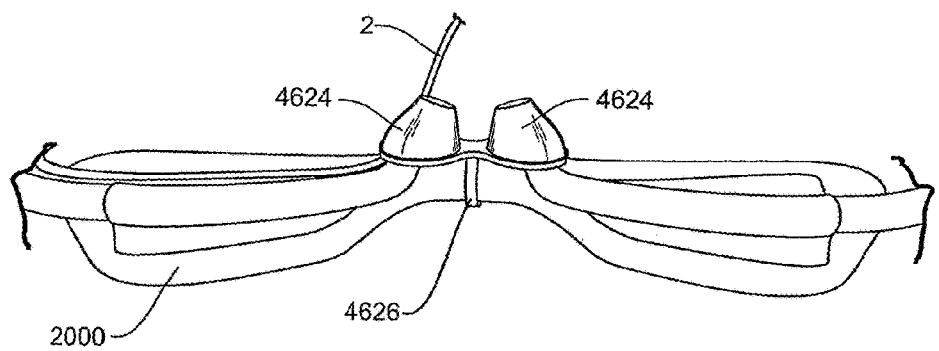

In another embodiment illustrated in FIGS. 43A-43C, the clip 4620 comprises a nare shield 4624. The nare shield is shaped to fit comfortably within the nare of a patient and shrouds or envelopes the feeding tube 2 and nasal prong 2001 (not illustrated in FIGS. 43A-43C). The shield extends from a base 4627 of the clip. The shield extends around the prong aperture 4621 and the feeding tube aperture 4622. The shield comprises a slit 4625 to provide an opening for inserting the feeding tube 2 laterally into the shield. The shield may have an approximately cylindrical or frusto-conical form extending from a base 4627 of the clip. The shield functions in a similar way to the hollow member 4320 described with reference to FIGS. 35A-35C. For additional securement stability to the patient interface, the clip 4620 preferably has a lower clip 4626 for securing the clip 4620 to the patient interface between the nasal prongs. The clip 4626 provides an aperture 4628 for receiving a portion of the patient interface similar to the aperture 4721 described below with reference to FIGS. 39A-39B. In one embodiment, the clip comprises a plurality of apertures 4628, 4721, each aperture sized to receive a portion of the patient interface, either between the two nasal prongs or a portion of the patient interface outside of the two nasal prongs. Each first aperture is open to a side via a slit.

FIGS. 39A-39B illustrates an alternative holder for securing a feeding tube 2 to a patient interface 2000. The holder comprises an aperture 4721 for securing the holder to the patient interface, preferably to a portion of the patient interface located between the prongs 2001. A slit 4724 is provided in the material bordering the aperture 4721. The holder is attached to the patient interface via the slit 4724. The holder comprises an aperture 4722 for receiving the tube 2. The aperture 4722 may be open to a side via a slit 4623 in the material bordering the aperture. In use a carer threads the tube through the aperture 4722 or inserts the tube laterally into the aperture 4722 via the slit 4723. The holder may be attached to the patient interface before or after the tube is positioned in aperture 4722.

FIGS. 40 to 41 illustrates holders 4820, 4920 and 5020 for securing or coupling a feeding tube 2 to a breathing tube 2012 connected to or formed with a patient interface 2000.

FIG. 40 illustrates a holder or slider 4820 coupled to a breathing tube 2012 of a patient interface 2000. The breathing tube 2012 is received in an aperture 4821 of the slider. The slider may slide or move longitudinally along the breathing tube. The slider comprises a second aperture 4822 for receiving the feeding tube 2. The slider the aperture 4822 is open to one side via a slit 4823 for inserting the tube 2 laterally into the aperture. Preferably the breathing tube aperture is also open to one side via a slit (not shown). The slider acts as a routing or guidance aid for positioning the feeding tube. The breathing tube aperture or feeding tube aperture or both may comprise a high surface friction material for providing a grip surface to increase a holding force to one or both tubes. The slider may be formed to have a breathing tube aperture with an internal dimension smaller than the diameter of the breathing tube when the slider is in an unstressed or un-deformed state. To slide the slider along the breathing tube, a nurse or carer must compress opposite sides of the slider to increase the internal dimension or open the aperture slightly so that the aperture does not grip the tube 2012. When released, the aperture returns to the un-deformed state and grips the diameter of the tube 2012. Similarly the slider may be formed to have a feeding tube aperture with an internal dimension smaller than the diameter of the feeding tube when the slider is in an unstressed or un-deformed state as described previously.

The holder or slider 4920 illustrated in FIG. 41 is similar to the slider 4820 described with reference to FIG. 40 and comprises a first aperture 4921 for coupling the slider to a breathing tube 2012 and a second aperture 4922 for coupling to a feeding tube 2. The embodiment of FIG. 41 also comprises a clip 4930 located at the patient interface 2000 for coupling the holder or slider 4920 to the patient interface. In use a carer initial uses the slider as a guidance aid to couple the feeding tube to the breathing tube. Once the correct insertion position of the feeding tube has been confirmed, the carer finalizes the securement of the feeding tube by sliding the slider 4920 to the clip 4930 to couple the slider via the clip to the patient interface. In the illustrated embodiment the clip comprises a female part for receiving a male part of the slider; the female part is a slit for receiving a side of the slider. Alternatively the clip 4930 comprises a male part for coupling to a corresponding female part of the slider. Preferably the breathing tube aperture does not clamp onto the breathing tube as described with reference to FIG. 40. Securement of the slider to the patient interface is achieved by the clip at the patient interface. The feeding tube aperture 4922 may comprise features for gripping the tube as previously described, for example as described with reference to FIGS. 4, 36 and 37.

Figure 42:
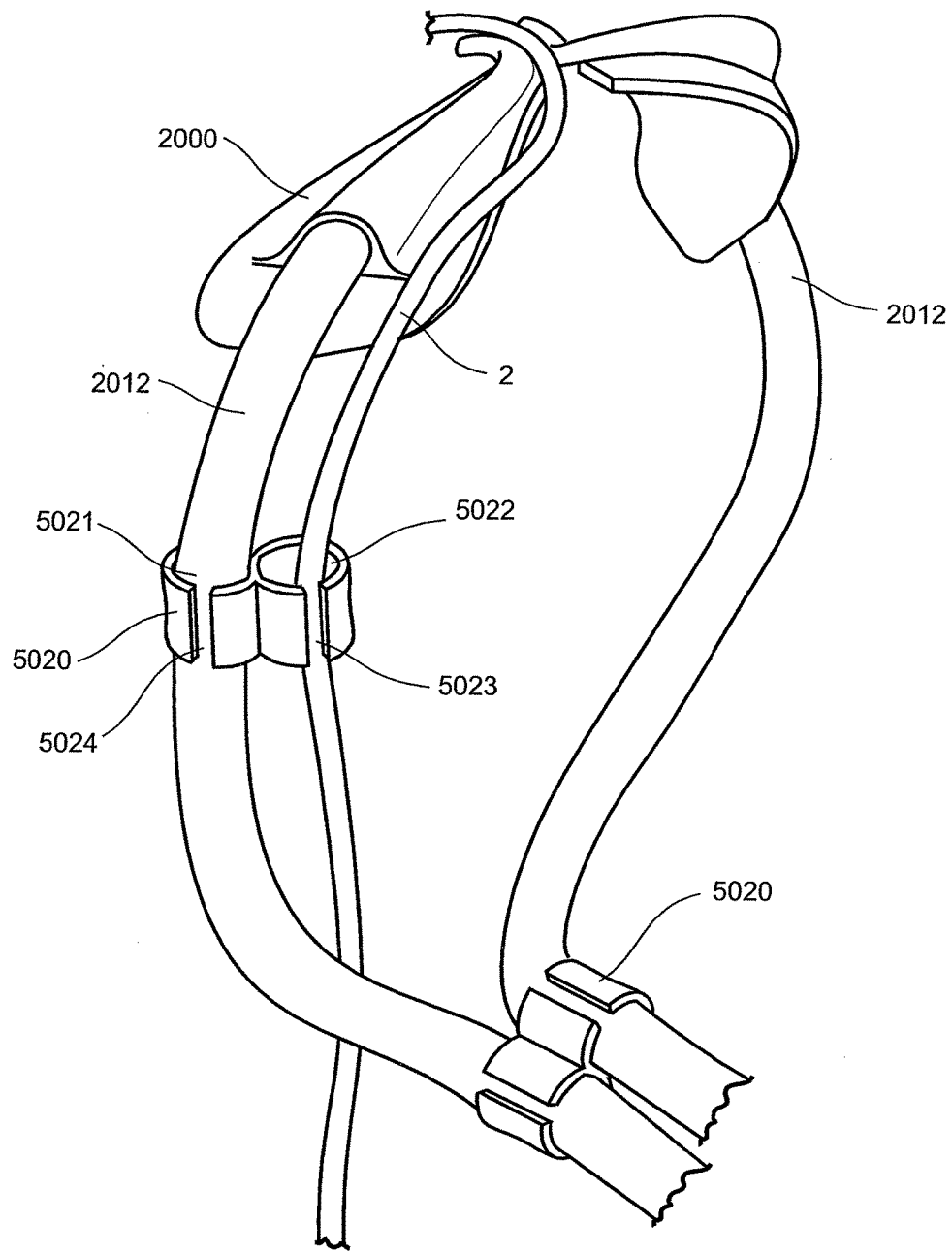
FIG. 42 illustrates a securement system for securing a feeding tube to a patient interface.

The holder or slider 5020 illustrated in FIG. 42 is similar to the sliders 4820, 4920 described with reference to FIGS. 40 and 41. Slider 5020 comprises a first aperture 5021 for coupling the slider to a breathing tube 2012 and a second aperture 5022 for coupling to a feeding tube 2. Preferably the breathing tube aperture and the feeding tube aperture are open to a slide via a slot 5024, 5023 for inserting the respective tube laterally into each aperture. In this embodiment, the breathing tube aperture and the feeding tube aperture are the same size or of a similar size. In applications where the feeding tube has a smaller diameter than the breathing tube, the feeding tube is retained loosely in the feeding tube aperture 5022. As shown in FIG. 42, the same slider may also be used to couple a left and right breathing tube together. This arrangement assists to route both breathing tubes together and reduces the likelihood of entanglement with the feeding tube.

The various securement system embodiments described comprise a two-part releasable attachment or connection arrangement. Preferably the two-part releasable connection arrangements comprise a hook and loop material (such as Velcro™). In one form, a hook and loop type two-part releasable connection arrangement comprises hooks integrally formed with a patient interface. For example, hooks may be integrally moulded with a patient interface. FIG. 28 illustrates hooks 2020 integrally moulded with a front surface of the patient interface for connection with the complementary loop material 1520 attached to a feeding tube 2. FIG. 28 further illustrates hooks 2020 integrally moulded with a rear or patient side 2015 of the patient interface for connection with complementary loop material attached to a dermal patch.

Alternatively the two-part connection arrangements comprise an adhesive. For example, the first part or the second part or both comprise an adhesive that releasably affixes the first and second parts together. The adhesive preferably allows the first and second parts to be affixed by a retention force, removed and replaced or affixed together again with the same retention force. Preferably the adhesive is an acrylic based adhesive or a pressure sensitive adhesive.

In this specification the term dermal patch is used to describe a patch attachable to the skin of a patient. Preferably the dermal patch is formed from a hydrocolloid material. Alternatively, a dermal patch may be formed from another flexible or pliant material. For example, a dermal patch may be formed from silicone with an adhesive, generally being of a dermatologically sensitive adhesive such as a polyurethane adhesive applied to the patient side of the patch.

Some of the described securement systems comprise a panel or patch for applying to or over a dermal patch affixed to the skin of a user, or to a patient interface fitted to the patient's face. Such a panel may be formed from a hydrocolloid or some other suitably flexible or pliant material, such as a silicone.

Securement systems for securing both a feeding tube and a patient interface have been described with reference to FIGS. 12 to 26. However, one or more of the described embodiments may be used to secure a feeding tube without securement of a patient interface. One or more of the described embodiments may be provided without a first part of a two-part releasable connection arrangement for connection with a corresponding second part of the two-part releasable connection arrangement associated with a patient interface. For example, the embodiments described with reference to FIGS. 12, 13, 15 to 22 and 24 may be provided without first parts 350, 450, 650, 750, 850, 950, 1050, 1150, 1250, 1350, 1550a.

Figure 45A:
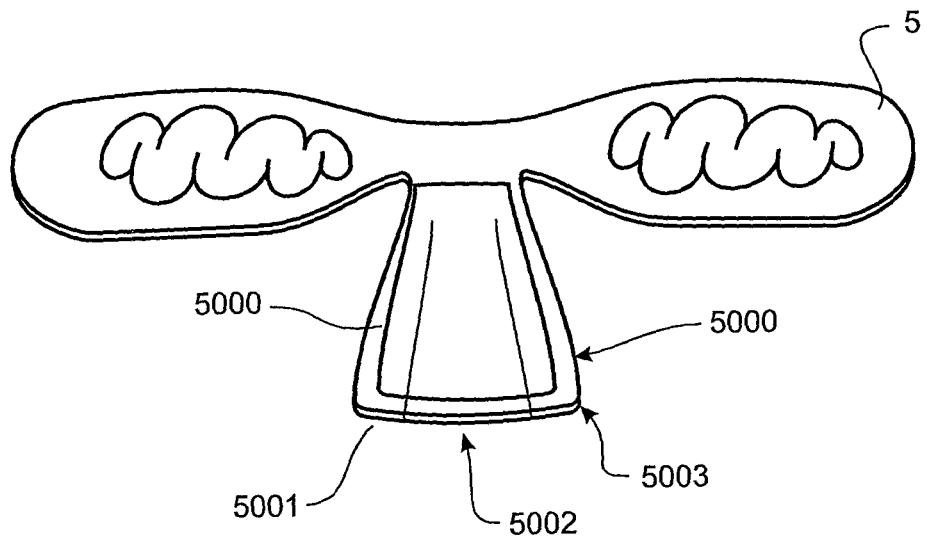
FIGS. 45A and 45B illustrate an embodiment of a securement system for securing a feeding tube in position on a patient's face, as well as securing a patient interface in position.
Figure 45B:
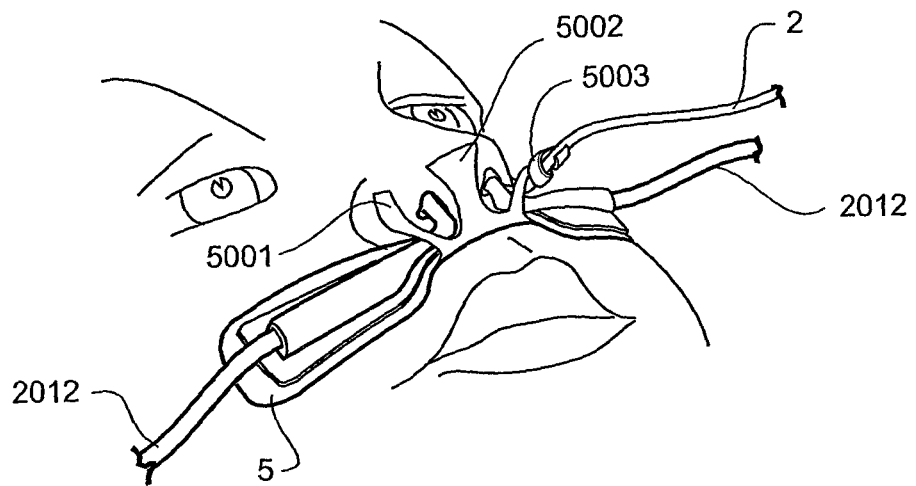

In another embodiment, as shown by FIGS. 45A and 45B, a securement system can have a flap 5000 with splits or sections (or bifurcated or trifurcated) so as to provide a series of flap portions which can be used to connect with a patient, a patient interface, or a tube (such as a feeding tube 2). The dermal patch 5 can have a two-part releasable connection system, as previously described, and a section of the flap 5000 can have an adhesive, at least initially of which may be covered by a backing paper or protective cover 5001 or the like. As shown in FIG. 45B, such a securement system of FIG. 45A can be provided in use to engage or connect with or attach to a patient around the nostril or nare region of a user's nose, about the septum and onto the tube 2. In this manner, a secure connection is made of the patient interface and tube in an operational position, yet the flap portion 5000 engaging with the tube 2 can be unwound and re-positioned if necessary, likewise the dermal patch 5 can be re-positioned on the user's face as necessary, as hereinbefore described. For example, as shown, a centrally located flap portion 5002 can be used to adhere or attach to the septum region of a user's nose, while a second flap portion 5003 can be used to connect and be wrapped about the tube 2, with the remaining third flap 5001 adhered or connected to a region of the users nose, for example about the nare or nostril region. In this manner, a patient interface and a feeding tube 2 are retained in position securely to the patient/user.

Figure 46:
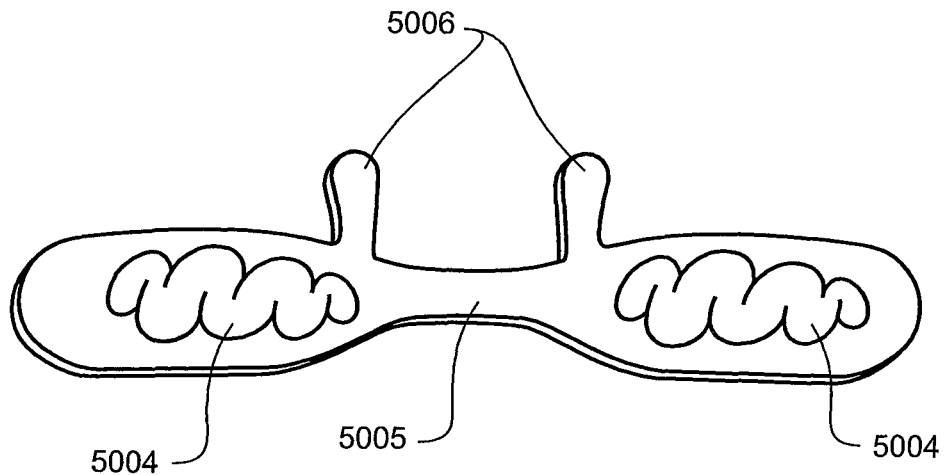
FIGS. 46 and 47 illustrate a single dermal patch which may be utilised in combination with many of the securement systems of this invention.
Figure 47:
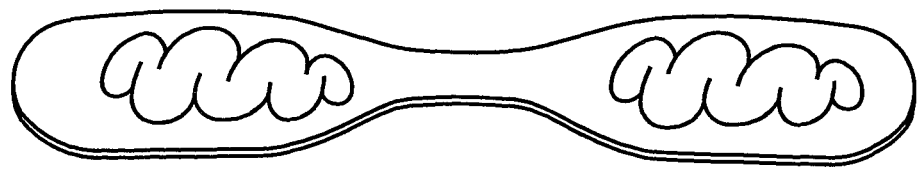

In another alternative embodiment to that describe above, as shown by FIGS. 46 and 47, is a dermal patch, provided as a single patch, each with a joining middle section 5005 joining the respective releasable two-part connection system components 5004 provided on each end or wing of the patch. In one version, (e.g. FIG. 46) such a dermal patch comprises of two flap portions 5006, each such flap portion provided for positioning onto the side of the patient/user's nose for increased retention.

FIG. 47 shows the single dermal patch in a simplified form which may be provided for use in combination with the various embodiments described in this specification utilising a dermal patch, the single dermal patch replacing multiple dermal patch use.

Figure 48A:
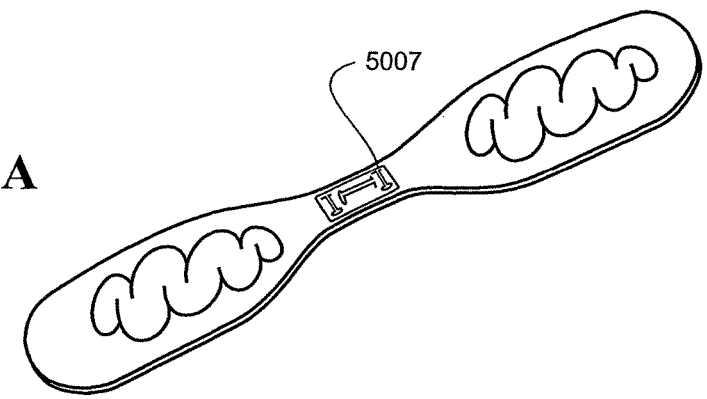
FIGS. 48A-48C illustrate a securement system according to another aspect of this invention in which a holder is utilised to securely position and retain both of a tube and a patient interface in an operational position.
Figure 48B:
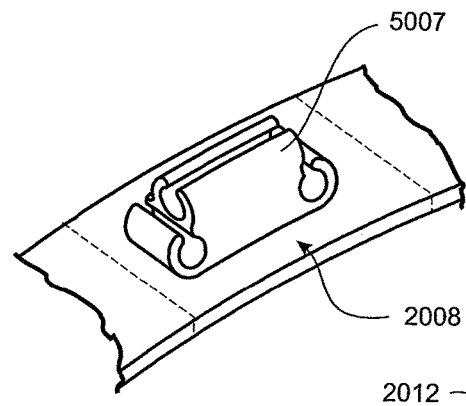
Figure 48C:
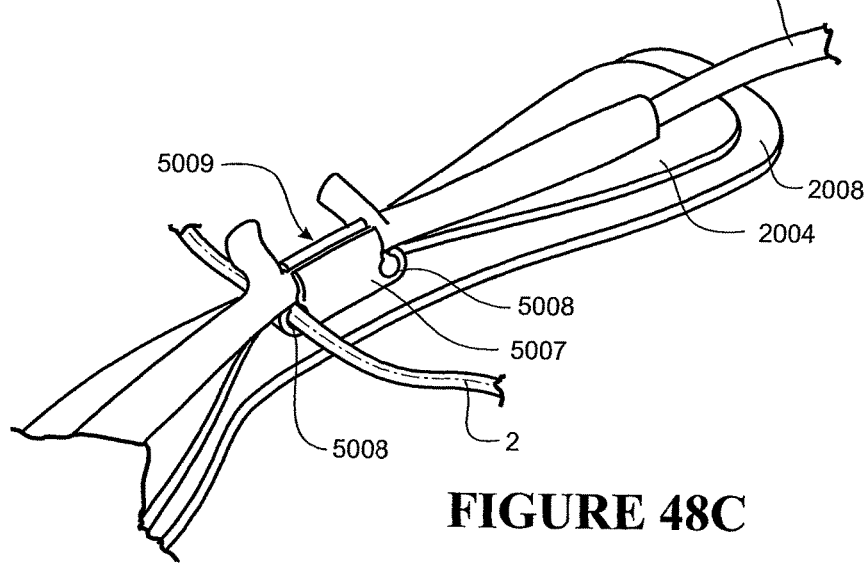

In yet a further alternative, as shown by FIGS. 48A-48C, a securement system for securing a tube to a patient interface and/or a dermal patch is shown. FIGS. 48A-48C show a holder 5007 which has an interface side 5009 attachable to the patient interface, at least a first channel or recess 5008 for securing a feeding tube 2 and a dermal patch side for attachment or adherence of the holder to a dermal patch 2008. Shown is a single dermal patch 2008 used in conjunction with a holder 5007. The holder 5007 has a channel or recess (or slot or aperture) on the interface side 5009 into which the bridge portion of a patient interface (e.g. nasal cannula) can be inserted and retained therein. The at least first channel disposed on the side of the holder 5007 can be positioned perpendicular and on either or both sides of the interface side channel, thus allowing for retention of a tube through either nostril. The holder 5007 can retain both a tube 2, such as a naso-feeding tube, and a patient interface, such as a nasal cannula, in an operational position. Yet, the configuration and arrangement is such that the patient interface can be removed and the tube 2 also then removed or re-positioned as necessary.

The holder 5007 can be formed of a relatively soft or pliable material, such as a polymeric material, so as to effectively grip and retain the portion of whatever component is placed in-situ. Further, pliability can allow for manual manipulation of the holder and the channel or recess so as to allow ease of installation of the patient interface or tube into position and retention, yet on release the holder 5007 can move back to its original position to more securely hold the installed portions.

Tube Securement System—One Embodiment

With reference to FIGS. 44A to 44J a dermal patch is indicated at 5, which is in use adhered or otherwise attached to a patient's skin, typically the face for fixing or holding a feeding tube such as a nasogastric, nasoduodenal and nasojejunal tube in position. The dermal patch has a patient side 10) that is fixed to the patient's skin and a tube side 12 (see FIG. 44D). The patient side 10 of the dermal patch is preferably provided with a dermatologically sensitive adhesive, for example a polyurethane adhesive. The adhesive may fully cover the patient side, or partially cover the patient side as for example adhesive dots or lines. Preferably the adhesive of the patient side of the dermal patch is protected for use with a removable backing material 13 that is in use removed by a nurse/carer immediately prior to positioning on the patient's face. The dermal patch is sized for its intended application i.e. is relatively smaller for use with newborns or infants, and relatively larger for use with adults, and a range of sizes and/or shapes of dermal patches may be provided. The dermal patch is preferably formed from a hydrocolloid material, with an adhesive provided to the patient side.

A panel 20 is coupled to the dermal patch at a fold region or line 15, which in the embodiment shown is approximately parallel to an intended secured position of a tube but in other embodiments may cross an intended secured position of the tube. The panel 20 may be integrally formed with the dermal patch, also of a same hydrocolloid material for example. In the embodiment shown the fold line of which the panel 20 attached to the patch 10 is intermediate of the width of the dermal patch. In other embodiments the panel may be a separate component from the dermal patch.

The panel 20 has a tube side 21 and a side 22. The dermal patch 5 comprises on its tube side 10 a first adhesive part and the panel 20 forms the other part, of a two-part attachment or connection system for affixing a tube to the dermal patch. In the embodiment shown adhesive is provided on a portion of the area of the tube side of the dermal patch, adjacent or below the panel 20. The panel 20 comprises on its tube side 21 a second tube adhesive part. In both cases the adhesive may be present as a fully covering film, or as a partial cover as for example adhesive dots or lines.

The adhesive areas on the tube side 10 of the dermal patch and the tube side 22 of the panel 20 are provided with a removably attached protective backing sheet or sheets. A single backing sheet may cover both but in the embodiment shown each is provided with a separate backing sheet 25 and 26. The backing sheet, or sheets 25 and 26, may also extend beyond an external periphery of the tube side 10 of the dermal patch and the tube side 22 of the panel 20 as indicated at 25*a* and 26*a*, and may further include extending tabs 25*b* and 25*c* at one or both ends, to facilitate easy manual removal of the protective backing sheets in use.

Figure 44A:
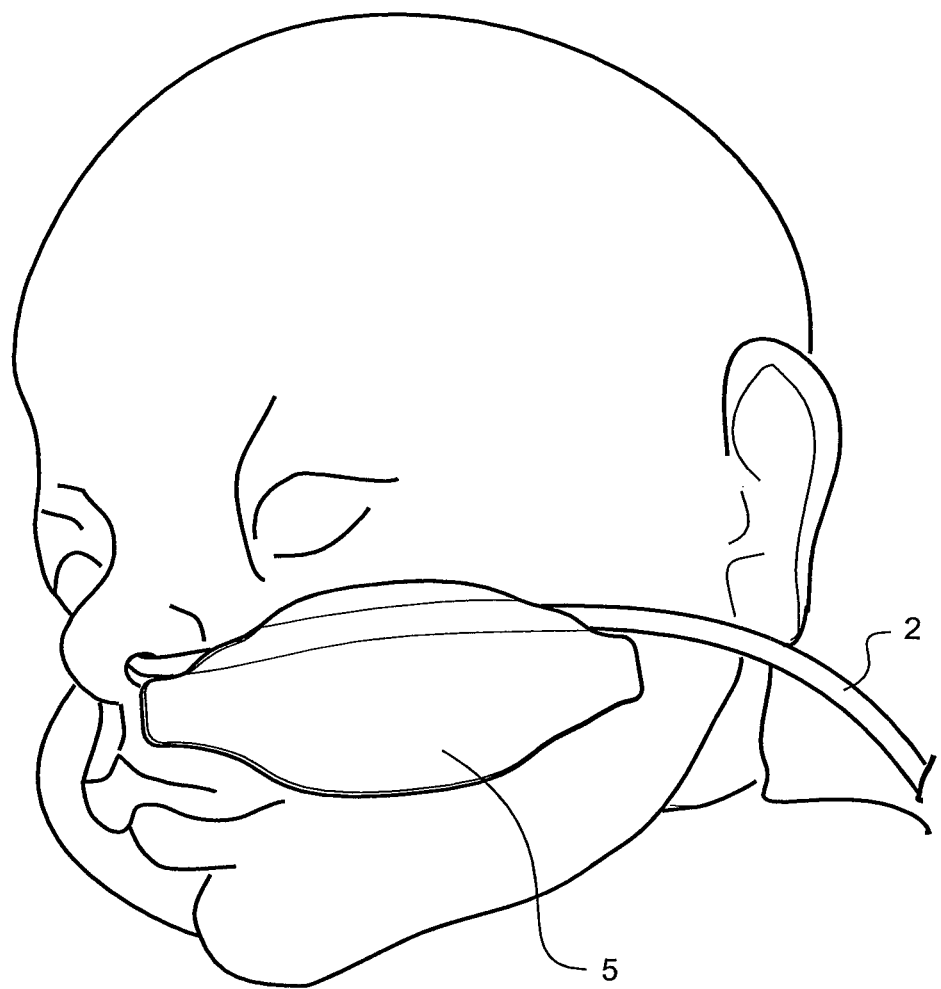
Figure 44B:
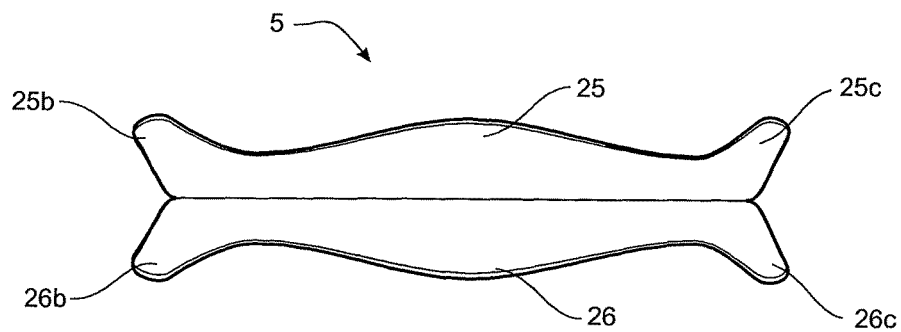
Figure 44C:
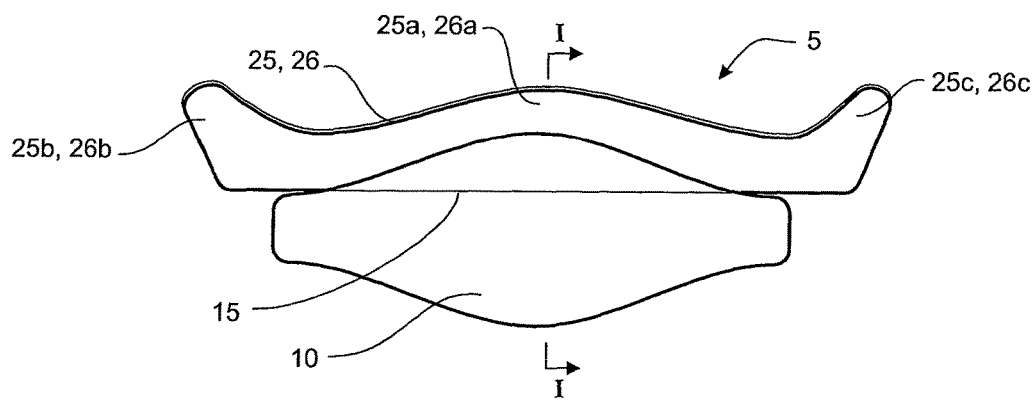
Figure 44D:
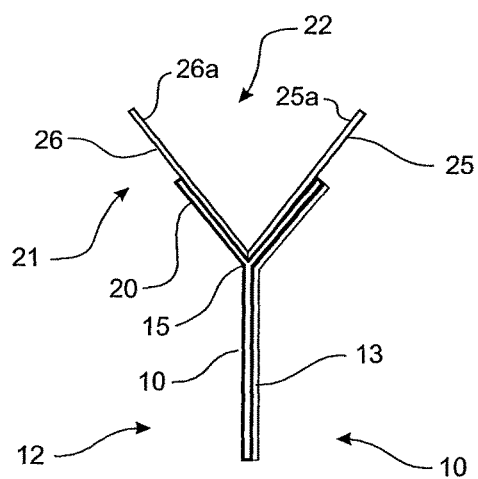
Figure 44E:
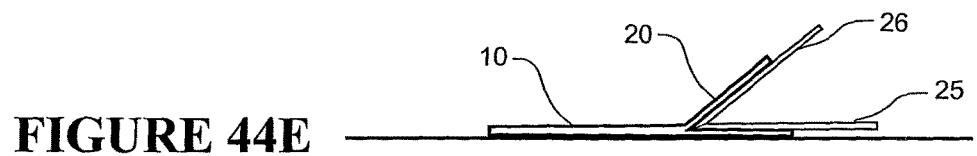
Figure 44F:
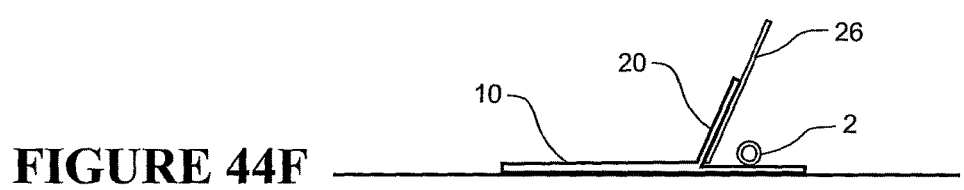
Figure 44G:
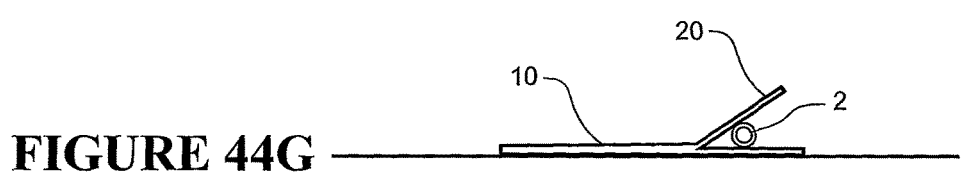
Figure 44H:
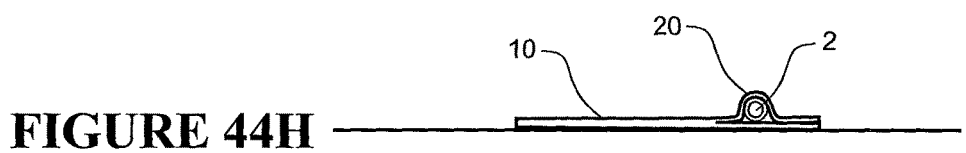
Figure 44I:
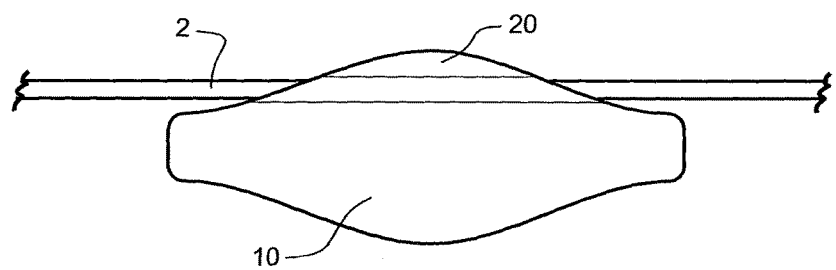

The adhesive on the tube side 22 of the panel 20 has higher adhesion/bond strength than the adhesive on the tube side 10 of the dermal patch 5. In some embodiments the adhesion/bond strength is at least two, five, or more times higher. In use and referring particularly to FIGS. 44E to 44H, after the dermal patch has been adhered to the skin of a patient in the desired position, such as on an infant's face, as shown in FIG. 44E, the backing sheet 25 is then removed to expose the adhesive on the tube side 10 of the dermal patch, and a tube 2 is positioned on the adhesive. The relatively lower adhesion or bond strength of the adhesive on the tube side 10 of the dermal patch enables the tube to be lifted fully or partially off and it's position adjusted until perfected ie release from and re-attachment of the tube to the dermal patch. The backing sheet 26 is then removed to expose the higher bond adhesive on the tube side 10 of the panel 20 as shown in FIG. 44G, and the panel 20 is pressed down to adhere the panel to the tube side 10 of the dermal patch around the tube 2 thus fixing the tube in position as shown in FIGS. 44H and 44I (and also FIG. 44A).

The adhesives are pressure sensitive adhesives and may be an acrylic based adhesive for example. Optionally the adhesive areas may not reach the edge(s) of the dermal patch 10 or panel 20.

The dermal patch 10 is a generally planar pad having a thickness much less than both its width and its length. In some embodiments, the pad has an approximately overall oval shape as shown, but it may be of other shapes.

More than one such dermal patch 5 may be used to fix a tube to a patient, for example, one securement system 5 may be used near the patient's nostril and another spaced from the nostril for directing the tube across the patient's face.

PREFERRED FEATURES

1a. A securement system for securing a tube to a patient's face, comprising:
  a tube two-part releasable connection arrangement,
  a dermal patch having a patient side and a tube side, the patient side of the dermal patch being attachable to the skin of a user, the tube side of the dermal patch being provided with a first part of the tube two-part releasable connection arrangement, and
  a complementary second part of the tube two-part releasable connection arrangement being attachable or connectable to the tube, in use the first part and second part releasably connected together for affixing the tube to the dermal patch.

1b. A securement system as claimed in claim 1a, comprising a first part of an interface two-part releasable connection arrangement provided to the tube side of the dermal patch for releasably connecting to a complementary second part of the interface two-part releasable connection arrangement coupled to or formed with a patient interface.

1c. A securement system as claimed in claim 1b wherein the securement system comprises a common first part being common to both the tube two-part releasable connection arrangement and the interface two-part releasable connection arrangement, the common first part being both the first part of tube two-part releasable connection arrangement and the first part of the interface two-part releasable connection arrangement.

1d. A securement system as claimed in any one of claims 1a to 1c wherein the second part of the tube two-part releasable connection arrangement is a pad for wrapping around a portion of the tube.

1e. A securement system as claimed in any one of claims 1a to 1d wherein the first part of the tube two-part releasable connection arrangement comprises a hook or a loop, and the second part of the tube two-part releasable connection arrangement comprises the other of the hook or loop.

1f. A securement system as claimed in claim 1b wherein the securement system comprises an interface patch for attaching to a patient interface, and the second part of the interface two-part releasable connection arrangement provided on a patient side of the interface patch.

1g. A securement system for securing a tube to a patient interface comprising:
  a tube two-part releasable connection arrangement,
  a patient interface being provided with a first part of the tube two-part releasable connection arrangement, and
  a complementary second part of the tube two-part releasable connection arrangement being attachable or connectable to the tube, in use the first part and second part releasably connected together for affixing the tube to the patient interface.

1h. A securement system as claimed in claim 1g wherein the second part of the tube two-part releasable connection arrangement is a pad for wrapping around a portion of the tube.

1i. A securement system as claimed in claim 1g or 1h wherein the first part of the tube two-part releasable connection arrangement comprises a hook or a loop, and the second part of the tube two-part releasable connection arrangement comprises the other of the hook or loop.

1j. A securement system as claimed in claim 1i wherein the first part of the tube two-part releasable connection arrangement comprises hooks integrally formed with the patient interface, for connection to loops of the second part of the tube two-part releasable connection arrangement attached to the feeding tube.

1k. A securement system as claimed in any one of claims 1g to 1j wherein the securement system comprises a dermal patch having a patient side and an interface side, the patient side of the dermal patch being attachable to the skin of a user, the interface side of the dermal patch being provided with a first part of an interface two-part releasable connection arrangement for releasably connecting to a complementary second part of the interface two-part releasable connection arrangement coupled to or formed with a patient side of the patient interface.

1l. A securement system as claimed in claim 1k wherein the second part of the interface two-part releasable connection arrangement comprises hooks integrally formed with the patient side of the patient interface, for connection to loops of the first part of the interface two-part releasable connection arrangement provided to the dermal patch.

2a. A securement system for securing a tube to a patient's face, comprising:
 a two-part releasable connection arrangement,
 a dermal patch having a patient side and a tube side, the patient side of the dermal patch being attachable to the skin of a user, the tube side of the dermal patch being provided with a first part of the two-part releasable connection arrangement, and
 a panel having a tube side, the tube side being provided with a complementary second part of the two-part releasable connection arrangement, in use the panel and the dermal patch being releasably connected by the two-part releasable connection arrangement to hold the tube between the panel and the dermal patch.

2b. A securement system as claimed in claim 2a wherein an interface side of the panel is provided with a first part of an interface two-part releasable connection arrangement for connection to a complementary second part of the interface two-part releasable connection arrangement coupled to or formed with a patient interface.

2c. A securement system as claimed in claim 2a or claim 2b wherein the panel and the dermal patch are permanently coupled together at a fold region.

2d. A securement system as claimed in claim 2c wherein the fold region is approximately parallel to an intended secured position of the tube.

2e A securement system as claimed in claim 2c or claim 2d wherein the fold region crosses over an intended secured position of the tube, the fold region comprising a hole or slot for the tube to extend through.

2f. A securement system as claimed in any one of claims 2a to 2e wherein the tube side of the dermal patch comprises an adhesive for fixing the position of the tube before the first and second parts of the two-part releasable connection arrangement are engaged.

2g. A securement system as claimed in any one of claims 2a 2f wherein the tube side of the dermal patch comprises high surface friction material for contacting the tube.

2h. A securement system as claimed in claim 2g wherein the high surface friction material is a rubber material.

2i. A securement system as claimed in claim 2h wherein the high surface friction material is a silicone.

2j. A securement system as claimed in claim 2e wherein the fold region is perpendicular to the intended secured position of the tube.

2k. A securement system as claimed in any one of claims 2a to 2j wherein a side of the panel opposite the tube side is adapted for being written on by a pen or pencil or other writing instrument.

2l. A securement system as claimed in any one of claims 2a to 2k wherein the first part of the two-part releasable connection arrangement comprises a hook or a loop, and the second part of the two-part releasable connection arrangement comprises the other of the hook or loop.

2m. A securement system as claimed in claim 2b wherein the first part of the interface two-part releasable connection arrangement comprises a hook or a loop, and the second part of the interface two-part releasable connection arrangement comprises the other of the hook or loop.

3a. A securement system for securing a tube to a patient's face comprising a clip for releasably receiving the tube, a patient side of the clip attachable to a patient's skin or attachable to or permanently fixed to or integrally formed with one of a dermal patch and a patient interface.

3b. A securement system as claimed in claim 3a wherein the clip comprises a recess or channel for receiving the tube, the recess or channel having a lateral dimension similar to or slightly smaller than a diameter of the tube for firmly gripping the tube.

3c. A securement system as claimed in claim 3a or 3b wherein the clip is located on the dermal patch or the patient interface with the recess in a position intended to be aligned to a patient's nostril.

3d. A securement system as claimed in any one of claims 3a to 3c wherein the clip is releasable from or permanently fixed to the dermal patch or the patient interface.

3e. A securement system as claimed in any one of claims 3a to 3d comprising a plurality of clips provided to the dermal patch or the patient interface.

3f. A securement system as claimed in claim 3e wherein a first clip is provided at an angle to a second clip, the first and second clips thus arranged to maintain a bend in a tube secured by the first and second clip.

3g. A securement system as claimed in claim 3b wherein a surface of the recess for contacting the tube is formed from a rubber material or a material having a high surface friction.

3h. A securement system as claimed in any one of claims 3a to 3g wherein the clip comprises a primary recess and a secondary recess, the primary recess having a first internal dimension for holding the tube, and the secondary recess having a second internal dimension for holding the tube, and the first internal dimension being larger than the second internal dimension, the primary recess and the secondary recess coupled together via an opening.

3i. A securement system as claimed in claim 3e or 3f wherein the clips are arranged to route the tube across a patient's face and into the patient's nostril.

3j. A securement system as claimed in any one of claims 3a to 3i wherein the securement system comprises a dermal patch and a first part of a two-part releasable connection arrangement is provided to a tube side of the dermal patch, the first part adapted to be releasably connected to a second part of the two-part releasable connection arrangement attached to or formed with a patient interface.

3k. A securement system as claimed in claim 3j wherein the securement system comprises an interface patch for attaching to a patient interface, and the second part of the two-part releasable connection arrangement provided on a patient side of the interface patch.

3l. A securement system as claimed in claim 3j or 3k wherein the first part of the two-part releasable connection arrangement comprises a hook or a loop, the second part of the two-part releasable connection arrangement comprising the other of the hook or loop.

3m. A securement system as claimed in any one of claims 3a to 3i wherein the clip is integrally formed with a patient interface comprising a nasal prong, the clip comprising a channel, the channel extending along the nasal prong.

3n. A securement system as claimed in claim 3m wherein the channel extends from the prong and along a body of the patient interface, the channel comprising a bend to direct the tube from the prong and along the body.

4a. A securement system for securing a tube and a patient interface to a patient's face, comprising:
   a dermal patch having a patient side and a tube side, the patient side of the dermal patch being attachable to the skin of a user, and
   a panel having a tube side and an interface side, the tube side of the dermal patch and the tube side of the panel adapted to be connected together to retain the tube there between, and
   a first part of a two-part releasable connection arrangement provided to the interface side of the panel, the first part adapted to be connected to a second part of the two-part releasable connection arrangement attached to or formed with the patient interface.

4b. A securement system as claimed in claim 4a wherein the securement system comprises an interface patch, the interface patch having a patient side and an interface side, and the second part of the two-part releasable connection provided to the patient side of the interface patch, and the interface side of the interface patch adapted to be connected to the patient interface.

4c. A securement system as claimed in claim 4a of claim 4b wherein the securement system comprises a second two-part releasable connection arrangement, a first part of the second two-part releasable connection arrangement being provided to the tube side of the dermal patch, and a second part of the second two-part releasable connection arrangement being provided to the tube side of the panel.

4d. A securement system as claimed in any one of claims 4a to 4c wherein the panel and the dermal patch are permanently coupled together at a fold region.

4e. A securement system as claimed in any one of claims 4a to 4d wherein the tube side of the panel and the tube side of the dermal patch are adapted to be adhered together to secure the tube there between.

4f. A securement system as claimed in claim 4e wherein an intermediate removable protective backing sheet is provided between a portion of the dermal pad and a portion of the panel, a portion of the panel and dermal pad being permanently attached.

4g. A securement system as claimed in any one of claims 4a to 4f wherein the patient side of the dermal patch is provided with a first removable protective backing sheet removably attached to a first portion of the dermal patch and a second removable protective backing sheet attached to a second remaining portion of the dermal patch.

4h. A securement system as claimed in any one of claims 4a to 4g wherein the first part of the two-part releasable connection arrangement comprises a hook or a loop, and the second part of the two-part releasable connection arrangement comprises the other of the hook or loop.

4i. A securement system as claimed in claim 4c wherein the first part of the second two-part releasable connection arrangement comprises a hook or a loop, and the second part of the second two-part releasable connection arrangement comprises the other of the hook or loop.

5a. A securement system for securing a tube to a patient's face, comprising:
   a dermal patch having a patient side and a tube side, the patient side of the dermal patch being attachable to the skin of a user,
   a tail portion coupled to the dermal patch for attaching to a tube, the tube positioned on the tube side of the dermal patch, to secure a first portion of the tube,
   a head portion coupled to the dermal patch for attaching to the tube to secure a second portion of the tube.

5b. A securement system as claimed in claim 5a, the tail portion being adapted for folding at a first fold line to place the tail portion over the tube, a tube side of the tail portion or the tube side of the dermal patch adapted to fix the tube side of the tail portion to the tube side of the dermal patch to secure the first portion of the tube,
   the head portion being adapted for folding at a second fold line to place the head portion over the tube, a tube side of the head portion or the tube side of the dermal patch adapted to fix the tube side of the head portion to the tube side of the dermal patch to secure a second portion of the tube 5c. A securement system as claimed in claim 5b, the second fold line being arranged at an angle to the first fold line, the head and tail portions holding a bend in the tube between the first and second portions of the tube.

5d. A securement system as claimed in any one of claims 5a to 5c wherein the tail portion is a panel covering a significant portion of the tube side of the dermal patch, the tail portion being larger than the head portion.

5e. A securement system as claimed in any one of claims 5a to 5c wherein the head portion is a panel covering a significant portion of the tube side of the dermal patch, the head portion being larger than the tail portion.

5f. A securement system as claimed in claim 5d or claim 5e wherein the panel has a slot for assisting the panel to conform to a profile of the tube, the slot extending longitudinally with respect to an intended position of the tube on the dermal patch, the slot extending partway along the panel.

5g. A securement system as claimed in any one of claims 5a to 5c wherein the tail portion is adapted for being wrapped around at least a full circumference of the first portion of the tube.

5h. A securement system as claimed in any one of claims 5a to 5g wherein a first part of a first two-part releasable connection arrangement is provided to the tube side of the dermal patch and a second part of the first two part releasable connection arrangement is provided to the tail portion.

5i. A securement system as claimed in any one of claims 5a to 5h wherein a first part of a second two-part releasable connection arrangement is provided to the tube side of the dermal patch and a second part of the second two-part releasable connection arrangement is provided to the head portion.

5j. A securement system as claimed in any one of claims 5a to 5i wherein a first part of an interface two-part releasable connection arrangement is provided to an interface side of one of the head portion, the tail portion or the dermal patch, the first part of the interface two-part releasable connection arrangement for releasably connecting to a second part of the interface two-part releasable connection arrangement coupled to a patient interface.

5k. A securement system as claimed in claim 5j wherein the securement system comprises an interface patch for attaching to a patient interface, and the second part of the interface two-part releasable connection arrangement provided on a patient side of the interface patch.

5l. A securement system as claimed in claim 5h wherein the first part of the two-part releasable connection arrangement comprises a hook or a loop, and the second part of the two-part releasable connection arrangement comprises the other of the hook or loop.

5m. A securement system as claimed in claim 5i wherein the first part of the second two-part releasable connection arrangement comprises a hook or a loop, and the second part of the second two-part releasable connection arrangement comprises the other of the hook or loop.

5n. A securement system as claimed in claim 5j wherein the first part of the interface two-part releasable connection arrangement comprises a hook or a loop, and the second part of the interface two-part releasable connection arrangement comprises the other of the hook or loop.

6a. A securement system for securing a tube to a patient's face, comprising:
 a dermal patch having a patient side and a tube side, the patient side of the dermal patch being attachable to the skin of a user,
 a channel formed in the tube side of the dermal patch for receiving the tube, the dermal patch having thickness dimension sufficient to accommodate the channel.

6b. A securement system as claimed in claim 6a wherein the channel is curved to align the tube with a patient's nasal passage when the dermal patch is positioned on the patient's face and direct the tube across and above the patient's upper lip.

6c. A securement system as claimed in claim 6a or claim 6b wherein the dermal patch comprises notches for providing flexibility to the dermal patch, the channel being formed along a back bone of the dermal patch.

6d. A securement system as claimed in any one of claims 6a to 6c comprising a panel for covering the tube side of the dermal patch.

6e. A securement system as claimed in claim 6d wherein the panel and dermal patch are adapted to be adhered together.

6f. A securement system as claimed in claim 6d comprising a two-part releasable connection arrangement between the panel and the dermal patch.

6g. A securement system as claimed in claim 6d or claim 6f wherein a first part of an interface two-part releasable connection arrangement is provided to an interface side of the panel for releasably connecting to a second part of the interface two-part releasable connection arrangement coupled to or formed with a patient interface.

6h. A securement system as claimed in any one of claims 6a to 6c wherein a first part of an interface two-part releasable connection arrangement is provided to the tube side of the dermal patch for releasably connecting to a second part of the interface two-part releasable connection arrangement coupled to or formed with a patient interface.

6i. A securement system as claimed in claim 6g or claim 6h wherein the securement system comprises an interface patch for attaching to a patient interface, and
 the second part of the interface two-part releasable connection arrangement is provided on a patient side of the interface patch.

6j. A securement system as claimed in any one of claims 6a to 6i wherein the dermal patch is formed from a polymer.

6k. A securement system as claimed in claim 6j wherein the dermal patch is formed from a polymer bonded to a backing sheet.

6l. A securement system as claimed in claim 6j or 6k wherein the polymer is a silicone.

6m. A securement system as claimed in claim 6k wherein the backing sheet is a hydrocolloid.

6n. A securement system as claimed in claim 6f wherein a first part of the two-part releasable connection arrangement comprises a hook or a loop, and a second part of the two-part releasable connection arrangement comprises the other of the hook or loop.

6o. A securement system as claimed in any one of claims 6g to 6i wherein the first part of the interface two-part releasable connection arrangement comprises a hook or a loop, and the second part of the interface two-part releasable connection arrangement comprises the other of the hook or loop.

7a. A securement system for securing a tube to a patient's face, comprising:
 a dermal patch having a patient side and a tube side, the patient side of the dermal patch being attachable to the skin of a user,
 a channel for receiving the tube, the channel attached to, or the dermal patch or channel attachable to the other one of the channel or dermal patch, to secure the tube to the dermal patch via the channel.

7b. A securement system as claimed in claim 7a wherein the channel comprises notches for providing flexibility to the channel.

7c. A securement system as claimed in claim 7a or claim 7b wherein the channel is slotted or open to one side.

7d. A securement system as claimed in any one of claims 7a to 7c wherein a first part of an interface two-part releasable connection arrangement is provided to the tube side of the dermal patch for releasably connecting to a second part of the interface two-part releasable connection arrangement coupled to or formed with a patient interface.

7e. A securement system as claimed in claim 7d wherein the securement system comprises an interface patch for attaching to a patient interface, and
 the second part of the interface two-part releasable connection arrangement provided on a patient side of the interface patch.

7f. A securement system as claimed in any one of claims 7a to 7e wherein at least a surface of the channel for contacting the tube is formed from a rubber material or a material having a high surface friction.

7g. A securement system as claimed in claim 7d or claim 7e wherein the first part of the interface two-part releasable connection arrangement comprises a hook or a loop, and the second part of the interface two-part releasable connection arrangement comprises the other of the hook or loop.

8a. A securement system for securing a tube to a patient's face, comprising:
 a dermal patch having a patient side attachable to the skin of a user, the dermal patch comprising a wing portion attachable to the tube for affixing the tube to the dermal patch by wrapping the wing portion around the tube so that an initially patient facing side of the wing portion adheres to the tube.

8b. A securement system as claimed in claim 8a wherein a first part of an interface two-part releasable connection arrangement is provided to an outer side of the dermal patch for releasably connecting to a second part of the interface two-part releasable connection arrangement coupled to or formed with a patient interface.

8c. A securement system as claimed in claim 8b wherein the securement system comprises an interface patch for attaching to a patient interface, and the second part of the interface two-part releasable connection arrangement provided on a patient side of the interface patch.

8d. A securement system as claimed in any one of claims 8a to 8c comprising a plurality of transverse notches located along the wing portion.

8e. A securement system as claimed in any one of claims 8a to 8d wherein the wing portion is detachable from a main portion of the dermal patch for attachment to the patient.

8f. A securement system as claimed in any one of claims 8a to 8e wherein the dermal patch comprises a notch along a join line between a main portion of the patch and the wing portion.

8g. A securement system as claimed in 8f wherein the dermal patch comprises a notch along the join line at each end of the join line.

8h. A securement system as claimed in any one of claims 8a to 8g wherein the patient side comprises an adhesive, the adhesive of the winged portion providing a releasable bond to itself or the tube once wrapped around the tube.

8i. A securement system as claimed in claim 8b wherein the first part of the interface two-part releasable connection arrangement comprises a hook or a loop, and the second part of the interface two-part releasable connection arrangement comprises the other of the hook or loop.

8j. A securement system for securing a tube to a patient's face, comprising:
a dermal patch having a patient side attachable to the skin of a user, the dermal patch comprising a wing portion attachable to the tube for affixing the tube to the dermal patch by wrapping the wing portion around the tube, and
a plurality of transverse notches located along the wing portion.

8k. A securement system for securing a tube to a patient's face, comprising:
a dermal patch having a patient side attachable to the skin of a user, the dermal patch comprising a wing portion attachable to the tube for affixing the tube to the dermal patch by wrapping the wing portion around the tube, and
a notch along a join line between a main portion of the patch and the wing portion.

8l. A securement system as claimed in claim 8k wherein the dermal patch comprises a notch along the join line at each end of the join line.

9a. A securement system for securing a tube to a patient's face, comprising:
a dermal patch having a patient side attachable to the skin of a user, for securing a tube to a patient by placing the dermal patch over the tube on the patient's face, the dermal patch comprising a slot extending longitudinally with respect to an intended position of the tube under the dermal patch, the slot extending partway along the dermal patch.

9b. A securement system as claimed in claim 9a wherein a first part of an interface two-part releasable connection arrangement is provided to an interface side of the dermal patch for releasably connecting to a second part of the interface two-part releasable connection arrangement coupled to a patient interface.

9c. A securement system as claimed in either claim 9a or 9b wherein the securement system comprises an interface patch for attaching to a patient interface, and
the second part of the interface two-part releasable connection arrangement provided on a patient side of the interface patch.

9d. A securement system as claimed in any one of claims 9a to 9c wherein the dermal pad has a thickness similar to or greater than a diameter of the tube.

9e. A securement system as claimed in claim 9b or claim 9c wherein the first part of the interface two-part releasable connection arrangement comprises a hook or a loop, and the second part of the interface two-part releasable connection arrangement comprises the other of the hook or loop.

10a. A securement system for securing a tube to a patient's face, comprising:
a dermal patch having a patient side and a tube side, the patient side of the dermal patch being attachable to the skin of a user,
a tube pad comprising:
a patient side and an outer side, the patient side of the tube pad attachable to the tube side of the dermal patch, and
a tab for wrapping about the tube and adhering to the tube.

10b. A securement system as claimed in claim 10a wherein the securement system comprises a cover patch for applying to the tube side of the dermal patch and covering at least a portion of the outer side of the tube pad.

10c. A securement system as claimed in claim 10a or claim 10b wherein the securement system comprises a two-part releasable connection arrangement, a first part of the two-part releasable connection arrangement provided to the tube side of the dermal patch and a complementary second part of the two-part releasable connection arrangement provided to the patient side of the tube pad.

10d. A securement system as claimed in claim 10b or claim 10c wherein the securement system comprises a two-part releasable connection arrangement, a first part of the two-part releasable connection arrangement provided to the outer side of the tube pad and a complementary second part of the two-part releasable connection arrangement provided to a patient side of the cover patch.

10e. A securement system as claimed in any one of claims 10b to 10d wherein the securement system comprises a two-part releasable connection arrangement, a first part of the two-part releasable connection arrangement provided to the tube side of the dermal patch and a complementary second part of the two-part releasable connection arrangement provided to a patient side of the cover patch.

10f. A securement system as claimed in any one of claims 10b to 10e wherein the cover patch is an interface patch having a patient side and an interface side, the interface side attachable to a patient interface.

10g. A securement system as claimed in any one of claims 10b to 10e wherein the cover patch is a backing of a patient interface attachable to the tube side of the dermal patch or the outer side of the tube pad.

10h. A securement system as claimed in any one of claims 10c to 10e wherein the first part of the two-part releasable connection arrangements comprises a hook or a loop, and the second part of the two-part releasable connection arrangement comprises the other of the hook or loop.

11a. A securement patch for securing a tube for treating a patient to a surface comprising:
an adhesive applied to a side of the patch for adhering the patch to the surface,
a notch in the edge of the patch at a position intended to be crossed by the tube, the patch comprising a foot either side of the notch.

11b. A securement patch as claimed in claim 11a wherein the patch is a dermal patch for adhering to the skin of a patient for securing the tube to the patient.

11c. A securement patch as claimed in claim 11a wherein the patch is a panel for adhering to a patient interface for securing the tube to the patient interface.

11d. A securement patch as claimed in any one of claims 11a to 11c wherein the notch has a depth and the depth is equal to or greater than the diameter of the tube to be secured.

11e. A securement patch as claimed in claim 11d wherein the depth is at least twice the diameter of the tube to be secured.

11f. A securement patch as claimed in claim 11d wherein the depth is at least three times the diameter of the tube to be secured.

11g. A securement patch as claimed in claim 11d wherein the depth is at least four times the diameter of the tube to be secured.

11h. A securement patch as claimed in any one of claims 11a to 11g wherein the patch has two said notches spaced apart on the perimeter of the patch.

11i. A securement patch as claimed in any one of claims 11a to 11h wherein when a force acts on the tube in a direction through the plane of the patch, that force is spread out over an area of the patch including the foot to prevent an edge of the patch crossed by the tube from peeling away from the surface.

12a. A securement system for securing a tube to a patient's face, comprising:
a dermal patch having a patient side and a tube side, the patient side of the dermal patch being attachable to the skin of a user, and
a panel having a tube side and an opposite side, the tube side of the dermal patch and the tube side of the panel adapted to be connected together by an adhesive to retain the tube there between,
a first portion of the dermal patch and the panel being coupled together at a fold region, and a removable liner being attached to a second portion of one of the dermal patch and the panel, the liner removable for connecting the tube side of the dermal patch and the tube side of the panel together.

12b. A securement system as claimed in claim 12a comprising a second removable liner attached to the patient side of the dermal patch, the second removable liner removable for attaching the patient side of the dermal patch to a patient.

12c. A securement system as claimed in claim 12b wherein the second removable liner is attached to a first portion of the patient side of the dermal patch and a third removable liner is attached to a second portion of the patient side of the dermal patch and overlapping a portion of the second removable line, the second portion of the patient side of the dermal patch for attaching near the nostril of the patient.

12d. A securement system as claimed in any one of claims 12a to 12c wherein a first part of a two-part releasable connection arrangement provided to the opposite side of the panel, the first part adapted to be connected to a second part of the two-part releasable connection arrangement attached to or formed with a patient interface.

12e. A securement system as claimed in claim 12d wherein the securement system comprises an interface patch, the interface patch having a patient side and an interface side, and the second part of the two-part releasable connection provided to the patient side of the interface patch, and the interface side of the interface patch adapted for connection to the patient interface.

12f. A securement system as claimed in claim 12d or 12e wherein the first part of the two-part releasable connection arrangement comprises a hook or a loop, the second part of the two-part releasable connection arrangement comprising the other of the hook or loop.

13a. A securement system for securing a tube and a patient interface to a patient's face, comprising:
a patient interface for providing a flow of gases to a patient, the patient interface comprising a backing for positioning on a patient's face,
a dermal patch having a patient side and an interface side, the patient side of the dermal patch being attachable to the skin of a user, the dermal patch comprising at least a first flap portion attachable to the tube for affixing the tube to the dermal patch by wrapping the flap portion around the tube,
a two-part releasable connection arrangement for releasably securing the patient interface to the dermal patch, a first part of the two-part releasable connection arrangement provided to the interface side of the dermal patch and a complementary second part of the two-part releasable connection arrangement attached to or formed with a patient side of the backing of the patient interface,
optionally wherein
the backing comprises a flap for securing over a feeding tube located between the flap and the dermal patch, the flap formed by a slit extending from an edge of the backing to a position inside of a perimeter of the backing.

13b. A securement system as claimed in claim 13a comprising an over patch for securing over the flap and a portion of the dermal patch.

13c. A securement system as claimed in claim 13a or 13b wherein the first part of the two-part releasable connection arrangement comprises a hook or a loop, and the second part of the two-part releasable connection arrangement comprises the other of the hook or loop.

13d. A securement system as claimed in any one of claims 13a to 13c, wherein said flap is bifurcated or trifurcated.

13e. A securement system as claimed in any one of claims 13a to 13d, wherein said flap is divided into three flap portions, a first flap portion being a substantially central flap portion for connection to at least the septum region of a patient's nose, and a second and third flap portions each of which are substantially adjacent said first flap portion, one of the second or third flap portions for connection to at least a region about or near a nare or nostril of a patient's nose region and the other of the second or third flap portions for connection to the tube.

13f. A securement system as claimed in claim 13e, wherein said second or third flap portion connected to said tube is a wrapped connection about said tube.

13g. A securement system as claimed in any one of claims 13a to 13f, wherein said flap comprises an adhesive for connection to said patient or said tube.

13h. A securement system as claimed in claim 13g, wherein said adhesive is a pressure sensitive adhesive.

13i. A securement system as claimed in claim any one of claims 13a to 13h, wherein said flap secures or retains both a patient interface and said tube in an operational position on a patient.

13j. A securement system as claimed in any one of claims 13a to 13i, wherein said tube is a feeding tube.

14a. A securement system for securing a tube to a patient interface or a dermal patch comprising:
a holder, an interface side of the holder attachable to the patient interface or the dermal patch for securing a feeding tube to the patient interface or the dermal patch, optionally the holder comprising at least a first channel or recess for receiving the feeding tube to couple the feeding tube to the patient interface.

14b. A securement system as claimed in claim 14a wherein an adhesive is provided to the interface side of the holder for bonding the holder to the patient interface or dermal patch.

14c. A securement system as claimed in claim 14a or claim 14b wherein an adhesive is provided to the interface side of the holder for bonding the holder to the patient interface or dermal patch and the tube.

14d. A securement system as claimed in claim 14a wherein hook and loop material is provided between the holder and the patient interface or dermal patch.

14e. A securement system as claimed in any one of claims 14a to 14d wherein the holder is formed from a soft or pliable material.

14f. A securement system as claimed in any one of claims 14a to 14d wherein the holder is formed from a rigid material for clipping to the patient interface or dermal patch.

14g. A securement system as claimed in any one of claims 14a to 14f wherein the holder comprises a male or female part or feature and the patient interface or dermal patch comprises a complementary other one of the male and female part, the male and female parts for securing the holder to the patient interface or the dermal patch.

14h. A securement system as claimed in any one of claims 14a to 14g wherein the recess or first channel comprises an aperture for receiving the tube.

14i. A securement system as claimed in claim 14h, the recess having a lateral dimension similar to or slightly smaller than a diameter of the tube for firmly gripping the tube.

14j. A securement system as claimed in claim 14h or claim 14i wherein a surface of the recess for contacting the tube is formed from a rubber material or a material having a high surface friction.

14k. A securement system as claimed in any one of claims 14a to 14j wherein the holder comprises a material for wrapping around the tube to couple the holder to the tube.

14l. A securement system as claimed in claim 14g wherein the securement system comprises a dermal patch and the complimentary other one of the male and female part is permanently fixed to the dermal patch.

14m. A securement system as claimed in claim 14k wherein the material comprises a strap with adhesive on one or both sides for contact by wrapping the material around the tube and onto itself.

14n. A securement system as claimed in any one of claims 14a to 14m, wherein said holder comprises a body, said body including said first channel or recess for connecting, retaining or attaching to said tube, and wherein said body further comprises at least one further channel or recess (or aperture) for connecting, retaining or attaching to said patient interface.

14o. A securement system as claimed in claim 14n, wherein said first channel or recess is a moulded region of said body receivable of said tube.

14p. A securement system as claimed in claim 14n or 14o, wherein said at least one further channel or recess is a moulded region of said body receivable of a portion of said patient interface.

14q. A securement system as claimed in any one of claims 14n to 14p, wherein said first channel or recess extends substantially orthogonally relative to said at least one further channel or recess.

14r. A securement system as claimed in any one of claims 14a to 14g, wherein said holder is mounted, or mountable to, to the patient interface or the dermal patch.

14s. A securement system as claimed in any one of claims 14a to 14r, wherein the first channel or recess is to have an internal dimension smaller than the diameter of the tube when the holder is in an unstressed or un-deformed state for gripping the tube, and said first channel or recess (or aperture) being elastically deformable to increase the internal dimension to be greater than the diameter of the tube to un-grip the tube for adjustment between the tube and the holder.

14t. A securement system as claimed in any one of claims 14a to 14s, wherein the at least one other channel or recess (or aperture) is sized to have an internal dimension smaller than a dimension of the patient interface or a portion of the patient interface when the holder is in an unstressed or un-deformed state for gripping the patient interface, and the at least one other channel or recess (or aperture) being elastically deformable to increase the internal dimension to be greater than the dimension of the patient interface or the portion of the patient interface dimension to un-grip the patient interface or said portion for adjustment between the patient interface and the holder.

14u. A securement system as claimed in any one of claims 14n to 14t, wherein said body further comprises at least one further first channel or recess for connecting, retaining or attaching to said tube.

15a. A patient interface comprising a conduit for receiving a feeding tube for securing the feeding tube to the patient interface.

15b. A patient interface as claimed in claim 15a wherein the patient interface comprises a nasal prong and the conduit comprises an elbow or bend for maintaining a bend in the feeding tube to align the feeding tube with the nasal prong.

15c. A patient interface as claimed in claim 15a or claim 15b wherein the patient interface comprises a nasal prong and the conduit is provided within a nasal prong 15d. A patient interface as claimed in claim 15c wherein the conduit enters the prong at a base of the prong.

16a. A securement system for securing a tube to a patient interface, the patient interface comprising a nasal prong, the securement system comprising:

a hollow member for receiving the patient interface nasal prong and the tube to couple the tube to the patient interface, the hollow member adapted to fit in the nasal passage of a patient.

16b. A securement system as claimed in claim 16a wherein the hollow member is shorter in length than the length of the nasal prong.

16c. A securement system as claimed in claim 16a or claim 16b wherein an inside surface of the hollow member comprises a high surface friction material for contacting the tube and the nasal prong.

16d. A securement system as claimed in claim 16c wherein the high surface friction material is a rubber material.

16e. A securement system as claimed in claim 16a or claim 16d wherein the hollow member is open along its length by a longitudinal slot for inserting the tube laterally into the hollow member.

16f. A securement system as claimed in claim 16a or claim 16e wherein the hollow member is formed of a soft material for conforming to the patient's nasal passage.

17a. A patient interface comprising a ring of material defining an aperture for receiving a tube, and with the ring in an unstressed or un-deformed state, the aperture having an internal dimension smaller than the diameter of the tube for gripping the tube, and with the ring in an elastically deformed state the aperture having an internal dimension greater than the diameter of the tube to un-grip the tube for adjustment between the tube and the patient interface.

17b. A patient interface as claimed in claim 17a wherein the patient interface comprises a second aperture for receiving the tube, the second aperture loosely capturing the tube to the patient interface.

17c. A patient interface as claimed in claim 17a or claim 17b wherein the patient interface comprises two nasal prongs and the ring is located between the two nasal prongs.

17d. A patient interface as claimed in any one of claims 17a to 17c wherein the ring comprises a slot for inserting the tube into the aperture.

17e. A patient interface as claimed in any one of claims 17a to 17d wherein the ring of material comprises a clip for securing the tube at the aperture, the clip comprising a male part and a female part formed in the ring opposite the male part, the ring closable on the tube by mating the male and female parts.

17f. A patient interface as claimed in claim 17e wherein the ring comprises a recess for receiving the tube, the tube lockable in the recess by mating the male part with the female part.

17g. A patient interface as claimed in any one of claims 17a to 17f wherein the ring is adapted to be squeezed by the thumb and forefinger of a user to elastically deform the aperture to release the tube.

18a. A holder for securing a tube to a patient interface, the holder comprising a first aperture for receiving a part of the patient interface and a second aperture for receiving the tube to couple the tube to the patient interface.

18b. A holder as claimed in claim 18a wherein patient interface comprises a nasal prong and the first aperture is sized for receiving the nasal prong.

18c. A holder as claimed in claim 18b wherein the patient interface comprises two nasal prongs and the holder comprises two first apertures each said first aperture for receiving a corresponding nasal prong.

18d. A holder as claimed in any one of claims 18a to 18c wherein the second aperture is open to a side via a slit.

18e. A holder as claimed in any one of claims 18a to 18d wherein the first aperture is open to a side via a slit.

18f. A holder as claimed in claim 18a wherein the patient interface comprises two nasal prongs and the first aperture is sized to receive a portion of the patient interface extending between the two nasal prongs, the first aperture being open to a side via a slit.

18g. A holder as claimed in claim 18a wherein the patient interface comprises two nasal prongs and the holder comprises a plurality of first apertures, each first aperture sized to receive a portion of the patient interface extending between the two nasal prongs or a portion of the patient interface outside of the two nasal prongs, each first aperture being open to a side via a slit.

18h. A holder as claimed in claim 18a wherein the patient interface comprises a breathing tube and the first aperture is sized for receiving the breathing tube.

18i. A holder as claimed in claim 18h wherein the first aperture is sized to allow the holder to slide longitudinally along the breathing tube.

18j. A holder as claimed in any one of claims 18a to 18i wherein the material bordering the first aperture comprises a high surface friction material for providing a grip surface to the patient interface.

18k. A holder as claimed in any one of claims 18a to 18j wherein the material bordering the second aperture comprises a high surface friction material for providing a grip surface to the tube.

18l. A holder as claimed in any one of claims 18a to 18k wherein the first aperture is sized to have an internal dimension smaller than a dimension of the patient interface when the holder is in an unstressed or un-deformed state for gripping the patient interface.

18m. A holder as claimed in any one of claims 18a to 18l wherein the first aperture is sized to have an internal dimension smaller than a dimension of the patient interface when the holder is in an unstressed or un-deformed state for gripping the patient interface, and the first aperture being elastically deformable to increase the internal dimension to be greater than the dimension of the patient interface dimension to un-grip the patient interface for adjustment between the patient interface and the holder.

18n. A holder as claimed in any one of claims 18a to 18m wherein the second aperture is sized to have an internal dimension smaller than the diameter of the tube when the holder is in an unstressed or un-deformed state for gripping the tube, and the second aperture being elastically deformable to increase the internal dimension to be greater than the diameter of the tube to un-grip the tube for adjustment between the tube and the holder.

18o. A holder as claimed in any one of claims 18a to 18n wherein the patient interface comprises a clip for coupling the holder to the patient interface.

18p. A holder as claimed in claim 18o wherein the clip has a male or female part and the holder has a complementary other one of the male and female part for coupling the holder to the patient interface.

18q. A holder as claimed in claim 18p wherein the second aperture are the same size or of a similar size.

18r. A holder as claimed in any one of claims 18a to 18q wherein the second aperture comprises a primary recess and a secondary recess, the primary recess having a first internal dimension for holding the tube, and the secondary recess having a second internal dimension for holding the tube, and the first internal dimension being larger than the second internal dimension, the primary recess and the secondary recess coupled together via an opening.

18s. A holder as claimed in claim 18b wherein the holder comprises a base, the first and second apertures formed in the base, and a shield extending from the base, the shield for shrouding or enveloping the tube and the prong.

18t. A holder as claimed in claim 18s wherein the shield extends around the first aperture and the second aperture.

18u. A holder as claimed in any one of claims 18s or 18t wherein the shield comprises a longitudinal slit providing an opening for inserting the feeding tube laterally into the shield.

18v. A holder as claimed in any one of claims 18s to 18u, the shield may having an approximately cylindrical or frusto-conical form extending from the base.

18w. A holder as claimed in claim 18m wherein the holder is adapted to be squeezed by the thumb and forefinger of a user to elastically deform the first aperture to release the patient interface.

18x. A holder as claimed in claim 18n wherein the holder is adapted to be squeezed by the thumb and forefinger of a user to elastically deform the second aperture to release the tube.

19a. A securement system for securing a tube to a patient, comprising a dermal patch having a patient side attachable to the skin of a user, and a tube adhesive side, at least a portion of the tube adhesive side being provided with a first adhesive part of a tube two-part adhesive connection arrangement, and a complementary second tube adhesive part adhesively connectable to the first tube adhesive part on the dermal patch, for affixing the tube to the dermal patch, the second tube adhesive part having higher adhesion/bond strength than the first tube adhesive part.

19b. A securement system according to claim 19a wherein the second tube adhesive part comprises a panel having a tube adhesive side.

19c. A securement system according to claim 19b wherein the panel is coupled to the dermal patch at a fold region.

19d. A securement system according to claim 19c wherein the dermal patch has a width and a greater length and the fold region is approximately in the length of the dermal patch.

19e. A securement system according to claim 19b wherein the panel is a separate component from the dermal patch.

19f. A securement system according to any one of claims 19a to 19e wherein the first tube adhesive part comprises a first removably attached protective backing sheet and the second or tube side adhesive part comprises a separate second removably attached protective backing sheet.

19g. A securement system according to any one of claims 19a to 19f wherein removably attached protective backing sheet or sheets over the first and second tube adhesive parts extend beyond an external periphery of the adhesive parts.

19h. A securement system according to any one of claims 19a to 19g wherein the patient side of the dermal patch comprises an adhesive for attaching the dermal patch to the skin of a user, and is provided with a removably attached protective backing sheet.

19i. A securement system according to any one of claims 19a to 19h wherein the adhesion/bond strength of the second tube adhesive part is at least two, five, or more times higher than the adhesion/bond strength of the first tube adhesive part.

20a. A securement system for securing a tube to a patient, comprising a dermal patch having a patient side and a tube side, the patient side of the dermal patch being adhesively attachable to the skin of a user, a panel foldably coupled to the dermal patch on the tube side, at least a portion of a tube side of the dermal patch and at least a portion of a tube side of the panel each carrying a tube attachment adhesive, the tube attachment adhesive areas on the tube side of the dermal patch and the tube side of the panel being provided with separately removable protective backing sheets.

20b. A securement system according to claim 20a wherein the adhesion/bond strength of the adhesive on the tube side of the dermal patch enables initial attachment of the tube thereto and then release and re-attachment of the tube thereto to reposition the tube.

The invention claimed is:

1. A system for securing a tube to a patient's face, comprising:
  a patient interface configured to provide a flow of gases to a patient, the patient interface comprising a backing for positioning on a patient's face,
  a securement system comprising a dermal patch, a flap, and a fold region between the dermal patch and the flap, the dermal patch forming a patient side of the securement system and the flap forming an interface side of the securement system, the patient side of the securement system being attachable to the skin of the patient, the flap attachable to the tube for affixing the tube to the securement system by folding the flap along the fold region and over the tube, the fold region positioned along a periphery of the securement system when the flap is folded over the tube;
  a two-part releasable connection arrangement for releasably securing the patient interface to the securement system, a first part of the two-part releasable connection arrangement provided to the interface side of the securement system and a complementary second part of the two-part releasable connection arrangement attached to or formed with a patient side of the backing of the patient interface.

2. A system as claimed in claim 1, comprising an over patch for securing over the flap and a portion of the dermal patch.

3. A system as claimed in claim 1, wherein the first part of the two-part releasable connection arrangement comprises a hook or a loop, and the second part of the two-part releasable connection arrangement comprises the other of the hook or loop.

4. A system as claimed in claim 1, wherein said flap is bifurcated or trifurcated.

5. A system as claimed in claim 1, wherein said flap is divided into three flap portions, a first flap portion being a substantially central flap portion for connection to at least the septum region of a patient's nose, and a second and third flap portions each of which are substantially adjacent said first flap portion, one of the second or third flap portions for connection to at least a region about or near a nare or nostril of the patient's nose and the other of the second or third flap portions for connection to the tube.

6. A system as claimed in claim 5, wherein said second or third flap portion connected to said tube is a wrapped connection about said tube.

7. A system as claimed in claim 1, wherein said flap comprises an adhesive for connection to said patient or said dermal patch.

8. A system as claimed in claim 7, wherein said adhesive is a pressure sensitive adhesive.

9. A system as claimed in claim 1, wherein said flap secures or retains both the patient interface and said tube in an operational position on the patient.

10. A system as claimed in claim 1, wherein said tube is a feeding tube.

11. A system as claimed in claim 1, wherein said tube is sandwiched between said dermal patch and said flap.

12. A system as claimed in claim 1, wherein said first part of the two-part releasable connection arrangement is provided to an interface side of said flap.

13. A system as claimed in claim 1, wherein said flap is coupled to said dermal patch at said fold region.

14. A system as claimed in claim 1, wherein said fold region is approximately parallel to an intended position of said tube.

15. A system as claimed in claim 1, wherein a tube side of said dermal patch comprises an adhesive.

16. A system as claimed in claim 1, wherein said dermal patch comprises a hydrocolloid material.

17. A system as claimed in claim 1, wherein said flap comprises a hydrocolloid material.

18. A system as claimed in claim 1, wherein said flap is integrally formed with said dermal patch.

19. A system as claimed in claim 1, wherein said patient interface comprises a nasal cannula.

20. A system as claimed in claim 1, said dermal patch having a patient side and an opposing tube side, said flap having a tube side and an opposing interface side, the patient side of the dermal patch comprising the patient side of the securement system, the interface side of the flap comprising the interface side of the securement system, and the tube side of the flap configured to face and contact the tube side of the dermal patch when the flap is folded over the tube.

21. A system as claimed in claim 20, said patient side of said dermal patch facing a first direction, said tube side of said dermal patch facing a second, opposite direction, said tube side of said flap facing the second direction in an unfolded state, said interface side of said flap facing the first direction in the unfolded state, said tube side of said flap facing the first direction when said flap is folded over the tube, and said interface side of said flap facing the second direction when said flap is folded over said tube, wherein when said flap is folded over said tube, at least a portion of said flap overlaps at least a portion of said dermal patch.

22. A securement system as claimed in claim 1, wherein the first part of the two-part releasable connection arrangement comprises a substrate provided to the interface side of the securement system.

* * * * *